(12) United States Patent
Blumberg et al.

(10) Patent No.: US 10,035,858 B2
(45) Date of Patent: Jul. 31, 2018

(54) COMPOSITIONS AND METHODS FOR MODULATING AN IMMUNE RESPONSE

(71) Applicant: The Brigham and Women's Hospital, Inc., Boston, MA (US)

(72) Inventors: Richard S. Blumberg, Waltham, MA (US); Kristi Baker, Brookline, MA (US); Timo Rath, Cambridge, MA (US)

(73) Assignee: THE BRIGHAM AND WOMEN'S HOSPITAL, INC., Boston, MA (US)

( * ) Notice: Subject to any disclaimer, the term of this patent is extended or adjusted under 35 U.S.C. 154(b) by 0 days.

(21) Appl. No.: 15/039,524

(22) PCT Filed: Nov. 25, 2014

(86) PCT No.: PCT/US2014/067332
§ 371 (c)(1),
(2) Date: May 26, 2016

(87) PCT Pub. No.: WO2015/081073
PCT Pub. Date: Jun. 4, 2015

(65) Prior Publication Data
US 2017/0002073 A1  Jan. 5, 2017

Related U.S. Application Data

(60) Provisional application No. 61/909,229, filed on Nov. 26, 2013.

(51) Int. Cl.
| | |
|---|---|
| *G01N 33/53* | (2006.01) |
| *C07K 16/28* | (2006.01) |
| *G01N 33/574* | (2006.01) |
| *G01N 33/68* | (2006.01) |
| *C07K 16/24* | (2006.01) |
| *C07K 16/00* | (2006.01) |
| *C12N 15/113* | (2010.01) |
| *G01N 33/564* | (2006.01) |
| *A61K 39/00* | (2006.01) |

(52) U.S. Cl.
CPC ........ *C07K 16/283* (2013.01); *A61K 39/0011* (2013.01); *C07K 16/00* (2013.01); *C07K 16/244* (2013.01); *C12N 15/1138* (2013.01); *G01N 33/564* (2013.01); *G01N 33/574* (2013.01); *G01N 33/6854* (2013.01); *G01N 33/6863* (2013.01); *G01N 33/6866* (2013.01); *G01N 33/6869* (2013.01); *A61K 2039/505* (2013.01); *A61K 2039/507* (2013.01); *C07K 2317/21* (2013.01); *C07K 2317/31* (2013.01); *C07K 2317/52* (2013.01); *C07K 2317/72* (2013.01); *C07K 2317/76* (2013.01); *C12N 2310/14* (2013.01); *G01N 2333/525* (2013.01); *G01N 2333/5434* (2013.01); *G01N 2333/57* (2013.01); *G01N 2800/52* (2013.01)

(58) Field of Classification Search
CPC ............. G01N 33/564; G01N 33/6854; G01N 33/6863
See application file for complete search history.

(56) References Cited

U.S. PATENT DOCUMENTS

| | | | |
|---|---|---|---|
| 6,086,875 | A | 7/2000 | Blumberg et al. |
| 2007/0092507 | A1 | 4/2007 | Balthasar et al. |
| 2008/0181887 | A1 | 7/2008 | Dall-Acqua et al. |
| 2009/0041770 | A1 | 2/2009 | Chamberlain et al. |

FOREIGN PATENT DOCUMENTS

| | | |
|---|---|---|
| WO | 2006/118772 A2 | 11/2006 |
| WO | 2012/167039 A1 | 12/2012 |

OTHER PUBLICATIONS

Kobayashi et al., "An FcRn-dependent role for anti-flagellin immunoglobulin G in pathogenesis of colitis in mice", Gastroenterology 137(5) 1746-1756 (2009).
Kobayashi et al., "1046 Anti-Flagellin Specific IgG is Pathogenic in Colitis Through FcRn-Regulated Antigen Presentation Pathways", Gastroenterology 134(4):A-156 (2008).
Low et al., "Inhibitors of the FcRn:IgG protein-protein interaction", AAPS 11(3) 432-434 (2009).
McDonnell et al., "Synthesis and structure-activity relationships of dimeric peptide antagonists of the human immunoglobulin G-human neonatal Fc receptor (IgG-FcRn) interaction", J Med Chem 53(4) 1587-1596 (2010).
Pollard et al., "β2-microglobulin is required for the full expression of xenobiotic-induced systemic autoimmunity", J Immunotoxicolo 8(3) 228-237 (2011).
Sesarman et al., "The neonatal Fc receptor as therapeutic target in IgG-mediated autoimmune diseases", Cell Mol Life Sci 67(15) 2533-2550 (2010).
Qiao et al, "Dependence of antibody-mediated presentation of antigen on FcRn", PNAS, vol. 105, No. 27, pp. 9337-9342, 2008.

*Primary Examiner* — Prema Mertz
(74) *Attorney, Agent, or Firm* — Nixon Peabody LLP; Mark J. FitzGerald; Srividya Subramanian

(57) ABSTRACT

Described herein are compositions for increasing IL-12 production comprising IgG or a fragment thereof or a variant thereof and uses of said compositions for treating cancer and infectious diseases. Also described herein are compositions for decreasing IL-12 production comprising an agent that inhibits signaling mediated by interaction between FcRn and IgG and uses of said compositions for treating autoimmune diseases. Further described herein are methods for assessing efficacy of treatment by monitoring levels of various cytokines in the subject.

2 Claims, 16 Drawing Sheets

COMPOSITIONS AND METHODS FOR MODULATING AN IMMUNE RESPONSE

CROSS-REFERENCE TO RELATED APPLICATIONS

This application is a 35 U.S.C. § 371 National Phase Entry Application of International Application No. PCT/US2014/067332 filed Nov. 25, 2014, which designated the U.S., and claims benefit under 35 U.S.C. § 119(e) of U.S. Provisional Application No. 61/909,229 filed Nov. 26, 2013, the contents of which are incorporated herein by reference in their entirety.

GOVERNMENT RIGHTS

The invention was made with government support under Grant No. DK53056 awarded by the National Institutes of Health. The government has certain rights to the invention.

FIELD OF INVENTION

The present invention relates to molecular immunology and cell biology. Specifically, described herein are compositions for increasing production of IL-12 by regulating the interactions between IgG and FcRn and methods of using the composition for treating cancer and infectious diseases in a subject. Also described herein are compositions for decreasing production of IL-12 by regulating the interactions between IgG and FcRn and methods of using the composition for treating autoimmune diseases in a subject. Also provided herein are methods for assessing efficacy of treatment in a subject by monitoring the levels of various cytokines.

BACKGROUND OF THE INVENTION

All publications cited herein are incorporated by reference in their entirety to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Cancers arising at mucosal barrier sites, particularly the lung, large intestine (LI), stomach and cervix, account for a considerable fraction of human malignancies (Siegel et al., 2012). One contributing factor to the colon's susceptibility to malignant transformation is its immunosuppressive environment (MacDonald et al., 2011) which is necessary for tolerance towards microbial and dietary antigens but also results in dampened anti-cancer immune responses (Revaz and Nardelli-Haefliger, 2005; Saleh and Trinchieri, 2011). Identifying physiologic factors capable of countering this inherent downside of local tolerance is critical for understanding and manipulating carcinogenesis at this, and possibly other, mucosal sites.

The production and handling of IgG are critical components of mucosal immunity, particularly in the LI where IgG accounts for a large fraction of homeostatic mucosal immunoglobulin secretion (Kozlowski et al., 1997). The presence of IgG in the intestinal lumen is associated with the actions of the bidirectional IgG transport receptor, FcRn (neonatal Fc receptor for IgG), which is expressed lifelong in most murine and human endothelial, epithelial and hematopoietic cells (Claypool et al., 2004; Zhu et al., 2001). FcRn is uniquely capable of delivering IgG into the lumen and also retrieving lumenal IgG and IgG containing immune complexes (IgG IC) which are delivered into the local immune system of the lamina propria (LP) (Claypool et al., 2004; Yoshida et al., 2004). FcRn within antigen presenting cells such as dendritic cells (DC) also plays a critical role in the processing of antigens delivered as IgG IC and actively promotes major histocompatibility complex (MHC) class I and class II restricted T cell responses (Baker et al., 2011; Qiao et al., 2008) which can alternatively promote antibacterial IgG-driven colitis (Kobayashi et al., 2009) and protect from mucosal pathogens (Qiao et al., 2008; Yoshida et al., 2006).

It is well accepted that cytotoxic CD8+ T cell-mediated responses are critical for efficient anti-tumor immunity (Pages et al., 2005) and FcRn has recently been shown to enable highly efficient cross-presentation of IgG-complexed antigens by CD8−CD11b+ DC (Baker et al., 2011). Given the abundance of both IgG and CD8−CD11b+ monocyte-derived DC in mucosal tissues, especially in the context of malignancy (Kozlowski et al., 1997; Ma et al., 2011; MacSween and Eastwood, 1980), the role of FcRn in homeostatic CD8+ T cell responses and as an effector of anti-cancer immune surveillance was examined Described herein are findings showing that FcRn ligation with IgG containing immune complexes (IgG IC) is directly involved in the production of IL-12, a key regulator of an immune response. Production of IL-12 may thus be targeted with agents that increase IL-12 production via altered FcRn/IgG interactions so as to treat cancer and/or infectious diseases or with agents that decrease IL-12 production via altered FcRn/IgG interactions so as to treat autoimmune diseases, therefore meeting a need for therapeutic agents to treat cancer, infectious diseases and autoimmune diseases.

SUMMARY OF THE INVENTION

The following embodiments and aspects thereof are described and illustrated in conjunction with systems, compositions and methods which are meant to be exemplary and illustrative, not limiting in scope.

Provided herein are compositions and methods for increasing IL-12 production in a subject in need thereof. Also provided herein are compositions and methods for decreasing IL-12 production in a subject in need thereof.

In some aspects, described herein is a composition for increasing IL-12 production, the composition comprising immunoglobulin G (IgG) or a variant thereof or a fragment thereof.

In an embodiment, the composition comprising immunoglobulin G (IgG) or a variant thereof or a fragment thereof increases signaling mediated by interaction between IgG and FcRn.

In an embodiment, the composition comprising immunoglobulin G (IgG) or a variant thereof or a fragment thereof increases an immune response against an antigen.

In an embodiment, the IgG may be any isotype of IgG including IgG1, IgG2, IgG3 and/or IgG4.

In an embodiment, the variant IgG comprises a methionine to leucine substitution at position 428 and an asparagine to serine substitution at position 434.

In an embodiment, the composition comprising immunoglobulin G (IgG) or a variant thereof or a fragment thereof further comprises an antigen conjugated to IgG or a variant thereof or a fragment thereof so as to create a multimeric structure which can cross-link FcRn.

In an embodiment, the composition comprising immunoglobulin G (IgG) or a variant thereof or a fragment thereof further comprises an antigen complexed to IgG or a variant thereof or a fragment thereof so as to create a monomeric or multimeric structure which can cross-link FcRn.

In various embodiments, the antigen is a tumor antigen, an endogenous antigen, a cell-associated antigen, an apoptotic body, a microbial antigen, a viral antigen, a parasitic antigen or a combination thereof.

In various embodiments, the antigen is a protein or a proteomimetic thereof, a peptide or a peptidomimetic thereof, a lipid or a combination thereof.

In some embodiments, the IgG or a variant thereof or a fragment thereof is mammalian.

In some embodiments, the IgG or a variant thereof or a fragment thereof is human.

In some aspects, described herein are compositions for decreasing IL-12 production comprising an agent that inhibits signaling mediated by interaction between FcRn and IgG.

In some embodiments, the agent that inhibits signaling mediated by interaction between FcRn and IgG is any one or more of a peptide, protein, small molecule, nucleic acid, aptamer, oligonucleotide, antibody or a combination thereof.

In some embodiments, the nucleic acid agent that inhibits signaling mediated by interaction between FcRn and IgG is a siRNA specific to FcRn.

In some embodiments, the antibody agent that inhibits signaling mediated by interaction between FcRn and IgG is selected from the group consisting of a monoclonal antibody or a fragment thereof, a polyclonal antibody or a fragment thereof, chimeric antibody, humanized antibody and single chain antibody.

In some embodiments, the agent that inhibits signaling mediated by interaction between FcRn and IgG is a bispecific agent comprising binding sites for IgG and FcRn.

In some embodiments, the agent that inhibits signaling mediated by interaction between FcRn and IgG is a recombinant Fc portion of IgG or a biologically active portion thereof or a proteo-mimetic thereof.

In some embodiments, the agent that inhibits signaling mediated by interaction between FcRn and IgG is a recombinant Fc portion of IgG or a biologically active portion thereof or a proteo-mimetic thereof, wherein the Fc portion of IgG or a biologically active portion thereof is mammalian.

In some embodiments, the agent that inhibits signaling mediated by interaction between FcRn and IgG is a recombinant Fc portion of IgG or a biologically active portion thereof or a proteo-mimetic thereof, wherein the Fc portion of IgG or a biologically active portion thereof is human.

Also described are methods for modulating the interaction between FcRn and IgG. The method comprises comprising contacting a cell with an agent that binds FcRn and/or IgG and modulates binding of FcRn to IgG.

In some embodiments, the agent use in the method for modulating the interaction between FcRn and IgG, increases signaling mediated by interaction of FcRn and IgG.

In some embodiments, the agent for use in the method modulating the interaction between FcRn and IgG, decreases signaling mediated by interaction of FcRn and IgG.

In some embodiments, the agent for use in the method modulating the interaction between FcRn and IgG comprises binding sites specific for IgG and FcRn.

In some embodiments, the agent for use in the method modulating the interaction between FcRn and IgG comprises binding sites specific for IgG and FcRn.

In some embodiments, the agent for use in the method modulating the interaction between FcRn and IgG comprises binding sites specific for Fc portion of IgG.

In some embodiments, the agent for use in the method modulating the interaction between FcRn and IgG comprises a bispecific polypeptide agent comprising binding sites specific for IgG and FcRn.

In some embodiments, the bispecific polypeptide agent for use in the method modulating the interaction between FcRn and IgG comprises an antibody or antigen binding portion thereof that specifically binds FcRn and an antibody or antigen binding portion thereof that specifically binds IgG.

Also provided herein are methods for treating, inhibiting, preventing metastasis of or preventing relapse of cancer in a subject in need thereof comprising. The methods comprise providing a composition comprising immunoglobulin G (IgG) or a variant thereof or a fragment thereof and administering an effective amount of the composition to the subject so as to treat, inhibit, prevent metastasis or prevent relapse of cancer in the subject.

In some embodiments, the composition for use in the methods for treating, inhibiting, preventing metastasis of or preventing relapse of cancer in a subject in need thereof increases signaling mediated by interaction of IgG and FcRn.

In some embodiments, the composition for use in the methods for treating, inhibiting, preventing metastasis of or preventing relapse of cancer in a subject in need thereof increases an immune response against the antigen.

In some embodiments, the composition for use in the methods for treating, inhibiting, preventing metastasis of or preventing relapse of cancer in a subject in need thereof comprises a variant IgG having a methionine to leucine substitution at position 428 and an asparagine to serine substitution at position 434.

In some embodiments, the composition comprising immunoglobulin G (IgG) or a variant thereof or a fragment thereof for treating, inhibiting, preventing metastasis of or preventing relapse of cancer in a subject in need thereof further comprises an antigen. In some embodiments, the antigen is conjugated to the IgG or a variant thereof or a fragment thereof. In some embodiments, the antigen is complexed with the IgG or a variant thereof or a fragment thereof.

Also provided herein are methods for treating, inhibiting or reducing the severity of infectious diseases in a subject in need thereof. The methods comprise providing a composition comprising immunoglobulin G (IgG) or a variant thereof or a fragment thereof and administering an effective amount of the composition to the subject so as to treat, inhibit or reduce the severity of infectious diseases in the subject.

In some embodiments, the composition for use in the methods for treating, inhibiting or reducing the severity of infectious diseases in a subject in need thereof increases signaling mediated by interaction of IgG and FcRn.

In some embodiments, the composition for use in the methods for treating, inhibiting or reducing the severity of infectious diseases in a subject in need thereof increases an immune response against the antigen.

In some embodiments, the composition for use in the methods for treating, inhibiting or reducing the severity of infectious diseases in a subject in need thereof comprises a variant IgG having a methionine to leucine substitution at position 428 and an asparagine to serine substitution at position 434.

In some embodiments, the composition comprising immunoglobulin G (IgG) or a variant thereof or a fragment thereof for treating, inhibiting or reducing the severity of infectious diseases in a subject in need thereof further comprises an antigen. In some embodiments, the antigen is conjugated to the IgG or a variant thereof or a fragment thereof. In some embodiments, the antigen is complexed with the IgG or a variant thereof or a fragment thereof.

In various embodiments of the methods, the antigen is a tumor antigen, an endogenous antigen, a cell-associated antigen, an apoptotic body, a microbial antigen, a viral antigen, a parasitic antigen or a combination thereof.

Also provided are methods for treating, inhibiting or reducing the severity of autoimmune diseases in a subject in need thereof. The methods comprise providing a composition comprising an agent that inhibits signaling mediated by interaction between FcRn and IgG and administering an effective amount of the composition to the subject so as to treat, inhibit or reduce the severity of autoimmune diseases in the subject.

In some embodiments, the agent for use in the methods for treating, inhibiting or reducing the severity of autoimmune diseases in a subject in need thereof reduces or inhibits production of IL-12.

In some embodiments, the agent for use in the methods for treating, inhibiting or reducing the severity of autoimmune diseases in a subject in need thereof is any one or more of a peptide, protein, small molecule, nucleic acid, aptamer, oligonucleotide, antibody or a combination thereof.

In some embodiments, the nucleic acid agent for use in the methods for treating, inhibiting or reducing the severity of autoimmune diseases in a subject in need thereof is siRNA specific to FcRn.

In some embodiments, the antibody agent for use in the methods for treating, inhibiting or reducing the severity of autoimmune diseases in a subject in need thereof is selected from the group consisting of a monoclonal antibody or a fragment thereof, a polyclonal antibody or a fragment thereof, chimeric antibody, humanized antibody and single chain antibody.

In some embodiments, the agent for use in the methods for treating, inhibiting or reducing the severity of autoimmune diseases in a subject in need thereof is a bispecific agent comprising binding sites for IgG and FcRn.

In some embodiments, the agent for use in the methods for treating, inhibiting or reducing the severity of autoimmune diseases in a subject in need thereof the agent is a recombinant Fc portion of IgG or a biologically active portion thereof or a proteo-mimetic thereof.

Further provided herein is method for determining the efficacy of treatment in a subject in need thereof. The method includes providing a sample from a subject, wherein the subject has been administered an effective amount of a composition comprising immunoglobulin G (IgG) or a variant thereof or a fragment thereof and assaying the levels of any one or more of IL-12, IL-2, TNF-α, IFN-γ, GM-CSF, IL-3, granzyme B, Tbet or a combination thereof in the sample. In one embodiment, the treatment is efficacious if the levels of any one or more of IL-12, IL-2, TNF-α, IFN-γ, GM-CSF, IL-3, granzyme B, Tbet or a combination thereof in the sample from the subject is higher relative to the levels in a reference sample. In another embodiment the treatment is not efficacious if the levels of any one or more of IL-12, IL-2, TNF-α, IFN-γ, GM-CSF, IL-3, granzyme B, Tbet or a combination thereof in the sample from the subject is lower relative to the levels in a reference sample. In an embodiment, the subject has cancer or an infectious disease. In some embodiments, the sample is blood, plasma or tissue.

Also provided herein is a method for determining the efficacy of treatment in a subject in need thereof. The method includes providing a sample from a subject, wherein the subject has been administered a composition comprising an agent that inhibits signaling mediated by interaction between FcRn and IgG and assaying the levels of any one or more of IL-12, IL-2, TNF-α, IFN-γ, GM-CSF, IL-3, granzyme B, Tbet or a combination thereof in the sample. In an embodiment, the treatment is efficacious if the levels of any one or more of IL-12, IL-2, TNF-α, IFN-γ, GM-CSF, IL-3, granzyme B, Tbet or a combination thereof in the sample from the subject is lower relative to the levels in a reference sample. In another embodiment, the treatment is not efficacious if the levels of any one or more of IL-12, IL-2, TNF-α, IFN-γ, GM-CSF, IL-3, granzyme B, Tbet or a combination thereof in the sample from the subject is higher relative to the levels in a reference sample. In an embodiment, the subject has an autoimmune disease. In some embodiments, the sample is blood, plasma or tissue.

BRIEF DESCRIPTION OF FIGURES

This patent or application file contains at least one drawing executed in color. Copies of this patent or patent application publication with color drawings will be provided by the Office upon request and payment of the necessary fee.

Exemplary embodiments are illustrated in the referenced figures. It is intended that the embodiments and figures disclosed herein are to be considered illustrative rather than restrictive.

(FIG. 1A) Large intestine (LI) tumor incidence at 5 months of age and representative tumor histology in $Apc^{Min/+}$ and $Apc^{Min/+}$ $Fcgrt^{-/-}$ mice. Scale bar=100 µm. (FIG. 1B) Tumor incidence in WT and $Fcgrt^{-/-}$ littermates treated with 8 doses of azoxymethane (AOM). (FIG. 1C) Tumor incidence in AOM/DSS-treated WT and $Fcgrt^{-/-}$ littermates. (FIG. 1D) Tumor incidence and maximum tumor diameter in WT and $Fcgrt^{-/-}$ littermates in each of four independent experiments with n≥3 mice per group per experiment. (FIG. 1E) Percent survival of WT and $Fcgrt^{-/-}$ littermates treated with AOM/DSS. Significance was assessed by Log rank test. (FIG. 1F) Richness indices of microbiota associated with the distal LI of untreated 8-week old WT and $Fcgrt^{-/-}$ littermates, as revealed by T-RFLP analysis. n=3-5 mice per group. (FIG. 1G) Abundance of specific microbial species in the distal LI of untreated 7-week old WT and $Fcgrt^{-/-}$ littermates as assessed by qPCR. n=9 mice per group. Representative results of two (1A, 1B, 1E) or four (1D) independent experiments each with n=4-10 mice per group. All data represent mean±s.e.m. *p≤0.05, p≤0.01, *p≤0.005.

(FIG. 2A) Frequency of CD8+ T cells in the lamina propria lymphocyte (LPL) fraction of tumor and adjacent LI tissue in WT and $Fcgrt^{-/-}$ littermates (upper panels) following AOM/DSS treatment. Cytotoxic potential of cells within the CD3+CD8+ gate was assessed by intracellular staining for granzyme B (middle panels) or surface staining of LAMP1 (lower panels). (FIG. 2B) Mean CD8+ T cell frequency and cytotoxic potential in WT and Fcgrt$^{-/-}$ mice, as assessed by flow cytometry, in each of three independent experiments. (FIG. 2C) Cytokine secretion of sorted effector CD8+ CD44+CD62L- cells from the LP of tumor and adjacent tissue of AOM/DSS treated WT and Fcgrt$^{-/-}$ mice following 24 h restimulation with anti-CD3 and anti-CD28. (FIG. 2D) Tumor incidence and tumor load (sum of the diameters of all tumors) in recipient mice adoptively transferred with CD8+ T cells from WT or Fcgrt$^{-/-}$ AOM/DSS-treated donors. Significance was assessed by Mann-Whitney test. Representative results of three independent experiments with n≥4 mice per group per experiment. All data represent mean±s.e.m. NS=not significant. ND=not detected. *p≤0.05, p≤0.01, *p≤0.005.

(FIG. 3A) Tumor antigen-specific IgG in the serum or MLN and LI homogenates of AOM/DSS treated WT or Fcgrt$^{-/-}$ mice. ELISA plates coated with lysates from tumor epithelium were probed with dilutions of serum or tissue homogenates from tumor bearing mice. (FIG. 3B) Transcript profiles of sorted CD8-CD11b+ and CD8+CD11b- DC subsets isolated from the indicated tissue compartment of AOM/DSS-treated WT and Fcgrt$^{-/-}$ littermates. (FIG. 3C) Tumor incidence and survival in Fcgrt$^{-/-}$ recipients adoptively transferred with DC from the MLN and LP of AOM/DSS-treated WT or Fcgrt$^{-/-}$ donors. Endpoint survival was assessed using a Chi-Squared test. (FIG. 3D) CD8+ T cell frequency in the LI LP following transfer of WT DC to AOM/DSS-treated Fcgrt$^{-/-}$ recipients. (FIG. 3E) Tumor incidence and LI LP CD8+ T cell frequency in Itgax$^{cre}$Fcgrt$^{Fl/Fl}$ mice and their littermate Fcgrt$^{Fl/Fl}$ controls upon treatment with AOM/DSS. (FIGS. 3F-3G) Tumor incidence (FIG. 3F) and survival (FIG. 3G) of CD8+ T cell-depleted Fcgrt$^{-/-}$ mice adoptively transferred with WT DC. CD8+ T cells were depleted by chronic i.p. administration of anti-CD8 antibody (or isotype control). Representative results of three (FIGS. 3B-3E) or two (FIG. 3A, 3F) independent experiments with n=3-6 mice per group per experiment. All data represent mean±s.e.m. NS=not significant. *p≤0.05, p≤0.01, *p≤0.005.

(FIG. 4A) Incidence of pulmonary metastatic nodules formed by i.v. administered OVA-expressing B16 melanoma cells (OVA-B16) in WT or Fcgrt$^{-/-}$ mice or Fcgrt$^{-/-}$ mice pre-immunized with WT or Fcgrt$^{-/-}$ DC. (FIG. 4B) Frequency of endogenously occurring OVA-specific CD8+ T cells in WT and Fcgrt$^{-/-}$ metastasis-bearing mice. Left panel demonstrates results from individual animals in a single experiment. Right panel shows the results of three independent experiments each with n=3-6 mice per group. (FIG. 4C) Frequency of pulmonary metastases from mice treated as in (FIG. 4A) and given either a CD8+ T cell-depleting antibody or isotype control. (FIG. 4D) Frequency of pulmonary metastatic nodules and OVA-specific CD8+ T cells in the lungs of Fcgrt$^{Fl/Fl}$ and Itgax$^{cre}$Fcgrt$^{Fl/Fl}$ littermates. (FIG. 4E) Incidence of pulmonary metastatic nodules in WT or Fcgrt$^{-/-}$ mice or Fcgrt$^{-/-}$ mice adoptively transferred with OVA-specific CD8+ T cells primed ex vivo by DC loaded with OVA-containing IgG IC, FcRn non-binding IHH-IgG IC or soluble OVA. (FIG. 4F) Incidence of pulmonary nodules in OVA-B16-treated WT and Fcgrt$^{-/-}$ mice pre-immunized with WT DC loaded ex vivo with OVA-containing IC formed with IgG or enhanced FcRn-binding LS-IgG. Representative results of three (FIG. 4A, 4B, 4D) or two (FIG. 4C, 4E, 4F) independent experiments with n=3-6 mice per group per experiment. All data represent mean±s.e.m. NS=not significant. (*) p=0.09, *p≤0.05, p≤0.01, *p≤0.005.

(FIG. 5A) IgG isotype content of the serum and LI or MLN homogenates in untreated WT and Fcgrt$^{-/-}$ littermates. (FIG. 5B) CD8+ T cell frequency of the LI LPL fraction of untreated WT and Fcgrt$^{-/-}$ littermates in a single experiment (left panels) or across three independent experimental repeats (right panel). (FIG. 5C) Frequency of CD8+ T cells in the LPL fraction of Fcgrt$^{Fl/Fl}$ and Itgax-$^{cre}$Fcgrt$^{Fl/Fl}$ littermates. (FIG. 5D) Cytokine secretion by CD8+ T cells sorted from LI LP of untreated WT and Fcgrt$^{-/-}$ mice following 24 h restimulation with anti-CD3 and anti-CD28. (FIG. 5E) Transcript profiles of CD8+ T cells sorted from LI LP of untreated littermate control mice. (FIG. 5F) Cytokine secretion from 24 h tissue explant cultures of the MLN and LI of untreated WT and Fcgrt$^{-/-}$ mice. (FIG. 5G) Transcript profiles of sorted CD8-CD11b+ DC from the MLN of untreated littermates. Representative results of three independent experiments with n=3-5 mice per group per experiment. All data represent mean±s.e.m. NS=not significant. *p≤0.05, p≤0.01, *p≤0.005.

(FIG. 6A) Induction of IL-12p35 upon ex vivo stimulation of WT CD8-CD11b+ DC from the spleen or MLN with IgG IC or FcRn non-binding IHH-IgG IC for 6 h. (FIG. 6B) IL-12 secretion after 24 h IgG IC stimulation of CD8-CD11b+ and CD8+CD11b- DC sorted from the MLN of AOM/DSS-treated WT and Fcgrt$^{-/-}$ mice. (FIG. 6C) Phosphorylation of STAT-1 and nuclear translocation of IRF-1 and NF-κB p65 upon IgG IC stimulation of DC isolated from WT or Fcgrt$^{-/-}$ mice. (FIG. 6D) IL-12 transcript production by WT or Stat-1$^{-/-}$ CD8-CD11b+ DC following stimulation with IgG or IHH-IgG IC for 6 h. (FIG. 6E) Binding of IRF-1 and NF-kB p65 to the promoters of IL-12p35 and IL-12p40 upon stimulation of WT or Fcgrt$^{-/-}$ DC with IgG IC or IHH-IgG IC for 4 h. (FIG. 6F) Tumor incidence in mice adoptively transferred with WT DC and treated with a neutralizing anti-IL-12 antibody or isotype control. Representative results of three (FIGS. 6A-6E) or one (FIG. 6F) independent experiments with n=3-7 mice per group per experiment. All data represent mean±s.e.m. *p≤0.05, p≤0.01, *p≤0.005.

(FIG. 7A) Double immunohistochemical staining of FcRn+CD11c+ DC in the stroma of CRC (upper panels) and CRC-adjacent normal LI (lower panels). FcRn=brown, CD11c=red. Scale bar left panels=100 μm. Scale bar right panels=20 μm. (FIG. 7B) Colocalization of FcRn+ DC and CD8+ T cells in stroma of CRC (upper panels) and CRC-adjacent normal LI (lower panels). Arrowheads indicate areas of colocalization. (FIG. 7C) Kaplan Meier survival curves of 183 patients with high (≥10 per core) and low (≤10 per core) tumor infiltration by CD11c+ FcRn+ cells. (FIG. 7D) Incidence of tumors in chimeric mice treated with AOM/DSS. WT recipients were reconstituted with WT bone marrow. Fcgrt$^{-/-}$ recipients were reconstituted with Fcgrt$^{-/-}$, WT or hFCGRT-hB2M-mFcgrt$^{-/-}$ bone marrow. Representative result of two independent experiments with n=4-5 mice per group per experiment. (FIG. 7E) hIL-12p35 and hIL-12p40 transcript expression in hMoDC upon stimulation with FcRn-binding (IgG IC) or FcRn non-binding (IHH-IgG IC) immune complexes. (FIG. 7F) Nuclear translocation of IRF-1 and phosphorylation of STAT-1 in hMoDC upon stimulation with IgG IC or IHH-IgG IC. Data in panels FIGS. 7A-7B are representative of a total of 50 matched CRC and adjacent normal LI pairs. Data in panels FIGS. 7E-7F are representative of six donors processed in pairs in each of three independent experiments. All data represent mean±s.e.m. *p≤0.05, p≤0.01, *p≤0.005.

(FIG. 8A) Histological classification of adenomas present in the large intestine (LI) of Apc$^{Min/+}$ and Apc$^{Min/+}$ Fcgrt$^{-/-}$ mice assessed at 5 months of age. (FIG. 8B) Frequency of adenomas in the small intestine (SI) of Apc$^{Mn/+}$ and Apc$^{Mn/+}$ Fcgrt$^{-/-}$ mice. n=4-6 mice per group in each of two independent experiments. (FIG. 8C) Maximum tumor diameter measured in WT and Fcgrt$^{-/-}$ mice treated with eight weekly doses of azoxymethane (AOM) in one representative experiment with n≥3 mice per group. (FIG. 8D) Details of the azoxymethane/dextran sodium sulfate (AOM/DSS) treatment used for the induction of inflammation-associated colorectal cancer. Mice were treated with a single 10 mg/kg dose of AOM via i.p. injection (Day-7). Seven days later (Day 0), mice were given 1.5% DSS in their drinking water for a period of seven days. DSS was withdrawn and mice were allowed to drink regular water for 14 days (Day 7-21). The cycle of one week on DSS (Day 21-28) and two weeks on regular water (Day 28-42) was repeated once. Mice were sacrificed on Day 42. (FIG. 8E) Representative histology of the tumors present in both WT and Fcgrt$^{-/-}$ mice showing severe dysplasia and invasion (arrows) through the lamina propria in a lesion from an Fcgrt$^{-/-}$ mouse. Scale bar=100 μm. (FIG. 8F) Weight curves during the first 20 days of treatment of mice undergoing AOM/DSS regimen. Mice were weighed every 1-2 days. Data are representative of two independent experiments with n=5 mice per group per experiment. (FIG. 8G) Richness indices of microbiota found in the feces of untreated 8-week old WT and Fcgrt$^{-/-}$ littermates, as revealed by T-RFLP analysis. n=3-5 mice per group. (FIG. 8H) Richness indices of microbiota found associated with the distal LI or feces of untreated 2-week old WT and Fcgrt$^{-/-}$ littermates, as revealed by T-RFLP analysis. n=4-9 mice per group. (FIG. 8I) Multidimensional scaling (MDS) plots demonstrating microbial community composition in each of the indicated tissue compartments of untreated 8-week old and 2-week old WT and Fcgrt$^{-/-}$ mice as assessed by T-RFLP. ANOSIM analysis of Bray Curtis similarity matrices revealed no significant differences between WT and Fcgrt$^{-/-}$ mice for any age or tissue compartment. (FIG. 8J) ANOSIM results for analysis of microbial differences between tissue compartments within each age group, regardless of genotype. (FIG. 8K) Abundance of specific microbial species associated with the feces of untreated 7-week old WT and Fcgrt$^{-/-}$ mice as assessed by qPCR. Values from each species have been normalized to total bacteria (16S). Each dot represents an individual animal. n=9 mice per group. All data represent mean±s.e.m. ND=none detected. *p≤0.05.

(FIG. 9A) Flow cytometric analysis of the frequency of CD4$^+$ I cells, NK cells (NK1.1) or macrophages (F4/80) in the lamina propria lymphocyte (LPL) fraction of tumor and adjacent LI tissue in WI and Fcgrt$^{-/-}$ mice following AOM/DSS treatment. (FIG. 9B) Absolute number of CD8$^+$ I cells isolated from the LP tissue of the adjacent, tumor or untreated (baseline) LI in AOM/DSS-treated mice as assessed by flow cytometric staining and acquisition of fixed volumes of sample. (FIGS. 9C-9D) Flow cytometric analysis of the frequency of CD8$^+$ I cells in the lamina propria (LP) fraction of tumor-adjacent LI tissue in untreated Apc$^{Min/+}$ and Apc-$^{Min/+}$ Fcgrt$^{-/-}$ mice (FIG. 9C) and in AOM-treated WI and Fcgrt$^{-/-}$ littermates (FIG. 9D). Representative results from one of three experiments with n=3 mice per group per experiment. (FIG. 9E) Flow cytometric analysis of the extent of CD8$^+$ I cell proliferation (Ki-67) and apoptosis (Annexin V) in the LP fraction of tumor and adjacent LI tissue in WI and Fcgrt$^{-/-}$ littermates following AOM/DSS treatment. Plots depict cells within the CD3$^+$CD8$^+$ gate of cells. Representative plots from three independent experiments with n=3 mice per group per experiment. (FIG. 9F) Phenotype of CD8$^+$ I cells in the indicated tissue compartment of WI and Fcgrt$^-$/− littermates treated with AOM/DSS. Representative plots from three independent experiments with n=3-4 mice per group per experiment. (FIG. 9G) Survival rates of AOM/DSS-treated recipient mice adoptively transferred with CD4$^+$ I cells taken from the MLN and LI LP of AOM/DSS-treated WI and Fcgrt$^{-/-}$ donors. Representative results from one of two independent experiments with n=4 mice per group per experiment. Significance of survival curves was assessed by Log rank test. All data represent mean±s.e.m. *p≤0.05.

(FIG. 10A) Isotype distribution of tumor antigen-specific IgG in the serum or LI homogenates of AOM/DSS treated WT or Fcgrt$^{-/-}$ mice. ELISA plates coated with lysates from tumor epithelium were probed with dilutions of serum or tissue homogenates from tumor bearing mice and developed with isotype-specific secondary antibodies. (FIG. 10B) Immunoblots demonstrating tumor antigen-specific IgG in the serum and LI homogenates of each of eight AOM/DSS treated mice. IgG-depleted lysates prepared from tumor intestinal epithelial cells (IEC) or non-tumor control IEC were resolved under reducing conditions by SDS-PAGE and membranes of the transferred lysates were probed with serum or LI homogenates from tumor bearing mice. Representative blots from two independent experiments with n=4 mice per group per experiment. $2^{nd}$ Ab=anti-mouse IgG-HRP. (FIG. 10C) Fold increase above baseline values in serum anti-phosphatidylserine (α-PS) and anti-cardiolipin (α-CL) IgG content in WT and Fcgrt$^{-/-}$ littermates. (FIG. 10D) IgG isotype content of the serum, LI homogenates and MLN homogenates in AOM/DSS-treated WT and Fcgrt$^{-/-}$ mice. (FIG. 10E) Flow cytometric analysis of the frequency of CD8$^+$ versus CD11b$^+$ DC (top row, gated on CD11c$^+$ cells) and characterization of the CD11c$^+$CD8$^-$CD11b$^+$ DC (bottom four rows) in the mucosal tissues of AOM/DSS-treated WT and Fcgrt$^{-/-}$ littermates. (FIGS. 10E-10H) Whole tissue cytokine transcript profiles of the indicated tissue compartments from AOM/DSS-treated WT and Fcgrt$^{-/-}$ littermates (FIG. 10F), untreated Apc$^{Min/+}$ and Apc$^{Min/+}$ Fcgrt$^{-/-}$ littermates (FIG. 10G) and AOM-treated WT and Fcgrt$^{-/-}$ littermates (FIG. 10H). Representative results from 2-4 independent experiments with n=3-6 mice per group per experiment. Data represent mean±s.e.m. (FIG. 10I) Purity (top panel) and subset distribution (bottom panel) of the DC transferred in FIGS. 3C, 3F. (FIG. 10J) Frequency of congenic (CD45.2) WT or Fcgrt$^{-/-}$ DC in the MLN and LI LP of recipient (CD45.1) mice 3 days and 7 days after intraperitoneal transfer. Recipient mice injected with PBS are shown as controls. (FIG. 10K) Ex vivo antigen cross-presentation with DC isolated from the MLN of the indicated AOM/DSS-treated DC recipient mice and loaded with IC containing FcRn-binding (IgG) immune complex (IC), non-FcRn binding (IHH-IgG) IC or soluble antigen (OVA) and cocultured with OT-I CD8$^+$ T cells. (FIG. 10L) Relative Fcgrt transcript levels as assessed by qPCR in DC (CD11c), macrophages (CD11b) and hepatocytes purified from WT, Fcgrt$^{-/-}$, Fcgrt$^{Fl/Fl}$ or Itgax$^{cre}$Fcgrt$^{Fl/Fl}$ mice. Data are representative of two independent experiments with n=3-5 mice per group per experiment. All data represent mean±s.e.m. *p 5 0.05, p 5 0.01, *p 5 0.005.

(FIG. 11A) CD8$^+$ T cell frequency in the lungs of untreated WT or Fcgrt$^{-/-}$ mice. (FIGS. 11B-11C) Tumor-specific anti-OVA IgG in the lung homogenates (FIG. 11B) or serum (FIG. 11C) of WT and Fcgrt$^{-/-}$ littermates bearing lung metastases. Lungs were harvested 2 weeks after i.v. injection of 0.5×10$^6$ OVA-expressing B16 melanoma cells (OVA-B16). Anti-OVA IgG content was evaluated by ELISA and normalized to protein content of the homogenates for (FIG. 11B). (FIG. 11D) Frequency of OVA-specific IgG producing B cells in the lymph nodes (LN) or spleens of OVA-B16 lung metastasis-bearing WT and Fcgrt$^{-/-}$ mice. B cells were isolated and cultured on OVA-coated ELISpot plates for 24 h. (FIG. 11E) Representative lobes from immunized or non-immunized mice injected with OVA-B16 cells. (FIG. 11F) Ex vivo antigen cross-presentation using DC stimulated with immune complexes (IC) formed with NIP-OVA and either FcRn-binding (IgG IC), non-FcRn binding (IHH-IgG IC) or enhanced FcRn-binding (LS-IgG IC) immunoglobulin and cocultured with OT-I CD8$^+$ T cells. All data are representative of the results of one of three independent experiments with n=3-6 mice per group per experiment. Data represent mean±s.e.m. NS=not significant. *p≤0.05.

(FIG. 12A) Frequency (upper panels) and effector status (lower panels) of adoptively transferred congenic CD8$^+$ I cells (CD45.1) in the LI LP and MLN of untreated WI and Fcgrt$^{-/-}$ recipient mice (CD45.2). 1×10$^6$ CD8$^+$ I cells were transferred into recipient mice via i.v. injection and their distribution and phenotype was assessed 10 days later. (FIG. 12B) Frequency of adoptively transferred congenic CD8$^+$ I cells from WI and Fcgrt$^{-/-}$ donor mice (CD45.2) in the LI LP and MLN of untreated recipient mice (CD45.1) 7 days after transfer. (FIG. 12C) Whole tissue transcript profiles of the LI from untreated WI and Fcgrt$^{-/-}$ littermates (left panel) or Fcgrt$^{Fl/Fl}$ and Itgax$^{cre}$Fcgrt$^{Fl/Fl}$ littermates (right panel), as assessed by qPCR. (FIG. 12D) Cytokine secretion by CD4$^+$ I cells isolated via magnetic sorting from the LI LP of untreated WI and Fcgrt$^{-/-}$ mice and restimulated for 24 h with anti-CD3 (αCD3) and anti-CD28 (αCD28). (FIG. 12E) CD4$^+$ I cell frequency in the LI LP of untreated WI and Fcgrt$^{-/-}$ mice (left panels) or Fcgrt$^{Fl/Fl}$ and Itgax$^{cre}$Fcgrt$^{Fl/Fl}$ mice (right panels). Representative results from three independent experiments with n=3-5 mice per group per experiment. Data represent mean±s.e.m. *p≤0.05, p≤0.01, *p≤0.005.

(FIG. 13B) Binding of IRF-1 to the IL-12p35 promoter upon stimulation of Myd88$^{-/-}$CD8$^-$CD11b$^+$ DC with IgG IC or IHH-IgG IC for 4 h. (FIG. 13C) Ex vivo antigen cross-presentation in the presence of an IL-12 neutralizing antibody (αIL-12) or isotype control. DC were stimulated with IgG IC or IHH-IgG IC and co-cultured with OT-I CD8$^+$ T cells. Representative data shown from one of three independent experiments. Data represent mean±s.e.m. *p≤0.05, **p≤0.01.

(FIG. 14A) Double immunohistochemical staining of FcRn$^+$CD11c$^+$ DC in the stroma of CRC-bearing (upper panels) and tumor-adjacent normal (lower panels) LI of additional cases of human CRC. See also FIG. 7A. Scale bar left panels=100 μm. Scale bar right panels=20 μm. (FIG. 14B) Colocalization of FcRn$^+$ DC and CD8$^+$ T cells in the stroma of CRC-bearing (upper panels) and tumor-adjacent normal (lower panels) LI of additional cases of human CRC. Arrowheads indicate areas of colocalization. See also FIG. 7B. Data in FIGS. 14A-14B are representative of 50 matched normal LI and CRC assessed. (FIG. 14C) Correlation between the number of FcRn$^+$CD11c$^+$ DC and CD8$^+$ T cells in the stroma of normal LI adjacent to CRC. Significance was assessed using Spearman's rank correlation. (FIG. 14D) Multivariable analysis of the impact of colonic LP CD11c$^+$FcRn$^+$ cells on patient survival in 183 human CRC patients. An increasing number of CD11+FcRn+ cells has a positive effect on patient survival (univariate analysis p=0.0333) and this effect is maintained in multivariable analysis with the indicated parameters. See also FIG. 7C. (FIG. 14E) CD8$^+$ T cell frequency in the tumor LP of chimeric mice treated with AOM/DSS. WT recipients were reconstituted with bone marrow from WT donors. Fcgrt$^{-/-}$ recipients were reconstituted with bone marrow from either Fcgrt$^{-/-}$, WT or hFCGRT-hB2M-mFcgrt$^{-/-}$ donors. Representative results from one of two independent experiments with n=4-5 mice per group per experiment. (FIG. 14F) Phenotype of human monocyte derived DC (hMoDC) as determined by flow cytometric analysis. Shaded curve represents isotype control. (FIG. 14G) Expression of FcRn in hMoDC, as assessed by the same antibody utilized for immunohistochemical staining of CRC cases. (FIG. 14H) Densitometric analysis of Western blots of hMoDC stimulated with IgG IC depicted in FIG. 7F. Data in panels FIGS. 14F-14H are representative of six donors processed in pairs in each of three independent experiments. All data represent mean±s.e.m.

(FIG. 15A) Whole colon cytokine transcript levels from flagellin immunized hFCGRT/hB2M/mFcgrt-/- chimeric mice treated with either DVN24 or an isotype control before and during the onset of DSS colitis. (FIG. 15B) Cytokine transcript levels from CD8+ T cells isolated from the lamina propria of hFCGRT/hB2M/mFcgrt-/- BM chimeras treated with DVN24 or an isotype control or mFcgrt-/- BM chimeras treated with PBS during DSS colitis. *P<0.05. **P<0.01.

DETAILED DESCRIPTION OF THE INVENTION

Figures 1A, 1B, 1C, 1D, 1E, 1F, 1G:
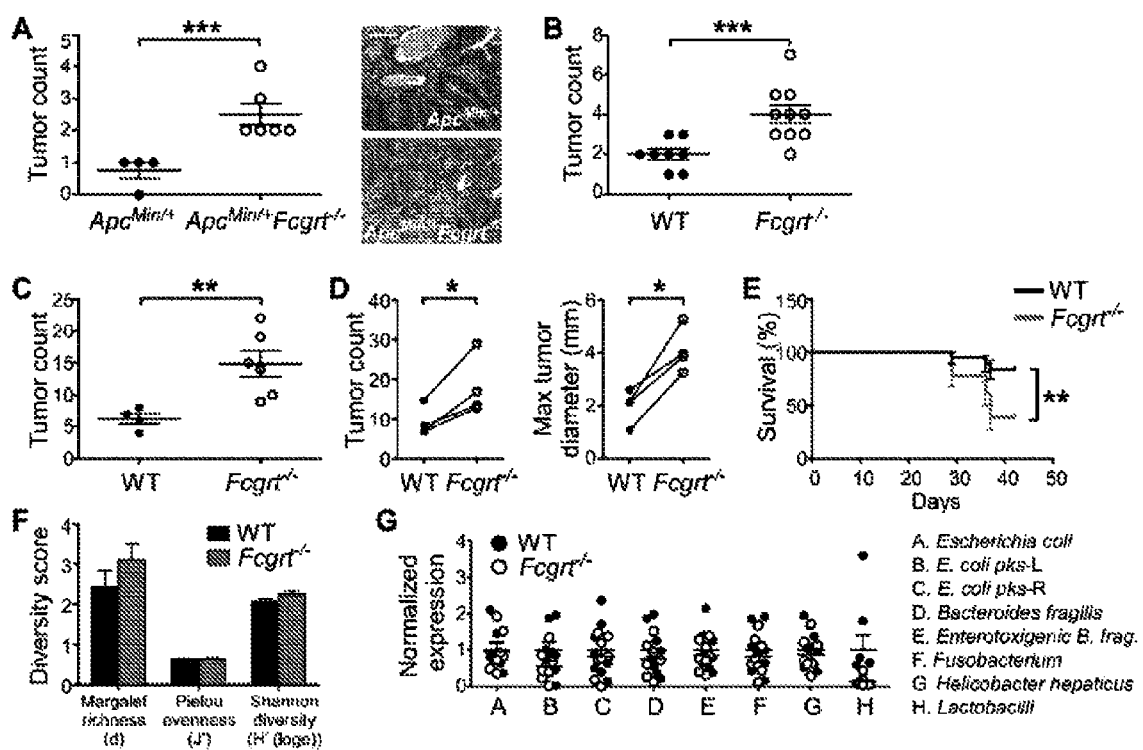
FIGS. 1A-1G depict, in accordance with various embodiments of the present invention that FcRn protects against the development of colorectal cancer through a mechanism independent of intestinal microbiota.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, N.Y. 2001); March, *Advanced Organic Chemistry Reactions, Mechanisms and Structure* 5$^{th}$ ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

As used herein, the term "antibody" refers to an intact immunoglobulin or to a monoclonal or polyclonal antigen-binding fragment with the Fc (crystallizable fragment) region or FcRn binding fragment of the Fc region, referred to herein as the "Fc fragment" or "Fc domain". Antigen-binding fragments may be produced by recombinant DNA techniques or by enzymatic or chemical cleavage of intact antibodies. Antigen-binding fragments include, inter alia, Fab, Fab', F(ab')2, Fv, dAb, and complementarity determining region (CDR) fragments, single-chain antibodies (scFv), single domain antibodies, chimeric antibodies, diabodies, tetrabodies and other multimerized scFv moieties and polypeptides that contain at least a portion of an immunoglobulin that is sufficient to confer specific antigen binding to the polypeptide. The Fc domain includes portions of two heavy chains contributing to two or three classes of the antibody. The Fc domain may be produced by recombinant DNA techniques or by enzymatic (e.g. papain cleavage) or via chemical cleavage of intact antibodies. The amino acid sequence of the Fc domain can be modified to increase its affinity with FcRn to enable better induction of secreted proteins such as IL-12, interferon-gamma, IL-2, tumor necrosis factor, granulocyte macrophage colony stimulating factor, IL-3 and granzyme B or transcription factors such as t-bet or modified to decrease its affinity for FcRn and the induction of these aforementioned cytokines and transcription factors.

The term "antibody fragment," as used herein, refer to a protein fragment that comprises only a portion of an intact antibody, generally including an antigen binding site of the intact antibody and thus retaining the ability to bind antigen. Examples of antibody fragments encompassed by the present definition include: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v) the Fv fragment having the VL and VH domains of a single arm of an antibody; (vi) the dAb fragment (Ward et al., Nature 341, 544-546 (1989)) which consists of a VH domain; (vii) isolated CDR regions; (viii) F(ab')2 fragments, a bivalent fragment including two Fab' fragments linked by a disulphide bridge at the hinge region; (ix) single chain antibody molecules (e.g., single chain Fv; scFv) (Bird et al., Science 242:423-426 (1988); and Huston et al., PNAS (USA) 85:5879-5883 (1988)); (x) "diabodies" with two antigen binding sites, comprising a heavy chain variable domain (VH) connected to a light chain variable domain (VL) in the same polypeptide chain (see, e.g., EP 404,097; WO 93/11161; and Hollinger et al., Proc. Natl. Acad. Sci. USA, 90:6444-6448 (1993)); (xi) "linear antibodies" comprising a pair of tandem Fd segments (VH-CH1-VH-CH1) which, together with complementary light chain polypeptides, form a pair of antigen binding regions (Zapata et al. Protein Eng. 8(10):1057-1062 (1995); and U.S. Pat. No. 5,641,870).

As described herein, an "antigen" is a molecule that is bound by a binding site on a polypeptide agent, such as an antibody or antibody fragment thereof. Typically, antigens are bound by antibody ligands and are capable of raising an antibody response in vivo. An antigen can be a polypeptide, protein, nucleic acid, lipid or other molecule. In the case of conventional antibodies and fragments thereof, the antibody binding site as defined by the variable loops (L1, L2, L3 and H1, H2, H3) is capable of binding to the antigen. The term "antigenic determinant" refers to an epitope on the antigen recognized by an antigen-binding molecule, and more particularly, by the antigen-binding site of said molecule.

An "Fv" fragment is an antibody fragment which contains a complete antigen recognition and binding site. This region consists of a dimer of one heavy and one light chain variable domain in tight association, which can be covalent in nature, for example in scFv. It is in this configuration that the three CDRs of each variable domain interact to define an antigen binding site on the surface of the VH-VL dimer Collectively, the six CDRs or a subset thereof confer antigen binding specificity to the antibody. However, even a single variable domain (or half of an Fv comprising only three CDRs specific for an antigen) has the ability to recognize and bind antigen, although usually at a lower affinity than the entire binding site.

A "cancer" or "tumor" as used herein refers to an uncontrolled growth of cells which interferes with the normal functioning of the bodily organs and systems. A subject that has a cancer or a tumor is a subject having objectively measurable neoplastic cells present in the subject's body. Included in this definition are benign and malignant cancers, as well as dormant tumors or micrometastases. Cancers which migrate from their original location and seed vital organs can eventually lead to the death of the subject through the functional deterioration of the affected organs. Hematopoietic cancers, such as leukemia, are able to outcompete the normal hemopoietic compartments in a subject, thereby leading to hemopoietic failure (in the form of anemia, thrombocytopenia and neutropenia) ultimately causing death.

As used herein, "complexed" refers to the non-covalent interactions between any two molecules. Examples include but are not limited to complexes formed between and an antigen and an antibody (for example, IgG or a variant thereof or a fragment thereof) wherein the antigen and the antibody interact via non-covalent bonds. Examples of non-covalent interactions include but are not limited to electrostatic interactions (for example, ionic interactions, hydrogen bonds, halogen bonds), van der Waals forces (dipole-dipole, dipole-induced, London dispersion forces), pi-effects (pi-pi interactions, cation-pi, anion-pi, polar-pi) and/or hydrophobic interactions. In various embodiments, the complex between the IgG or a fragment thereof or a variant thereof and the antigen forms multimeric structures that can cross-link/bind with FcRn.

As used herein, "conjugated" refers to covalent interactions between any two molecules. Examples include but are not limited to fusion proteins comprising an antigen and an antibody (for example, IgG or a variant thereof or a fragment thereof) or any other antigen-antibody complex that may be covalently linked. In various embodiments, the conjugation between the IgG or a fragment thereof or a variant thereof forms and the antigen forms monomeric or multimeric structures that can cross-link/bind with FcRn.

As used herein, an "epitope" can be formed both from contiguous amino acids, or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5, about 9, or about 8-10 amino acids in a unique spatial conformation. An "epitope" includes the unit of structure conventionally bound by an immunoglobulin VH/VL pair. Epitopes define the minimum binding site for an antibody, and thus represent the target of specificity of an antibody. In the case of a single domain antibody, an epitope represents the unit of structure bound by a variable domain in isolation. The terms "antigenic determinant" and "epitope" can also be used interchangeably herein. In various embodiments, an epitope may be protein, peptide, nucleic acid, lipid, other molecules or combinations thereof.

As used herein, an "immune response" being modulated refers to a response by a cell of the immune system, such as a B cell, T cell (CD4 or CD8), regulatory T cell, antigen-presenting cell, dendritic cell, monocyte, macrophage, NKT cell, NK cell, basophil, eosinophil, or neutrophil, to a stimulus. In some embodiments, the response is specific for a particular antigen (an "antigen-specific response"), and refers to a response by a CD4 T cell, CD8 T cell, or B cell via their antigen-specific receptor. In some embodiments, an immune response is a T cell response, such as a CD4+ response or a CD8+ response. Such responses by these cells can include, for example, cytotoxicity, proliferation, cytokine or chemokine production, trafficking, or phagocytosis, and can be dependent on the nature of the immune cell undergoing the response. In some embodiments of the compositions and methods described herein, an immune response being modulated is T-cell tolerance.

By "metastasis" is meant the spread of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is a sequential process, contingent on tumor cells breaking off from the primary tumor, traveling through the bloodstream, and stopping at a distant site. At the new site, the cells establish a blood supply and can grow to form a life-threatening mass. Both stimulatory and inhibitory molecular pathways within the tumor cell regulate this behavior, and interactions between the tumor cell and host cells in the distant site are also significant.

The term "monoclonal antibody" as used herein refers to an antibody obtained from a population of substantially homogeneous antibodies, i.e., the individual antibodies comprising the population are identical except for possible naturally occurring mutations that can be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. The modifier "monoclonal" is not to be construed as requiring production of the antibody by any particular method. For example, the monoclonal antibodies to be used in accordance with the invention can be made by the hybridoma method first described by Kohler et al., Nature 256:495 (1975), or can be made by recombinant DNA methods (see, e.g., U.S. Pat. No. 4,816, 567). The "monoclonal antibodies" can also be isolated from phage antibody libraries using the techniques described in Clackson et al., Nature 352:624-628 (1991) or Marks et al., J. Mol. Biol. 222:581-597 (1991), for example.

As used herein, "selectively binds" or "specifically binds" refers to the ability of an antibody or antibody fragment thereof described herein to bind to a target, such as a molecule present on the cell-surface, with a KD 10-5 M (10000 nM) or less, e.g., $10^{-6}$ M, $10^{-7}$ M, $10^{-8}$ M, $10^{-9}$ M, $10^{-10}$ M, $10^{-11}$ M, $10^{-12}$ M, or less. Specific binding can be influenced by, for example, the affinity and avidity of the polypeptide agent and the concentration of polypeptide agent. The person of ordinary skill in the art can determine appropriate conditions under which the polypeptide agents described herein selectively bind the targets using any suitable methods, such as titration of a polypeptide agent in a suitable cell binding assay.

"Subject" or "individual" or "animal" or "patient" or "mammal," is meant any subject, particularly a mammalian subject, for whom diagnosis, prognosis, or therapy is desired. In some embodiments, the subject has cancer. In some embodiments, the subject had cancer at some point in the subject's lifetime. In various embodiments, the subject's cancer is in remission, is recurrent or is non-recurrent. In some embodiments the subject has an infectious disease. In some embodiments, the subject has an autoimmune disease.

"Mammal" as used herein refers to any member of the class Mammalia, including, without limitation, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and so on. In certain embodiments, the mammal is a human subject. The term does not denote a particular age or sex. Thus, adult and newborn subjects, as well as fetuses, whether male or female, are intended to be included within the scope of this term As used herein, the term "target" refers to a biological molecule (e.g., peptide, polypeptide, protein, lipid, carbohydrate) to which a polypeptide domain which has a binding site can selectively bind. The target can be, for example, an intracellular target (e.g., an intracellular protein target) or a cell surface target (e.g., a membrane protein, a receptor protein). Preferably, a target is a cell surface target, such as a cell surface protein.

As used herein, the terms "treat," "treatment" "treating," or "amelioration" refer to therapeutic treatments, wherein the object is to reverse, alleviate, ameliorate, inhibit, slow down or stop the progression or severity of a condition associated with, a disease or disorder. The term "treating" includes reducing or alleviating at least one adverse effect or symptom of a condition, disease or disorder, such as an autoimmune disease, a chronic infection or a cancer. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. The term "treatment" of a disease also includes providing relief from the symptoms or side-effects of the disease (including palliative treatment).

A number of tumor antigens have been identified that are associated with specific cancers. As used herein, the terms "tumor antigen" and "cancer antigen" are used interchangeably to refer to antigens which are differentially expressed by neoplastic cells and can thereby be exploited in order to target neoplastic cells. Cancer antigens are antigens which can potentially stimulate apparently tumor-specific immune responses. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), fusion proteins resulting from internal deletions or chromosomal translocations. Still other cancer antigens can be encoded by viral genes such as those carried on RNA and DNA tumor viruses. Many tumor antigens have been defined in terms of multiple solid tumors: MAGE 1, 2, & 3, defined by immunity; MART-1/Melan-A, gp100, carcinoembryonic antigen (CEA), HER-2, mucins (i.e., MUC-1), prostate-specific antigen (PSA), and prostatic acid phosphatase (PAP). In addition, viral proteins such as hepatitis B (HBV), Epstein-Barr (EBV), and human papilloma (HPV) have been shown to be important in the development of hepatocellular carcinoma, lymphoma, and cervical cancer, respectively. However, due to the immunosuppression of patients diagnosed with cancer, the immune systems of these patients often fail to respond to the tumor antigens.

"Endogenous antigens" as used herein refers to antigens that have been generated within the body. They include xenogenic (heterologus), autologus, idiotypic or allogenic antigens and autoantigens.

FcRn is a neonatal Fc receptor. It is similar in structure to major histocompatibility complex I (MHC I). Human FcRn is very stringent regarding its specificity and binds human Fc, but not mouse, rat, bovine, or sheep Fc. The FcRn can bind to two sites of the IgG (Sanchez et al., 1999; Schuck et al., 1999; West A. P. and Bjorkman, 2000). Although mouse IgGs do not bind efficiently to human FcRn and therefore have a short half-life in humans (Frodin et al., 1990), mouse IgG as an immune complex is capable of binding human FcRn and inducing signaling. In contrast, mouse FcRn binds IgG from every species analyzed (Ober et al., 2001).

Most serum proteins have a short serum half-life (about 1-2 days). However, two types of serum proteins, namely albumin and antibodies of the IgG class, have greatly extended serum half-lives. For example, most subclasses of IgG have a half-life of about 10-20 days in humans. The Fc region of IgG is required for this extension of half-life. Thus, truncated IgG polypeptides carrying only the Fc region, and potentially also proteins carrying a short FcRn binding peptide sequence (FcBP) (Sockolosky et al. Proc Natl Acad Sci USA 2012, 109, 16095-100), also show such extended serum half-life. Moreover, when the Fc region is fused with a fusion partner (e.g., a biologically active protein), this Fc fusion protein shows an extended serum half-life due to its interaction with FcRn.

The mechanism by which FcRn extends the serum half-life of IgG and IgG Fc fusion proteins is well established (Ghetie and Ward, 2000, 2002; Roopenian and Akilesh, 2007). FcRn is localized in the endosomal compartments of many cell types, including vascular endothelium. Serum proteins are constantly being endocytosed and directed to the early endosomal vesicles. FcRn is harbored primarily in this acidified vesicle. In this acidified environment, the Fc region binds FcRn, and the IgG/FcRn complex is then recycled either apically or basolaterally back to the plasma membrane, whereupon exposure to the neutral pH 7.2 extracellular environment results in its release into the circulation. In contrast, other endocytosed proteins that do not bind FcRn are not rescued, and thus continue through the endosomal route to catabolic elimination, resulting in their short half-life. The biochemical mechanism by which the Fc region of IgG binds FcRn in an acidic environment is well understood. The CH2-CH3-hinge region of the Fc region contains solvent exposed histidine residues, which when protonated, engage residues on FcRn with sufficient affinity to permit IgG to exploit the FcRn recycling pathway to escape catabolic elimination.

As described herein, the inventors discovered that cross-linking FcRn on dendritic cells with antigen/antibody immune complexes, which function as ligands for FcRn, directly leads to the production of IL-12 by these cells, as well as interferon-gamma, tumor necrosis factor, granzyme B and t-bet by CD8+ T cells. FcRn functions as a signaling molecule by organizing the necessary proteins, including elements of the cytoskeleton and mitogen activated protein kinases (MAPK) to directly promote the transcription of IL-12 through factors such as IRF-1 and NFκB. As demonstrated herein, FcRn-mediated upregulation of IL-12p35 is dependent upon ERK and calmodulin but not cytoskeletal rearrangements. The production of FcRn-dependent IL-12 is essential for the generation of CD8+ effector T cells and their effector function through factors such interferon-gamma, tumor necrosis factor, granzyme B and t-bet. Such effector T cells mediate anti-infectious immunity and mediate tumor immune-surveillance and eradication. If IL-12 is neutralized, the FcRn-mediated effects on CD8+ effector T cell functions that are associated with tumor eradication are lost.

In a homologous manner, blockade of FcRn function is associated with decreased FcRn-mediated signal transduction and thereby decreased production of IL-12 and related factors which is associated with protection from autoimmune disorders as shown in animal models of inflammatory bowel disease. While not wishing to be bound by any particular mechanism or theory, the aspects and embodiments described herein are based on the finding that binding of FcRn to antigen/antibody immune complexes regulates IL-12 production by dendritic cells, which can be manipulated for therapeutic purposes. Since IL-12 is a master regulator of immune responses associated with tumor and anti-infectious immunity on the one hand, and inappropriate inflammation on the other, it is desirable to increase IL-12 for anti-tumor immunity and decrease IL-12 for anti-inflammatory purposes. Accordingly, described herein are compositions and methods for increasing/enhancing/up-regulating IL-12 production for treating cancer and infectious diseases and compositions and methods for decreasing IL-12 production for treating autoimmune disorders.

Compositions and Methods for Treating Cancer and/or Infectious Diseases

In some aspects, the compositions and methods described herein up-regulate/increase/enhance production of IL-12 by increasing/enhancing interaction between IgG and FcRn (for example, in response to an antigen bound to the IgG, or due to mutations in IgG that increase the binding between IgG and FcRn). The interactions between IgG and FcRn yield signals that result in production of IL-12 by dendritic cells. The compositions provided herein comprise IgG or a variant thereof or a fragment thereof so as to increase IL-12 production. As described herein, the compositions can further comprise antigens, including but not limited to, tumor antigens, bacterial antigens, viral antigens, parasitic antigens or combinations thereof, as to increase IL-12 production. As used herein, "IgG" can refer to any isotype of IgG including IgG1, IgG2, IgG3 and/or IgG4.

In some embodiments, the variants of IgG in the compositions and methods described herein are functional, non-naturally occurring variants of IgG that enhance binding between IgG and FcRn, so as to increase IL-12 production. "Functional variants of IgG," as used herein, useful with the compositions and methods described herein include molecules comprising mutations, such as insertions, deletions and truncations in full-length IgG, or the constant region of an IgG molecule, provided such molecules retain the ability to bind to FcRn and increase IL-12 production. One example of such a variant includes, but is not limited to, an IgG comprising a methionine to leucine substitution at position 428 and an asparagine to serine substitution at position 434 according to the Kabat numbering scheme. Another example of a functional IgG variant useful with the compositions and methods described herein is an engineered variant of human IgG1 comprising mutations of Met 252, Ser254, Thr256, His433, and Asn434 to Tyr252, Thr254, Glu256, Lys433, and Phe434, as described in "Engineering the Fc region of immunoglobulin G to modulate in vivo antibody levels," Nature Biotechnology, 2005 (23):10, pp 1283-88, the contents of which are herein incorporated by reference in their entireties. Other functional IgG variants useful with the compositions and methods described herein are described in U.S. Pat. No. 8,188,231, U.S. Pat. No. 8,802,823, US2011025068, US20060235208, WO2012106578 A1, the contents of each of which are herein incorporated by reference in their entireties.

For example, functional IgG variants can comprise amino acid modifications at Fc positions 230, 240, 244, 245, 247, 262, 263, 266, 273, 275, 299, 302, 313, 323, 325, 328, and 332, wherein the numbering of the residues in the Fc region is that of the EU index as in Kabat. In some embodiments, functional IgG variants can comprise at least one amino acid substitution in the Fc region at a position selected from the group consisting of 221, 222, 223, 224, 225, 227, 228, 230, 231, 232, 233, 234, 235, 236, 237, 238, 239, 240, 241, 243, 244, 245, 246, 247, 249, 255, 258, 260, 262, 263, 264, 265, 266, 267, 268, 269, 270, 271, 272, 273, 274, 275, 276, 278, 280, 281, 282, 283, 284, 285, 286, 288, 290, 291, 292, 293, 294, 295, 296, 297, 298, 299, 300, 301, 302, 303, 304, 305, 313, 317, 318, 320, 322, 323, 324, 325, 326, 327, 328, 329, 330, 331, 332, 333, 334, 335, 336, and 337, wherein the numbering of the residues in the Fc region is that of the EU index as in Kabat.

In some embodiments, said IgG variants comprise at least one substitution selected from the group consisting of D221K, D221Y, K222E, K222Y, T223E, T223K, H224E, H224Y, T225E, T225K, T225W, P227E, P227G, P227K, P227Y, P228E, P228G, P228K, P228Y, P230A, P230E, P230G, P230Y, A231E, A231G, A231K, A231P, A231Y, P232E, P232G, P232K, P232Y, E233A, E233D, E233F, E233G, E233H, E233I, E233K, E233L, E233M, E233N, E233Q, E233R, E233S, E233T, E233V, E233W, E233Y, L234A, L234D, L234E, L234F, L234G, L234H, L234I, L234K, L234M, L234N, L234P, L234Q, L234R, L234S, L234T, L234V, L234W, L234Y, L235A, L235D, L235E, L235F, L235G, L235H, L235I, L235K, L235M, L235N, L235P, L235Q, L235R, L235S, L235T, L235V, L235W, L235Y, G236A, G236D, G236E, G236F, G236H, G236I, G236K, G236L, G236M, G236N, G236P, G236Q, G236R, G236S, G236T, G236V, G236W, G236Y, G237D, G237E, G237F, G237H, G237I, G237K, G237L, G237M, G237N, G237P, G237Q, G237R, G237S, G237T, G237V, G237W, G237Y, P238D, P238E, P238F, P238G, P238H, P238I, P238K, P238L, P238M, P238N, P238Q, P238R, P238S, P238T, P238V, P238W, P239Y, S239D, S239E, S239F, S239G, S239H, S239I, S239K, S239L, S239M, S239N, S239P, S239Q, S239R, S239T, S239V, S239W, S239Y, V240A, V240I, V240M, V241T, F241D, F241E, F241L, F241R, F241S, F241W, F241Y, F243E, F243H, F243L, F243Q, F243R, F243W, F243Y, P244H, P245A, K246D, K246E, K246H, K246Y, P247G, P247V, D249H, D249Q, D249Y, R255E, R255Y, E258H, E258S, E258Y, T260D, T260E, T260H, T260Y, V262A, V262E, V262F, V262I, V262T, V263A, V263I, V263M, V263T, V264A, V264D, V264E, V264F, V264G, V264H, V264I, V264K, V264L, V264M, V264N, V264P, V264A, V264R, V264S, V264T, V264W, V264Y, D265F, D265G, D265H, D265I, D265K, D265L, D265M, D265N, D265P, D265Q, D265R, D265S, D265T, D265V, D265W, D265Y, V266A, V266I, V266M, V266T, S267D, S267E, S267F, S267H, S267I, S267K, S267L, S267M, S267N, S267P, S267Q, S267R, S267T, S267V, S267W, S267Y, H268D, H268E, H268F, H268G, H268I, H268K, H268L, H268M, H268P, H268Q, H268R, H268T, H268V, H268W, E269F, E269G, E269H, E269I, E269K, E269L, E269M, E269N, E269P, E269R, E269S, E269T, E269V, E269W, E269Y, D270F, D270G, D270H, D270I, D270L, D270M, D270P, D270Q, D270R, D270S, D270T, D270W, D270Y, P271A, P271D, P271E, P271F, P271G, P271H, P271I, P271K, P271L, P271M, P271N, P271Q, P271R, P271S, P271T, P271V, P271W, P271Y, E272D, E272F, E272G, E272H, E272I, E272K, E272L, E272M, E272P, E272R, E272S, E272T, E272V, E272W, E272Y, V273I, K274D, K274E, K274F, K274G, K274H, K274I, K274L, K274M, Kb 274N, K274P, K274R, K274T, K274V, K274W, K274Y, F275L, F275W, N276D, N276E, N276F, N276G, N276H, N276I, N276L, N276M, N276P, N276R, N276S, N276T, N276V, N276W, N276Y, Y278D, Y278E, Y278G, Y278H, Y278I, Y278K, Y278L, Y278M, Y278N, Y278P, Y278Q, Y278R, Y278S, Y278T, Y278V, Y278W, D280G, D280K, D280L, D280P, D280W, G281D, G281E, G281K, G281N, G281P, G281Q, G281Y, V282E, V282G, V282K, V282P, V282Y, E283G, E283H, E283K, E283L, E283P, E283R, E283Y, V284D, V284E, V284L, V284N, V284Q, V284T, V284Y, H285D, H285E, H285K, H285Q, H285W, H285Y, N286E, N286G, N286P, N286Y, K288D, K288E, K288Y, K290D, K290H, K290L, K290N, K290W, P291D, P291E, P291G, P291H, P291I, P291Q, P291T, R292D, R292E, R292T, R292Y, E293F, E293G, E293H, E293I, E293L, E293M, E293N, E293P, E293R, E293S, E293T, E293V, E293W, E293Y, E294F, E294G, E294H, E294I, E294K, E294L, E294M, E294P, E294R, E294S, E294T, E294V, E294W, E294Y, Q295D, Q295E, Q295F, Q295G, Q295H, Q295I, Q295M, Q295N, Q295P, Q295R, Q295S, Q295T, Q295V, Q295W, Q295Y, Y296A, Y296D, Y296E, Y296G, Y296H, Y296I, Y296K, Y296L, Y296M, Y296N, Y296Q, Y296R, Y296S, Y296T, Y296V, N297D, N297E, N297F, N297G, N297H, N297I, N297K, N297L, N297M, N297P, N297Q, N297R, N297S, N297T, N297V, N297W, N297Y, S298D, S298E, S298F, S298H, S298I, S298K, S298M, S298N, S298Q, S298R, S298T, S298W, S298Y, T299A, T299D, T299E, T299F, T299G, T299H, T299I, T299K, T299L, T299M, T299N, T299P, T299Q, T299R, T299S, T299V, T299W, T299Y, Y300A, Y300D, Y300E, Y300G, Y300H, Y300K, Y300M, Y300N, Y300P, Y300Q, Y300R, Y300S, Y300T, Y300V, Y300W, R301D, R301E, R301H, R301Y, V302I, V303D, V303E, V303Y, S304D, S304H, S304L, S304N, S304T, V305E, V305T, V305Y, W313F, K317E, K317Q, E318H, E318L, E318Q, E318R, E318Y, K320D, K320F, K320G, K320H, K320I, K320L, K320N, K320P, K320S, K320T, K320Y, K320W, K320Y, K322D, K322F, K322G, K322H, K322I, K322P, K322S, K322T, K322V, K322W, K322Y, V323I, S324D, S324F, S324G, S324H, S324I, S324L, S324M, S324P, S324R, S324T, S324V, S324W, S324Y, N325A, N325D, N325E, N325F, N325G, N325H, N325I, N325K, N325L, N325M, N325P, N325Q, N325R, N325S, N325T, N325V, N325W, N325Y, K326I, K326L, K326P, K326T, A327D, A327E, A327F, A327H, A327I, A327K, A327L, A327M, A327N, A327P, A327R, A327S, A327T, A327V, A327W, A327Y, L328A, L328D, L328E, L328F, L328G, L328H, L328I, L328K, L328M, L328N, L328P, L328Q, L328R, L328S, L328T, L328V, L328W, L328Y, P329D, P329E, P329F, P329G, P329H, P329I, P329K, P329L, P329M, P329N, P329Q, P329R, P329S, P329T, P329V, P329W, P329Y, A330E, A330F, A330G, A330H, A330I, A330L, A330M, A330N, A330P, A330R, A330S, A330T, A330V, A330W, A330Y, P331D, P331F, P331H, P331I, P331L, P331M, P331Q, P331R, P331T, P331V, P331W, P331Y, I332A, I332D, I332E, I332F, I332H, I332K, I332L, I332M, I332N, I332P, I332Q, I332R, I332S, I332T, I332V, I332W, I332Y, E333F, E333H, E333I, E333L, E333M, E333P, E333T, E333Y, K334F, K334I, K334L, K334P, K334T, T335D, T335F, T335G, T335H, T335I, T335L, T335M, T335N, T335P, T335R, T335S, T335V, T335W, T335Y, I336E, I336K, I336Y, S337E, S337H, and S337N, wherein the numbering of the residues in the Fc region is that of the EU index as in Kabat.

In some embodiments, said IgG variants comprise any one of the following combinations of substitutions: S239D/A330L/I332E, S239D/A330Y/I332E/L234I, S239D/A330Y/I332E/V266I, S239D/D265F/N297D/I332E, S239D/D265H/N297D/I332E, S239D/D265I/N297D/I332E, S239D/D265L/N297D/I332E, S239D/D265T/N297D/I332E, S239D/D265Y/N297D/I332E, S239D/E272I/A330L/I332E, S239D/E272I/I332E, S239D/E272K/A330L/I332E, S239D/E272K/I332E, S239D/E272S/A330L/I332E, S239D/E272S/I332E, S239D/E272Y/A330L/I332E, S239D/E272Y/I332E, S239D/F241S/F243H/V262T/V264T/N297D/A330Y/I332E, S239D/H268D, S239D/H268E, S239D/I332D, S239D/I332E, S239D/I332E/A327D, S239D/I332E/A330I, S239D/I332E/A330Y, S239D/I332E/E272H, S239D/I332E/E272R, S239D/I332E/E283H, S239D/I332E/E283L, S239D/I332E/G236A, S239D/I332E/G236S, S239D/I332E/H268D, S239D/I332E/H268E, S239D/I332E/K246H, S239D/I332E/R255Y, S239D/I332E/S267E, S239D/I332E/V264I, S239D/I332E/V264I/A330L, S239D/I332E/V264I/S298A, S239D/I332E/V284D, S239D/I332E/V284E, S239D/I332E/V284E, S239D/I332N, S239D/I332D, S239D/K274E/A330L/I332, S239D/K274E/I332E, S239D/K326E/A330L/I332, S239D/K326E/A330Y/I332E, S239D/K326E/I332E, S239D/K326T/A330Y/I332E, S239D/K326T/I332E, S239D/N297D/A330Y/I332E, S239D/N297D/I332E, S239D/N297D/K326E/I332E, S239D/S267E/A330L/I332E, S239D/S267E/I332E, S239D/S298A/K326E/I332E, S239D/S298A/K326T/I332E, S239D/V240I/A330Y/I332E, S239D/V264T/A330Y/I332E, S239D/Y278T/A330L/I332E, S239D/Y278T/I332E, S239E, S239E/D265G, S239E/D265N, S239E/D265Q, S239E/I332D, S239E/I332E, S239E/I332N, S239E/I332Q, S239E/N297D/I332E, S239E/V264I/A330Y/I332E, S239E/V264I/I332E, S239E/V264I/S298A/A330Y/I332E, S239F, S239G, S239H, S239I, S239K, S239L, S239M, S239N, S239N/I332D, S239N/I332E, S239N/I332E/A330L, S239N/I332E/A330Y, S239N/I332N, S239N/I332Q, S239P, S239Q, S239Q/I332D, S239Q/I332E, S239Q/I332N, S239Q/I332Q, S239Q/V264I/I332E, S239R, S239T, S239V, S239W, S239Y, V240A, V240I, V240I/V266I, V240M, V240T, F241D, F241E, F241E/F243Q/V262T/V264E/I332E, F241E/F243Q/V262T/V264E, F241E/F243R/V262E/V264R/I332E, F241E/F243R/V262E/V264R, F241E/F243Y/V262T/V264R/I332E, F241E/F243Y/V262T/V264R, F241L, F241L/F243L/V262I/V264I, F241L/V262I, F241R/F243Y/V262T/V264R/I332E, F241R/F243Y/V262T/V264R, F241W, F241W/F243W, F241W/F243W/V262A/V264A, F241Y, F241Y/F243Y/V262T/V264T/N297D/I332E, F241Y/F243Y/V262T/V264T, F243E, F243L, F243L/V262I/V264W, F243L/V264I, F243W, P244H, P244H/P245A/P247V, P245A, K246D, K246E, K246H, K246Y, P247G, P247V, D249H, D249Q, D249Y, R255E, R255Y, E258H, E258S, E258Y, T260D, T260E, T260H, T260Y, V262E, V262F, V263A, V263I, V263M, V263T, V264A, V264D, V264E, V264E/N297D/I332E, V264F, V264G, V264H, V264I, V264I/A330L/I332E, V264I/A330Y/I332E, V264I/I332E, V264K, V264L, V264M, V264N, V264P, V264Q, V264R, V264S, V264T, V264W, V264Y, D265F, D265F/N297E/I332E, D265G, D265H, D265I, D265K, D265L, D265M, D265N, D265P, D265Q, D265R, D265S, D265T, D265V, D265W, D265Y, D265Y/N297D/I332E, D265Y/N297D/T299L/I332E, V266A, V266I, V266M, V266T, S267D, S267E, S267E, S267E/A327D, S267E/P331D, S267E/S324I, S267E/V282G, S267F, S267H, S267I, S267K, S267L, S267L/A327S, S267M, S267N, S267P, S267Q, S267Q/A327S, S267R, S267T, S267V, S267W, S267Y, H268D, H268E, H268F, H268G, H268I, H268K, H268L, H268M, H268P, H268Q, H268R, H268T, H268V, H268W, E269F, E269G, E269H, E269I, E269K, E269L, E269M, E269N, E269P, E269R, E269S, E269T, E269V, E269W, E269Y, D270F, D270G, D270H, D270I, D270L, D270M, D270P, D270Q, D270R, D270S, D270T, D270W, D270Y, P271A, P271D, P271E, P271F, P271G, P271H, P271I, P271K, P271L, P271M, P271N, P271Q, P271R, P271S, P271T, P271V, P271W, P271Y, E272D, E272F, E272G, E272H, E272I, E272K, E272L, E272M, E272P, E272R, E272S, E272T, E272V, E272W, E272Y, V273I, K274D, K274E, K274F, K274G, K274H, K274I, K274L, K274M, K274N, K274P, K274R, K274T, K274V, K274W, K274Y, F275L, F275W, N276D, N276E, N276F, N276G, N276H, N276I, N276L, N276M, N276P, N276R, N276S, N276T, N276V, N276W, N276Y, Y278D, Y278E, Y278G, Y278H, Y278I, Y278K, Y278L, Y278M, Y278N, Y278P, Y278Q, Y278R, Y278S, Y278T, Y278V, Y278W, Y278W, Y278W/E283R/V302I, Y278W/V302I, D280G, D280K, D280L, D280P, D280W, G281D, G281D/V282G, G281E, G281K, G281N, G281P, G281Q, G281Y, V282E, V282G, V282G/P331D, V282K, V282P, V282Y, E283G, E283H, E283K, E283L, E283P, E283R, E283R/V302I/Y278W/E283R, E283Y, V284D, V284E, V284L, V284N, V284Q, V284T, V284Y, H285D, H285E, H285K, H285Q, H285W, H285Y, N286E, N286G, N286P, N286Y, K288D, K288E, K288Y, K290D, K290H, K290L, K290N, K290W, P291D, P291E, P291G, P291H, P291I, P291Q, P291T, R292D, R292E, R292T, R292Y, E293F, E293G, E293H, E293I, E293L, E293M, E293N, E293P, E293R, E293S, E293T, E293V, E293W, E293Y, E294F, E294G, E294H, E294I, E294K, E294L, E294M, E294P, E294R, E294S, E294T, E294V, E294W, E294Y, Q295D, Q295E, Q295F, Q295G, Q295H, Q295I, Q295M, Q295N, Q295P, Q295R, Q295S, Q295T, Q295V, Q295W, Q295Y, Y296A, Y296D, Y296E, Y296G, Y296I, Y296K, Y296L, Y296M, Y296N, Y296Q, Y296R, Y296S, Y296T, Y296V, N297D, N297D/I332E, N297D/I332E/A330Y, N297D/I332E/S239D/A330L, N297D/I332E/S239D/D265V, N297D/I332E/S298A/A330Y, N297D/I332E/T299E, N297D/I332E/T299F, N297D/I332E/T299H, N297D/I332E/T299I, N297D/I332E/T299L, N297D/I332E/T299V, N297D/I332E/Y296D, N297D/I332E/Y296E, N297D/I332E/Y296H, N297D/I332E/Y296N, N297D/I332E/Y296Q, N297D/I332E/Y296T, N297E/I332E, N297F, N297G, N297H, N297I, N297K, N297L, N297M, N297P, N297Q, N297R, N297S, N297S/I332E, N297T, N297V, N297W, N297Y, S298A/I332E, S298A/K326E, S298A/K326E/K334L, S298A/K334L, S298D, S298E, S298F, S298H, S298I, S298K, S298M, S298N, S298Q, S298R, S298T, S298W, S298Y, T299A, T299D, T299E, T299F, T299G, T299H, T299I, T299K, T299L, T299M, T299N, T299P, T299Q, T299R, T299S, T299V, T299W, T299Y, Y300A, Y300D, Y300E, Y300G, Y300H, Y300K, Y300M, Y300N, Y300P, Y300Q, Y300R, Y300S, Y300T, Y300V, Y300W, R301D, R301E, R301H, R301Y, V302I, V303D, V303E, V303Y, S304D, S304H, S304L, S304N, S304T, V305E, V305T, V305Y, W313F, K317E, K317Q, E318H, E318L, E318Q, E318R, E318Y, K320D, K320F, K320G, K320H, K320I, K320L, K320N, K320P, K320S, K320T, K320V, K320W, K320Y, K322D, K322F, K322G, K322H, K322I, K322P, K322S, K322T, K322V, K322W, K322Y, V323I, S324D, S324F, S324G, S324H, S324I, S324I/A327D, S324L, S324M, S324P, S324R, S324T, S324V, S324W, S324Y, N325A, N325D, N325E, N325F, N325G, N325H, N325I, N325K, N325L, N325M, N325P, N325Q, N325R, N325S, N325T, N325V, N325W, N325Y, K326I, K326L, K326P, K326T, A327D, A327E, A327F, A327H, A327I, A327K, A327L, A327M, A327N, A327P, A327R, A327S, A327T, A327V, A327W, A327Y, L328A, L328D, L328D/I332E, L328E, L328E/I332E, L328F, L328G, L328H, L328H/I332E, L328I/L328I, L328E, L328I/I332E, L328K, L328M, L328M/I332E, L328N, L328N/I332E, L328P, L328A, L328Q/I332E, L328Q/I332E, L328R, L328S, L328T, L328T/I332E, L328V, L328V/I332E, L328W, L328Y, P329D, P329E, P329F, P329G, P329H, P329I, P329K, P329L, P329M, P329N, P329Q, P329R, P329S, P329T, P329V, P329W, P329Y, A330E, A330F, A330G, A330H, A330I, A330L, A330L/I332E, A330M, A330N, A330P, A330R, A330S, A330T, A330V, A330W, A330Y, A330Y/I332E, P331D, P331F, P331H, P331I, P331L, P331M, P331Q, P331R, P331T, P331V, P331W, P331Y, I332A, I332D, I332E, I332E/G281D, I332E/H268D, I332E/H268E, I332E/S239D/S298A, I332E/S239N/S298A, I332E/V264I/S298A, I332E/V284E, I332F, I332H, I332K, I332L, I332M, I332N, I332P, I332Q, I332R, I332S, I332T, I332V, I332W, I332Y, E333F, E333H, E333I, E333L, E333M, E333P, E333T, E333Y, K334F, K334I, K334P, K334T, T335F, T335G, T335H, T335I, T335L, T335M, T335N, T335P, T335R, T335S, T335V, T335W, T335Y, I336E, I336K, I336Y, S337E, S337H, and S337N, wherein the numbering of the residues in the Fc region is that of the EU index as in Kabat.

The IgG or Fc variants described herein are defined according to the amino acid modifications that compose them. Thus, for example, I332E is an Fc variant with the substitution I332E relative to the parent Fc polypeptide. Likewise, S239D/A330L/I332E (also referred to as 239D/330L/332E) defines an Fc variant with the substitutions S239D, A330L, and I332E (239D, 330L, and 332E) relative to the parent Fc polypeptide. It is noted that the order in which substitutions are provided is arbitrary, that is to say that, for example, S239D/A330L/I332E is the same Fc variant as S239D/I332E/A330L, and so on. For all positions discussed in the present invention, numbering is according to the EU index or EU numbering scheme (Kabat et al., 1991, Sequences of Proteins of Immunological Interest, 5th Ed., United States Public Health Service, National Institutes of Health, Bethesda, incorporated by reference). The EU index or EU index as in Kabat refers to the numbering of the EU antibody (Edelman et al., 1969, Proc Natl Acad Sci USA 63:78-85, incorporated by reference).

Any other IgG mutants/variants (such as insertions, deletions, substitutions, truncations or frameshift mutations) that increase the interactions between the IgG and FcRn and increase IL-12 production can be used in the compositions and methods described herein. In some embodiments, the IgG or a variant thereof or a fragment thereof is mammalian. In some embodiments, the IgG or a variant thereof or a fragment thereof is human. In some embodiments, the IgG or a variant thereof or a fragment thereof is recombinant.

In some embodiments, fragments of IgG that can be used in the compositions described herein include wild type Fc fragments IgG or mutant Fc fragments of IgG, provided such molecules retain the ability to bind to FcRn and increase IL-12 production.

In some embodiments, the composition comprising IgG or a variant thereof or a fragment thereof comprises the variable region of an FcRn specific antibody or a multimeric form (such as a triabody) of the variable region. In some embodiments, the composition comprising IgG or a variant thereof or a fragment thereof comprises multimerized scFv structures such as tetrabodies.

In some embodiments, the compositions comprising IgG or a variant thereof or a fragment thereof further comprise an antigen that can be conjugated to or complexed with the IgG or a variant thereof or a fragment thereof. The interaction between FcRn and the IgG complexed with an antigen or the IgG conjugated to an antigen results in increased production of IL-12 in response to the antigen. In various embodiments, the antigen is a tumor antigen, a microbial antigen, a viral antigen, a parasitic antigen or a combination thereof. In some embodiments, the antigen is a protein or a proteomimetic thereof, a peptide or a peptidomimetic thereof, a lipid or a combination thereof. In some embodiments, a composition in which the IgG or a variant thereof or a fragment thereof is complexed to an antigen, the antigen is non-covalently bound to the IgG or a fragment thereof or a variant thereof. In some embodiments, a composition in which the IgG or a variant thereof or a fragment thereof is conjugated to an antigen, the antigen is covalently bound to the IgG or a fragment thereof or a variant thereof.

As used herein, in various embodiments, IL-12 production is "increased" if IL-12 levels are increased by a statistically significant amount, for example by at least 10%, at least 20%, at least 30%, at least 40%, at least 50%, at least 60%, at least 70%, at least 80%, at least 90%, at least 95%, at least 97%, at least 98%, or more, up to and including at least 100% or more, at least 2-fold, at least 3-fold, at least 4-fold, at least 5-fold, at least 6-fold, at least 7-fold, at least 8-fold, at least 9-fold, at least 10-fold, at least 50-fold, at least 100-fold, or more, in the presence of an agent or stimulus, relative to the absence of such an agent or stimulus. The agent or stimulus can be the binding of FcRn to the IgG or a fragment thereof or a variant thereof so as to increase IL-12 production. In some embodiments, IgG or a fragment thereof or a variant thereof can be complexed or conjugated to an antigen, as described herein.

The compositions described herein are used to treat, inhibit, prevent relapse of and/or prevent metastasis of cancer in a subject in need thereof. The methods for treating, inhibiting, preventing relapse of and/or preventing metastasis of cancer in the subject comprise providing a composition comprising IgG or a variant thereof or a fragment and administering an effective amount of the composition to the subject. In some embodiments, the IgG variant comprises a methionine to leucine substitution at position 428 and an asparagine to serine substitution at position 434 according to the Kabat numbering scheme. The compositions can further comprise an antigen conjugated or complexed with the IgG or a variant thereof or a fragment. In some embodiments, the IgG or a variant thereof or a fragment thereof is mammalian. In some embodiments, the IgG or a variant thereof or a fragment thereof is human. In some embodiments, the IgG or a variant thereof or a fragment thereof is recombinant. In some embodiments, the methods for treating, inhibiting, preventing relapse of and/or preventing metastasis of cancer in the subject further comprise administering to the subject a chemotherapeutic aigggent and/or radiation therapy, concurrently or sequentially with the composition.

Examples of cancer include but are not limited to, carcinoma, lymphoma, blastoma, sarcoma, and leukemia. More particular examples of such cancers include, but are not limited to, basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

In some embodiments described herein, the methods further comprise administering a tumor or cancer antigen to a subject being administered the composition for increasing IgG and FcRn interactions described herein. In exemplary embodiments, tumor-specific antigens that can be conjugated or complexed with IgG or a variant thereof or a fragment thereof include, but are not limited to, any one or more of 4-1BB, 5T4, adenocarcinoma antigen, alpha-fetoprotein, BAFF, B-lymphoma cell, C242 antigen, CA-125, carbonic anhydrase 9 (CA-IX), C-MET, CCR4, CD152, CD19, CD20, CD200, CD22, CD221, CD23 (IgE receptor), CD28, CD30 (TNFRSF8), CD33, CD4, CD40, CD44 v6, CD51, CD52, CD56, CD74, CD80, CEA, CNTO888, CTLA-4, DR5, EGFR, EpCAM, CD3, FAP, fibronectin extra domain-B, folate receptor 1, GD2, GD3 ganglioside, glycoprotein 75, GPNMB, HER2/neu, HGF, human scatter factor receptor kinase, IGF-1 receptor, IGF-I, IgG1, L1-CAM, IL-13, IL-6, insulin-like growth factor I receptor, integrin $\alpha 5\beta 1$, integrin $\alpha v\beta 3$, MORAb-009, MS4A1, MUC1, mucin CanAg, N-glycolylneuraminic acid, NPC-1C, PDGF-R $\alpha$, PDL192, phosphatidylserine, prostatic carcinoma cells, RANKL, RON, ROR1, SCH900105, SDC1, SLAMF7, TAG-72, tenascin C, TGF beta 2, TGF-$\beta$, TRAIL-R1, TRAIL-R2, tumor antigen CTAA16.88, VEGF-A, VEGFR-1, VEGFR2 or vimentin. Other antigens specific for cancer will be apparent to those of skill in the art and can be used in connection with alternate embodiments of the invention.

In some embodiments of the methods described herein, the methods further comprise administering a chemotherapeutic agent to the subject being administered a composition for increasing IgG and FcRn interactions. Non-limiting examples of chemotherapeutic agents can include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaI1 (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE; vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above. In addition, the methods of treatment can further include the use of radiation therapy.

The compositions described herein are also used to treat, inhibit and/or reduce the severity of infectious diseases in a subject in need thereof. The methods for treating, inhibiting and/or reducing the severity of infectious diseases in the subject include providing a composition comprising IgG or a variant thereof or a fragment and administering an effective amount of the composition to the subject. The compositions can further comprise an antigen conjugated or complexed with the IgG or a variant thereof or a fragment, as described herein. In some embodiments, the IgG or a variant thereof or a fragment thereof is mammalian. In some embodiments, the IgG or a variant thereof or a fragment thereof is human. In some embodiments, the IgG or a variant thereof or a fragment thereof is recombinant.

In various embodiments, bacterial antigens can be any antigen present in infectious bacteria and that induce an immune response in a subject. Examples of infectious bacteria include: *Helicobacterpyloris, Borelia burgdorferi, Legionella pneumophilia, Mycobacteria* sps (such as *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus anthracia, corynebacterium diphtheriae, corynebacterium* sp., *Erysipelothrix rhusiopathiae, Clostridium perfringens, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira*, and *Actinomyces israelli*. The compositions and methods described herein are contemplated for use in treating infections with these bacterial agents. Other infectious organisms (such as protists) include: *Plasmodium falciparum* and *Toxoplasma gondii*. The compositions and methods described herein are contemplated for use in treating infections with these agents.

In various embodiments, viral antigens can be any antigens present in infectious viruses and that induce an immune response in a subject. Examples of infectious viruses include: Retroviridae (for example, HIV); Picornaviridae (for example, polio viruses, hepatitis A virus; enteroviruses, human coxsackie viruses, rhinoviruses, echoviruses); Caliciviridae (such as strains that cause gastroenteritis); Togaviridae (for example, equine encephalitis viruses, rubella viruses); Flaviridae (for example, dengue viruses, encephalitis viruses, yellow fever viruses); Coronaviridae (for example, coronaviruses); Rhabdoviridae (for example, vesicular stomatitis viruses, rabies viruses); Filoviridae (for example, ebola viruses); Paramyxoviridae (for example, parainfluenza viruses, mumps virus, measles virus, respiratory syncytial virus); Orthomyxoviridae (for example, influenza viruses); Bungaviridae (for example, Hantaan viruses, bunga viruses, phleboviruses and Nairo viruses); Arena viridae (hemorrhagic fever viruses); Reoviridae (e.g., reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and HSV-2, varicella zoster virus, cytomegalovirus (CMV), herpes viruses); Poxviridae (variola viruses, vaccinia viruses, pox viruses); and Iridoviridae (such as African swine fever virus); and unclassified viruses (for example, the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses). The compositions and methods described herein are contemplated for use in treating infections with these viral agents.

Examples of fungal infections that can be treated with the compositions and methods described herein include but are not limited to: aspergillosis; thrush (caused by *Candida albicans*); cryptococcosis (caused by *Cryptococcus*); and histoplasmosis. Thus, examples of infectious fungi include, but are not limited to, *Cryptococcus neoformans, Histoplasma capsulatum, Coccidioides immitis, Blastomyces dermatitidis, Chlamydia trachomatis, Candida albicans*. The compositions and methods described herein are contemplated for use in treating infections with these fungal agents.

In some embodiments of the aspects described herein, the methods further comprise administering an effective amount of a viral, bacterial, fungal, or parasitic antigen in conjunction with the compositions comprising IgG or a variant thereof or a fragment thereof. Non-limiting examples of suitable viral antigens include: influenza HA, NA, M, NP and NS antigens; HIV p24, pol, gp41 and gp120; Metapneumovirus (hMNV) F and G proteins; Hepatitis C virus (HCV) E1, E2 and core proteins; Dengue virus (DEN1-4) E1, E2 and core proteins; Human Papilloma Virus L1 protein; Epstein Barr Virus gp220/350 and EBNA-3A peptide; Cytomegalovirus (CMV) gB glycoprotein, gH glycoprotein, pp65, IE1 (exon 4) and pp 150; Varicella Zoster virus (VZV) IE62 peptide and glycoprotein E epitopes; Herpes Simplex Virus Glycoprotein D epitopes, among many others. The antigenic polypeptides can correspond to polypeptides of naturally occurring animal or human viral isolates, or can be engineered to incorporate one or more amino acid substitutions as compared to a natural (pathogenic or non-pathogenic) isolate.

Compositions and Methods for Treating Autoimmune Diseases

In some aspects, described herein are compositions for decreasing/down-regulating production of IL-12 by altering or inhibiting interactions between IgG and FcRn. The compositions comprise agents that inhibit (reduce or block) signaling mediated by interaction between FcRn and IgG. Such agents include, but are not limited to, antibodies ("antibodies" includes antigen-binding portions of antibodies such as epitope- or antigen-binding peptides, paratopes, functional CDRs; recombinant antibodies; chimeric antibodies; tribodies; midibodies; or antigen-binding derivatives, analogs, variants, portions, or fragments thereof), protein-binding agents, small molecules, recombinant protein, peptides, aptamers, avimers and protein-binding derivatives, portions or fragments thereof. In some embodiments, the composition comprises agents that inhibit FcRn-mediated downstream signaling such as signaling mediated by interactions between, for example, FcRn and WAVE2, or FcRn and calmodulin.

Antisense oligonucleotides represent another class of agents that are useful in the compositions and methods described herein, particularly as IgG and/or FcRn antagonists. This class of agents and methods for preparing and using them are all well-known in the art, as are ribozyme and miRNA molecules. See, e.g., PCT US2007/024067 for a thorough discussion. Alternatively, an agent that inhibits interactions between IgG and FcRn can, in some embodiments of the compositions and methods described herein, include recombinant Fc or conjugates, or protein or antibody, small interfering RNA specific for or targeted to FcRn mRNA, and antisense RNA that hybridizes with the mRNA of FcRn, for example.

Other agents for use in the compositions and methods described herein that inhibit IgG interaction with FcRn include, for example, antibodies against FcRn, specifically reactive or specifically binding to FcRn. In some embodiments, the antibody is a blocking antibody and can be any of a monoclonal antibody or a fragment thereof, a polyclonal antibody or a fragment thereof, a chimeric antibody, humanized antibody or a single chain antibody. In some embodiments, the agent is a bispecific agent comprising binding sites for IgG and FcRn. In some embodiments, the agent is a recombinant Fc portion of IgG or a biologically active portion thereof or a proteo-mimetic thereof. The Fc portion or a biologically active portion thereof can be mammalian. The Fc portion or a biologically active portion thereof can be human.

As used herein, a "blocking" antibody or an antibody "antagonist" is one which inhibits or reduces the biological activity of the antigen(s) it binds. For example, a IgG/FcRn bispecific blocking or antagonist antibody binds IgG and FcRn and inhibits the ability of IgG and FcRn to induce IL-12 production by dendritic cells. In certain embodiments, the blocking antibodies or antagonist antibodies or portions thereof described herein completely inhibit the interaction between IgG and FcRn. In certain embodiments, the blocking antibodies or antagonist antibodies or portions thereof described herein reduce/decrease the interaction between IgG and FcRn. In an embodiment, the antibody is a monoclonal antibody that specifically binds FcRn. In an embodiment, the monoclonal antibody that specifically binds FcRn is DVN24. In an embodiment, DVN24 is humanized.

Simple binding assays can be used to screen for or detect agents that bind to FcRn or IgG, or disrupt the interaction between a FcRn and IgG. Further, agents that inhibit the FcRn/IgG interaction for use in the compositions and methods described herein, including recombinant FcRn or IgG peptido-mimetics, can be identified by, for example, transfecting cells with expression vectors expressing FcRn or IgG or portions thereof; contacting the cells with an agent; lysing the cells; and characterizing the FcRn/IgG interaction in comparison with cells not contacted with agent. Cells can be characterized using, for example, co-immunoprecipitation.

Another variation of assays to determine binding of a FcRn protein to a IgG protein is through the use of affinity biosensor methods. Such methods can be based on the piezoelectric effect, electrochemistry, or optical methods, such as ellipsometry, optical wave guidance, and surface plasmon resonance (SPR). For example, efficacy of an siRNA on the expression of FcRn or IgG can be monitored using methods known in the art such as quantitative RT-PCR with specific oligonucleotide primers for each gene respectively, or ELISA for FcRn and/or IgG from a sample of peripheral blood. Alternatively, the population of blood cells can be determined by FACS analysis using the markers characteristic of particular populations and subpopulations known in the art or disclosed herein.

In some aspects, provided herein are methods for suppressing an immune response in vivo (for example by decreasing IL-12 production), comprising administering to the subject a therapeutically effective amount of an inhibitor of interaction between FcRn and IgG, or an inhibitor of the generation of its downstream signaling, as described herein. Reducing or inhibiting the interaction between IgG and FcRn is useful for specifically suppressing an immune response in vivo, which can be useful for the treatment of conditions related to immune function including autoimmune disease and transplantation (e.g., bone marrow or organs). The inhibitors that decrease IgG/FcRn interactions can be used alone as a primary therapy or in combination with other therapeutics as a combination therapy to enhance the therapeutic benefits of other medical treatments.

In various embodiments, as used herein, interaction between IgG and FcRn is "decreased" if one or more signaling activities or downstream read-outs of FcRn activity, such as IL-12 production, is reduced by a statistically significant amount, for example by at least 10%, at least 20%, at least 30%, at least 40%, at least 50%, at least 60%, at least 70%, at least 80%, at least 90%, at least 95%, at least 97%, at least 98%, or more, up to and including at least 100% or more, at least 2-fold, at least 3-fold, at least 4-fold, at least 5-fold, at least 6-fold, at least 7-fold, at least 8-fold, at least 9-fold, at least 10-fold, at least 50-fold, at least 100-fold, or more, in the presence of an inhibitor, relative to the absence of such an inhibitor. In various embodiments, the inhibitor alters FcRn/IgG mediated signaling so as to decrease IL-12 production.

In some embodiments of the methods described herein, the subject being administered an inhibitor for decreasing IgG/FcRn interactions is diagnosed with, has, or suffers from an autoimmune disease. Accordingly, provided herein, in some aspects, are methods of treating a subject having or diagnosed with an autoimmune disorder comprising administering an effective amount of an agent for decreasing FcRn/IgG interactions. Also provided herein are methods for inhibiting or reducing the severity of an autoimmune disorder in a subject administering an effective amount of an agent for decreasing FcRn/IgG interactions.

"Autoimmune disease" refers to a class of diseases in which a subject's own antibodies react with host tissue or in which immune effector T cells are autoreactive to endogenous self-peptides and cause destruction of tissue. Thus an immune response is mounted against a subject's own antigens, referred to as self-antigens. A "self-antigen" as used herein refers to an antigen of a normal host tissue. Normal host tissue does not include neoplastic cells.

Accordingly, in some embodiments, the autoimmune diseases to be treated or prevented using the methods described herein, include, but are not limited to: rheumatoid arthritis, Crohn's disease, ulcerative colitis, multiple sclerosis, primary sclerosing cholangitis, systemic lupus erythematosus (SLE), autoimmune encephalomyelitis, myasthenia gravis (MG), Hashimoto's thyroiditis, Goodpasture's syndrome, pemphigus (e.g., pemphigus vulgaris), Grave's disease, autoimmune hemolytic anemia, autoimmune thrombocytopenic purpura, scleroderma with anti-collagen antibodies, mixed connective tissue disease, polymyositis, pernicious anemia, idiopathic Addison's disease, autoimmune-associated infertility, Kawasaki's disease, glomerulonephritis (e.g., crescentic glomerulonephritis, proliferative glomerulonephritis), bullous pemphigoid, Sjogren's syndrome, insulin resistance, and autoimmune diabetes mellitus (type 1 diabetes mellitus; insulin-dependent diabetes mellitus). Autoimmune disease has been recognized also to encompass atherosclerosis and Alzheimer's disease. In one embodiment of the aspects described herein, the autoimmune disease is selected from the group consisting of multiple sclerosis, type-I diabetes, Hashinoto's thyroiditis, Crohn's disease, rheumatoid arthritis, systemic lupus erythematosus, gastritis, autoimmune hepatitis, hemolytic anemia, autoimmune hemophilia, autoimmune lymphoproliferative syndrome (ALPS), autoimmune uveoretinitis, glomerulonephritis, Guillain-Barre syndrome, psoriasis and myasthenia gravis.

The term "effective amount" as used herein refers to the amount of an agent for modulating (increasing or decreasing) the interactions between FcRn and IgG or a fragment thereof or a variant thereof needed to alleviate at least one or more symptom of the disease or disorder, and relates to a sufficient amount of pharmacological composition to provide the desired effect, for example increasing IL-12 production to so as to treat cancer or infectious diseases, or decreasing IL-12 production to treat autoimmune diseases. The term "therapeutically effective amount" therefore refers to an amount of an agent for modulating the interactions between FcRn and IgG or a fragment thereof or a variant thereof using the methods as disclosed herein, that is sufficient to effect a particular effect when administered to a typical subject. An effective amount as used herein would also include an amount sufficient to delay the development of a symptom of the disease, alter the course of a symptom of disease (for example but not limited to, slow the progression of a symptom of the disease), or reverse a symptom of disease. Thus, it is not possible to specify the exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the agent for modulating interactions between FcRn and IgG or a fragment thereof or a variant thereof, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay. The dosage can be determined by a physician and adjusted, as necessary, to suit observed effects of the treatment.

The agents useful according to the compositions and methods described herein, including antibodies and other polypeptides, are isolated agents, meaning that the agents are substantially pure and are essentially free of other substances with which they may be found in nature or in vivo systems to an extent practical and appropriate for their intended use. In particular, the agents are sufficiently pure and are sufficiently free from other biological constituents of their host cells so as to be useful in, for example, producing pharmaceutical preparations. Because an isolated agent may be admixed with a pharmaceutically acceptable carrier in a pharmaceutical preparation, the agents may comprise only a small percentage by weight of the preparation.

The agents described herein for modulating the interactions between FcRn and IgG or a fragment thereof or a variant thereof can be administered to a subject in need thereof by any appropriate route which results in an effective treatment in the subject. As used herein, the terms "administering," and "introducing" are used interchangeably and refer to the placement of a polypeptide agent into a subject by a method or route which results in at least partial localization of such agents at a desired site, such as a site of inflammation, such that a desired effect(s) is produced.

In some embodiments, the agents described herein for modulating the interactions between FcRn and IgG or a fragment thereof or a variant thereof are administered to a subject by any mode of administration that delivers the agent systemically or to a desired surface or target, and can include, but is not limited to, injection, infusion, instillation, and inhalation administration. To the extent that polypeptide agents can be protected from inactivation in the gut, oral administration forms are also contemplated. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the agents for modulating interactions between FcRn and IgG or a fragment thereof or a variant thereof for use in the methods described herein are administered by intravenous infusion or injection.

The phrases "parenteral administration" and "administered parenterally" as used herein, refer to modes of administration other than enteral and topical administration, usually by injection. The phrases "systemic administration," "administered systemically", "peripheral administration" and "administered peripherally" as used herein refer to the administration of an agent for modulating interactions between FcRn and IgG or a fragment thereof or a variant thereof other than directly into a target site, tissue, or organ, such as a tumor site, such that it enters the subject's circulatory system and, thus, is subject to metabolism and other like processes.

For the clinical use of the methods described herein, administration of an agent for modulating interactions between FcRn and IgG or a fragment thereof or a variant thereof can include formulation into pharmaceutical compositions or pharmaceutical formulations for parenteral administration, e.g., intravenous; mucosal, e.g., intranasal; ocular, or other mode of administration. In some embodiments, an agent for modulating interactions between FcRn and IgG or a fragment thereof or a variant thereof described herein can be administered along with any pharmaceutically acceptable carrier compound, material, or composition which results in an effective treatment in the subject. Thus, a pharmaceutical formulation for use in the methods described herein can contain an agent for modulating interactions between FcRn and IgG or a fragment thereof or a variant thereof as described herein in combination with one or more pharmaceutically acceptable ingredients.

The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically acceptable material, composition or vehicle, such as a liquid or solid filler, diluent, excipient, solvent, media, encapsulating material, manufacturing aid (e.g., lubricant, talc magnesium, calcium or zinc stearate, or steric acid), or solvent encapsulating material, involved in maintaining the stability, solubility, or activity of, an agent for modulating interactions between FcRn and IgG or a fragment thereof or a variant thereof. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) excipients, such as cocoa butter and suppository waxes; (8) oils, such as peanut oil, cottonseed oil, safflower oil, sesame oil, olive oil, corn oil and soybean oil; (9) glycols, such as propylene glycol; (10) polyols, such as glycerin, sorbitol, mannitol and polyethylene glycol (PEG); (11) esters, such as ethyl oleate and ethyl laurate; (12) agar; (13) buffering agents, such as magnesium hydroxide and aluminum hydroxide; (14) alginic acid; (15) pyrogen-free water; (16) isotonic saline; (17) Ringer's solution; (19) pH buffered solutions; (20) polyesters, polycarbonates and/or polyanhydrides; (21) bulking agents, such as polypeptides and amino acids (22) serum components, such as serum albumin, HDL and LDL; (23) C2-C12 alchols, such as ethanol; and (24) other non-toxic compatible substances employed in pharmaceutical formulations. Release agents, coating agents, preservatives, and antioxidants can also be present in the formulation. The terms such as "excipient", "carrier", "pharmaceutically acceptable carrier" or the like are used interchangeably herein.

The agents for modulating (increasing or decreasing) interactions between FcRn and IgG or a fragment thereof or a variant thereof described herein can be specially formulated for administration of the compound to a subject in solid, liquid or gel form, including those adapted for the following: (1) parenteral administration, for example, by subcutaneous, intramuscular, intravenous or epidural injection as, for example, a sterile solution or suspension, or sustained-release formulation; (2) topical application, for example, as a cream, ointment, or a controlled-release patch or spray applied to the skin; (3) intravaginally or intrarectally, for example, as a pessary, cream or foam; (4) ocularly; (5) transdermally; (6) transmucosally; or (79) nasally. Additionally, a bispecific or multispecific polypeptide agent can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960.

Further embodiments of the formulations and modes of administration of an agent for modulating interactions between FcRn and IgG or a fragment thereof or a variant thereof that can be used in the methods described herein are illustrated below.

Parenteral Dosage Forms. Parenteral dosage forms of an agent for modulating (increasing or decreasing) interactions between FcRn and IgG or a fragment thereof or a variant thereof can also be administered to a subject by various routes, including, but not limited to, subcutaneous, intravenous (including bolus injection), intramuscular, and intraarterial. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, controlled-release parenteral dosage forms, and emulsions.

Suitable vehicles that can be used to provide parenteral dosage forms of the disclosure are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

Aerosol formulations. An agent for modulating (increasing or decreasing) interactions between FcRn and IgG or a fragment thereof or a variant thereof can be packaged in a pressurized aerosol container together with suitable propellants, for example, hydrocarbon propellants like propane, butane, or isobutane with conventional adjuvants. An agent for modulating interactions between FcRn and IgG or a fragment thereof or a variant thereof interactions can also be administered in a non-pressurized form such as in a nebulizer or atomizer. An agent for modulating interactions between FcRn and IgG or a fragment thereof or a variant thereof can also be administered directly to the airways in the form of a dry powder, for example, by use of an inhaler.

Suitable powder compositions include, by way of illustration, powdered preparations of an agent for modulating interactions between FcRn and IgG or a fragment thereof or a variant thereof thoroughly intermixed with lactose, or other inert powders acceptable for intrabronchial administration. The powder compositions can be administered via an aerosol dispenser or encased in a breakable capsule which can be inserted by the subject into a device that punctures the capsule and blows the powder out in a steady stream suitable for inhalation. The compositions can include propellants, surfactants, and co-solvents and can be filled into conventional aerosol containers that are closed by a suitable metering valve.

Aerosols for the delivery to the respiratory tract are known in the art. See for example, Adjei, A. and Garren, J. Pharm. Res., 1: 565-569 (1990); Zanen, P. and Lamm, J.-W. J. Int. J. Pharm., 114: 111-115 (1995); Gonda, I. "Aerosols for delivery of therapeutic an diagnostic agents to the respiratory tract," in Critical Reviews in Therapeutic Drug Carrier Systems, 6:273-313 (1990); Anderson et al., Am. Rev. Respir. Dis., 140: 1317-1324 (1989)) and have potential for the systemic delivery of peptides and proteins as well (Patton and Platz, Advanced Drug Delivery Reviews, 8:179-196 (1992)); Timsina et. al., Int. J. Pharm., 101: 1-13 (1995); and Tansey, I. P., Spray Technol. Market, 4:26-29 (1994); French, D. L., Edwards, D. A. and Niven, R. W., Aerosol Sci., 27: 769-783 (1996); Visser, J., Powder Technology 58: 1-10 (1989)); Rudt, S. and R. H. Muller, J. Controlled Release, 22: 263-272 (1992); Tabata, Y, and Y. Ikada, Biomed. Mater. Res., 22: 837-858 (1988); Wall, D. A., Drug Delivery, 2: 10 1-20 1995); Patton, J. and Platz, R., Adv. Drug Del. Rev., 8: 179-196 (1992); Bryon, P., Adv. Drug. Del. Rev., 5: 107-132 (1990); Patton, J. S., et al., Controlled Release, 28: 15 79-85 (1994); Damms, B. and Bains, W., Nature Biotechnology (1996); Niven, R. W., et al., Pharm. Res., 12(9); 1343-1349 (1995); and Kobayashi, S., et al., Pharm. Res., 13(1): 80-83 (1996), contents of all of which are herein incorporated by reference in their entirety.

The formulations of the agents for modulating (increasing or decreasing) interactions between FcRn and IgG or a fragment thereof or a variant thereof described herein further encompass anhydrous pharmaceutical compositions and dosage forms comprising the disclosed compounds as active ingredients, since water can facilitate the degradation of some compounds. For example, the addition of water (e.g., 5%) is widely accepted in the pharmaceutical arts as a means of simulating long-term storage in order to determine characteristics such as shelf life or the stability of formulations over time. See, e.g., Jens T. Carstensen, Drug Stability: Principles & Practice, 379-80 (2nd ed., Marcel Dekker, NY, N.Y.: 1995). Anhydrous pharmaceutical compositions and dosage forms of the disclosure can be prepared using anhydrous or low moisture containing ingredients and low moisture or low humidity conditions. Pharmaceutical compositions and dosage forms that comprise lactose and at least one active ingredient that comprise a primary or secondary amine are preferably anhydrous if substantial contact with moisture and/or humidity during manufacturing, packaging, and/or storage is expected. Anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials) with or without desiccants, blister packs, and strip packs.

Controlled and Delayed Release Dosage Forms. In some embodiments of the methods described herein, an agent for modulating (increasing or decreasing) interactions between FcRn and IgG or a fragment thereof or a variant thereof can be administered to a subject by controlled- or delayed-release means. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. (Kim, Cherng-ju, Controlled Release Dosage Form Design, 2 (Technomic Publishing, Lancaster, Pa.: 2000)). Controlled-release formulations can be used to control a compound's onset of action, duration of action, plasma levels within the therapeutic window, and peak blood levels. In particular, controlled- or extended-release dosage forms or formulations can be used to ensure that the maximum effectiveness of a compound of formula (I) is achieved while minimizing potential adverse effects and safety concerns, which can occur both from under-dosing a drug (i.e., going below the minimum therapeutic levels) as well as exceeding the toxicity level for the drug.

A variety of known controlled- or extended-release dosage forms, formulations, and devices can be adapted for use with the agents for modulating interactions between FcRn and IgG or a fragment thereof or a variant thereof described herein. Examples include, but are not limited to, those described in U.S. Pat. Nos. 3,845,770; 3,916,899; 3,536,809; 3,598,123; 4,008,719; 5674,533; 5,059,595; 5,591,767; 5,120,548; 5,073,543; 5,639,476; 5,354,556; 5,733,566; and 6,365,185 B1, each of which is incorporated herein by reference in their entireties. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed salt forms of the disclosed compounds and thus effect controlled delivery of the drug. Examples of specific anion exchangers include, but are not limited to, Duolite® A568 and Duolite® AP143 (Rohm&Haas, Spring House, Pa. USA).

In some embodiments, an agent for modulating (increasing or decreasing) interactions between FcRn and IgG or a fragment thereof or a variant thereof for use in the methods described herein is administered to a subject by sustained release or in pulses. Pulse therapy is not a form of discontinuous administration of the same amount of a composition over time, but comprises administration of the same dose of the composition at a reduced frequency or administration of reduced doses. Sustained release or pulse administrations are particularly preferred when the disorder occurs continuously in the subject, for example where the subject has continuous or chronic symptoms of a viral infection. Each pulse dose can be reduced and the total amount of the agent for modulating interactions between FcRn and IgG or a fragment thereof or a variant thereof administered over the course of treatment to the patient is minimized.

The interval between pulses, when necessary, can be determined by one of ordinary skill in the art. Often, the interval between pulses can be calculated by administering another dose of the composition when the composition or the active component of the composition is no longer detectable in the subject prior to delivery of the next pulse. Intervals can also be calculated from the in vivo half-life of the composition. Intervals can be calculated as greater than the in vivo half-life, or 2, 3, 4, 5 and even 10 times greater the composition half-life. Various methods and apparatus for pulsing compositions by infusion or other forms of delivery to the patient are disclosed in U.S. Pat. Nos. 4,747,825; 4,723,958; 4,948,592; 4,965,251 and 5,403,590.

Assays for Assessing Efficacy of Therapeutic Agents

Provided herein are methods for determining the efficacy of a treatment in a subject in need thereof. The method includes providing a sample from a subject, assaying the sample for levels of any one or more of IL-12, TNF-α, IFN-γ, GM-CSF, IL-3, IL-2, granzyme B, Tbet or a combination thereof and determining whether the treatment is efficacious.

In one embodiment, the subject is diagnosed with cancer or an infectious disease and is receiving or has received a treatment that includes a composition comprising immunoglobulin G (IgG) or a variant thereof or a fragment thereof. In the subject receiving a composition comprising immunoglobulin G (IgG) or a variant thereof or a fragment thereof, the treatment is determined to be efficacious if the levels of any one or more of IL-12, TNF-α, IFN-γ, GM-CSF, IL-3, IL-2, granzyme B, Tbet or a combination thereof in the sample from the subject is higher relative to the levels in a reference sample. In the subject receiving a composition comprising immunoglobulin G (IgG) or a variant thereof or a fragment thereof, the treatment is determined to be not efficacious if the levels of any one or more of IL-12, TNF-α, IFN-γ, GM-CSF, IL-3, IL-2, granzyme B, Tbet or a combination in the sample from the subject is lower relative to the levels in a reference sample In one embodiment, the subject is diagnosed with an autoimmune disease and is receiving or has received a treatment that includes a composition comprising an agent that inhibits signaling mediated by interaction between FcRn and IgG. In the subject receiving the composition comprising an agent that inhibits signaling mediated by interaction between FcRn and IgG, the treatment is determined to be efficacious if the levels of any one or more of IL-12, TNF-α, IFN-γ, GM-CSF, IL-3, IL-2, granzyme B, Tbet or a combination in the sample from the subject is lower relative to the levels in a reference sample. In the subject receiving the composition comprising an agent that inhibits signaling mediated by interaction between FcRn and IgG, the treatment is determined to be not efficacious if the levels of any one or more of IL-12, TNF-α, IFN-γ, GM-CSF, IL-3, IL-2, granzyme B, Tbet or a combination in the sample from the subject is higher relative to the levels in a reference sample.

In various embodiments, the sample is blood, plasma or tissue.

In various embodiments, the methods for assaying the levels of IL-12, TNF-α, IFN-γ, GM-CSF, IL-3, IL-2, granzyme B, or Tbet in a sample will be apparent to a person of skill in the art. For example, specific antibodies may be used to detect the presence of one or more proteins of interest. Any suitable immunoassay method may be utilized, including those which are commercially available, to ascertain the presence of, and optionally quantify the amount of, the protein of interest present in the sample. In various embodiments, the antibody is any one or more of a monoclonal antibody or fragment thereof, a polyclonal antibody or a fragment thereof, chimeric antibodies, humanized antibodies, human antibodies, and a single chain antibody. Extensive discussion of the known immunoassay techniques is not required here since these are known to those of skill in the art. Typical suitable immunoassay techniques include Western blots, sandwich enzyme-linked immunoassays (ELISA), radioimmunoassays (RIA), competitive binding assays, homogeneous assays, heterogeneous assays, etc. Various known immunoassay methods are reviewed, e.g., in Methods in Enzymology, 70, pp. 30-70 and 166-198 (1980).

Further, "sandwich-type" assays may be used with the methods described herein. Some examples of sandwich-type assays are described in U.S. Pat. No. 4,168,146 and U.S. Pat. No. 4,366,241. Alternatively, "competitive-type" assays may be used with the methods described herein. In a competitive assay, the labeled probe is generally conjugated with a molecule that is identical to, or an analog of, the analyte. Thus, the labeled probe competes with the analyte of interest for the available receptive material. Examples of competitive immunoassay devices are described in U.S. Pat. No. 4,235,601, U.S. Pat. No. 4,442,204 and U.S. Pat. No. 5,208,535.

Techniques that may be used to assess the amount of nucleic acid encoding any one or more of IL-12, TNF-α, IFN-γ, GM-CSF, IL-3, IL-2, granzyme B, or Tbet from a sample obtained from a subject include but are not limited to in situ hybridization (e.g., Angerer (1987) *Meth. Enzymol* 152: 649). Preferred hybridization-based assays include, but are not limited to, traditional "direct probe" methods such as Southern blots or in situ hybridization (e.g., FISH and FISH plus SKY), and "comparative probe" methods such as comparative genomic hybridization (CGH), e.g., cDNA-based or oligonucleotide-based CGH. The methods can be used in a wide variety of formats including, but not limited to, substrate (e.g. membrane or glass) bound methods or array-based approaches. Probes that may be used for nucleic acid analysis are typically labeled, e.g., with radioisotopes or fluorescent reporters. Preferred probes are sufficiently long so as to specifically hybridize with the target nucleic acid(s) under stringent conditions. The preferred size range is from about 200 bases to about 1000 bases. Hybridization protocols suitable for use with the methods of the invention are described, e.g., in Albertson (1984) *EMBO J.* 3: 1227-1234; Pinkel (1988) *Proc. Natl. Acad. Sci. USA* 85: 9138-9142; EPO Pub. No. 430,402; *Methods in Molecular Biology*, Vol. 33: In situ Hybridization Protocols, Choo, ed., Humana Press, Totowa, N.J. (1994), Pinkel, et al. (1998) *Nature Genetics* 20: 207-211, and/or Kallioniemi (1992) *Proc. Natl Acad Sci USA* 89:5321-5325 (1992).

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis, et al. (1990) PCR Protocols, *A Guide to Methods and Applications*, Academic Press, Inc. N.Y.). Measurement of DNA copy number at microsatellite loci using quantitative PCR analysis is described in Ginzonger, et al. (2000) *Cancer Research* 60:5405-5409. The known nucleic acid sequence for the genes is sufficient to enable one of skill in the art to routinely select primers to amplify any portion of the gene. Fluorogenic quantitative PCR may also be used in the methods of the invention. In fluorogenic quantitative PCR, quantitation is based on amount of fluorescence signals, e.g., TaqMan and sybr green.

Other suitable amplification methods include, but are not limited to, ligase chain reaction (LCR) (see Wu and Wallace (1989) *Genomics* 4: 560, Landegren, et al. (1988) *Science* 241:1077, and Barringer et al. (1990) *Gene* 89: 117), transcription amplification (Kwoh, et al. (1989) *Proc. Natl. Acad. Sci. USA* 86: 1173), self-sustained sequence replication (Guatelli, et al. (1990) *Proc. Nat. Acad. Sci. USA* 87: 1874), dot PCR, and linker adapter PCR, etc.

In certain embodiments, other techniques may be used to determine expression of a polynucleotide gene product, including microarray analysis (Han, M., et al., Nat Biotechnol, 19: 631-635, 2001; Bao, P., et al., Anal Chem, 74: 1792-1797, 2002; Schena et al., Proc. Natl. Acad. Sci. USA 93:10614-19, 1996; and Heller et al., Proc. Natl. Acad. Sci. USA 94:2150-55, 1997) and SAGE (serial analysis of gene expression). Like MPSS, SAGE is digital and can generate a large number of signature sequences. (see e.g., Velculescu, V. E., et al., Trends Genet, 16: 423-425., 2000; Tuteja R. and Tuteja N. Bioessays. 2004 August; 26(8):916-22), although orders of magnitude fewer than that are available from techniques such as MPSS. Examples of nucleic acid microarrays may be found in, for example, U.S. Pat. Nos. 6,391,623, 6,383,754, 6,383,749, 6,380,377, 6,379,897, 6,376,191, 6,372,431, 6,351,712 6,344,316, 6,316,193, 6,312,906, 6,309,828, 6,309,824, 6,306,643, 6,300,063.

In various embodiments of the methods described herein, the reference value is based on the presence and/or amount of protein of interest including any one or more of IL-12, TNF-α, IFN-γ, GM-CSF, IL-3, IL-2, granzyme B, or Tbet in a sample obtained from the subject (for example, a subject having cancer, infectious diseases or autoimmune diseases).

In some embodiments, the reference value is the mean or median presence of the protein of interest (or nucleic acid encoding the protein of interest) in a population of subjects that do not have a disease-state. For example, in subjects with cancer, the reference value is the mean or median presence of any one or more of IL-12, TNF-α, IFN-γ, GM-CSF, IL-3, IL-2, granzyme B, or Tbet in a population of subjects that do not have the cancer. For example, in subjects with an infectious disease, the reference value is the mean or median presence of any one or more of IL-12, TNF-α, IFN-γ, GM-CSF, IL-3, IL-2, granzyme B, or Tbet in a population of subjects that do not have the infectious disease. For example, in subjects with an autoimmune disease, the reference value is the mean or median presence of any one or more of IL-12, TNF-α, IFN-γ, GM-CSF, IL-3, IL-2, granzyme B, or Tbet in a population of subjects that do not have the autoimmune disease. In various embodiments, the levels of any one or more of IL-12, TNF-α, IFN-γ, GM-CSF, IL-3, IL-2, granzyme B, or Tbet is altered (increased if the subject has cancer or an infectious disease and decreased if the subject has an autoimmune disease) relative to the reference value by at least or about 10%, 20%, 30%, 40%, 50%, 60%, 70%, 80%, 90% or 100%. In various embodiments the levels of any one or more of IL-12, TNF-α, IFN-γ, GM-CSF, IL-3, IL-2, granzyme B, or Tbet is altered (increased if the subject has cancer or an infectious disease and decreased if the subject has an autoimmune disease) relative to the reference value by at least or about 1-fold, 2-fold, 3-fold, 4-fold, 5-fold, 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 100-fold or a combination thereof.

While particular embodiments of various aspects disclosed herein have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Exemplary embodiments of the various aspects disclosed herein can be described by one or more of the following numbered paragraphs:

A. A composition for increasing IL-12 production, the composition comprising immunoglobulin G (IgG) or a variant thereof or a fragment thereof.

B. The composition of paragraph A, wherein the composition increases signaling mediated by interaction between IgG and FcRn.
C. The composition of paragraph A, wherein the composition increases an immune response against an antigen.
D. The composition of paragraph A, wherein the variant IgG comprises a methionine to leucine substitution at position 428 and an asparagine to serine substitution at position 434.
E. The composition of paragraph A, further comprising an antigen conjugated to IgG or a variant thereof or a fragment thereof so as to create a monomeric or a multimeric structure which can cross-link FcRn.
F. The composition of paragraph A, further comprising an antigen complexed to IgG or a variant thereof or a fragment thereof so as to create a multimeric structure which can cross-link FcRn.
G. The composition of paragraphs E or F, wherein the antigen is a tumor antigen, an endogenous antigen, a cell-associated antigen, an apoptotic body, a microbial antigen, a viral antigen, a parasitic antigen or a combination thereof.
H. The composition of paragraph G, wherein the antigen is a protein or a proteomimetic thereof, a peptide or a peptidomimetic thereof, a lipid or a combination thereof.
I. The composition of paragraph A, wherein the IgG or a variant thereof or a fragment thereof is mammalian.
J. The composition of paragraph A, wherein the IgG or a variant thereof or a fragment thereof is human.
K. A composition for decreasing IL-12 production, the composition comprising an agent that inhibits signaling mediated by interaction between FcRn and IgG.
L. The composition of paragraph K, wherein the agent is any one or more of a peptide, protein, small molecule, nucleic acid, aptamer, oligonucleotide, antibody or a combination thereof.
M. The composition of paragraph L, wherein the nucleic acid is siRNA specific to FcRn.
N. The composition of paragraph L, wherein the antibody is selected from the group consisting of a monoclonal antibody or a fragment thereof, a polyclonal antibody or a fragment thereof, chimeric antibody, humanized antibody and single chain antibody.
O. The composition of paragraph K, wherein the agent is a bispecific agent comprising binding sites for IgG and FcRn.
P. The composition of paragraph K, wherein the agent is a recombinant Fc portion of IgG or a biologically active portion thereof or a proteo-mimetic thereof.
Q. The composition of paragraph P, wherein the Fc portion of IgG or a biologically active portion thereof is mammalian.
R. The composition of paragraph P, wherein the Fc portion of IgG or a biologically active portion thereof is human.
S. A method for modulating the interaction between FcRn and IgG comprising contacting a cell with an agent that binds FcRn and/or IgG and modulates binding of FcRn to IgG.
T. The method of paragraph S, wherein the agent increases signaling mediated by interaction of FcRn and IgG.
U. The method of paragraph S, wherein the agent decreases signaling mediated by interaction of FcRn and IgG.
V. The method of paragraph S, wherein the agent comprises binding sites specific for IgG and FcRn.
W. The method of paragraph S, wherein the agent comprises binding sites specific for IgG or FcRn.
X. The method of paragraph S, wherein the agent comprises binding sites specific for Fc portion of IgG.
Y. The method of paragraph S, wherein agent comprises a bispecific polypeptide agent comprising binding sites specific for IgG and FcRn.
Z. The method of paragraph Y, wherein the bispecific polypeptide agent comprises an antibody or antigen binding portion thereof that specifically binds FcRn and an antibody or antigen binding portion thereof that specifically binds IgG.
AA. A method for treating, inhibiting, preventing metastasis of or preventing relapse of cancer in a subject in need thereof comprising:
(a) providing a composition comprising immunoglobulin G (IgG) or a variant thereof or a fragment thereof; and
(b) administering an effective amount of the composition to the subject so as to treat, inhibit, prevent metastasis or prevent relapse of cancer in the subject.
BB. A method for treating, inhibiting or reducing the severity of infectious diseases in a subject in need thereof comprising:
(a) providing a composition comprising immunoglobulin G (IgG) or a variant thereof or a fragment thereof; and
(b) administering an effective amount of the composition to the subject so as to treat, inhibit or reduce the severity of infectious diseases in the subject.
CC. The method of paragraphs AA or BB, wherein the composition increases signaling mediated by interaction of IgG and FcRn.
DD. The method of paragraphs AA or BB, wherein the composition increases an immune response against the antigen.
EE. The method of paragraphs AA or BB, wherein the variant IgG comprises a methionine to leucine substitution at position 428 and an asparagine to serine substitution at position 434.
FF. The method of paragraphs AA or BB, wherein the composition further comprises an antigen, wherein the antigen is conjugated to the IgG or a variant thereof or a fragment thereof, or wherein the antigen is complexed with the IgG or a variant thereof or a fragment thereof.
GG. The method of paragraph FF, wherein the antigen is a tumor antigen, a microbial antigen, a viral antigen, a parasitic antigen or a combination thereof.
HH. The method of paragraph FF, wherein the antigen is a protein or a proteomimetic thereof, a peptide or a peptidomimetic thereof, a lipid or a combination thereof.
II. A method for treating, inhibiting or reducing the severity of autoimmune diseases in a subject in need thereof comprising:
(a) providing a composition comprising an agent that inhibits signaling mediated by interaction between FcRn and IgG; and
(b) administering an effective amount of the composition to the subject so as to treat, inhibit or reduce the severity of autoimmune diseases in the subject.
JJ. The method of paragraph II, wherein the agent reduces or inhibits production of IL-12.

KK. The method of paragraph II, wherein the agent is any one or more of a peptide, protein, small molecule, nucleic acid, aptamer, oligonucleotide, antibody or a combination thereof.

LL. The method of paragraph KK, wherein the nucleic acid is siRNA specific to FcRn.

MM. The method of paragraph KK, wherein the antibody is selected from the group consisting of a monoclonal antibody or a fragment thereof, a polyclonal antibody or a fragment thereof, chimeric antibody, humanized antibody and single chain antibody.

NN. The method of paragraph II, wherein the agent is a bispecific agent comprising binding sites for IgG and FcRn.

OO. The method of paragraph KK, wherein the agent is a recombinant Fc portion of IgG or a biologically active portion thereof or a proteo-mimetic thereof.

PP. A method for downregulating expression of IL-12 in a subject comprising:
(a) providing a composition comprising an FcRn antibody; and
(b) administering an effective amount of the composition to the subject so as to downregulate expression of IL-12 in the subject.

QQ. A method for determining the efficacy of treatment in a subject in need thereof comprising:
(a) providing a sample from a subject, wherein the subject has been administered an effective amount of a composition comprising immunoglobulin G (IgG) or a variant thereof or a fragment thereof;
(b) assaying the levels of any one or more of IL-12, TNF-α, IFN-γ, GM-CSF, IL-3, IL-2, granzyme B, Tbet or a combination thereof in the sample; and
(c) determining that the treatment is efficacious if the levels of any one or more of IL-12, TNF-α, IFN-γ, GM-CSF, IL-3, IL-2, granzyme B, Tbet or a combination thereof in the sample from the subject is higher relative to the levels in a reference sample or determining that the treatment is not efficacious if the levels of any one or more of IL-12, TNF-α, IFN-γ, GM-CSF, IL-3, IL-2, granzyme B, Tbet or a combination thereof in the sample from the subject is lower relative to the levels in a reference sample, wherein the subject has cancer or an infectious disease.

RR. A method for determining the efficacy of treatment in a subject in need thereof comprising:
(a) providing a sample from a subject, wherein the subject has been administered a composition comprising an agent that inhibits signaling mediated by interaction between FcRn and IgG;
(b) assaying the levels of any one or more of IL-12, TNF-α, IFN-γ, GM-CSF, IL-3, IL-2, granzyme B, Tbet or a combination thereof in the sample; and
(c) determining that the treatment is efficacious if the levels of any one or more of IL-12, TNF-α, IFN-γ, GM-CSF, IL-3, IL-2, granzyme B, Tbet or a combination thereof in the sample from the subject is lower relative to the levels in a reference sample or determining that the treatment is not efficacious if the levels of any one or more of IL-12, TNF-α, IFN-γ, GM-CSF, IL-3, IL-2, granzyme B, Tbet or a combination thereof in the sample from the subject is higher relative to the levels in a reference sample, wherein the subject has an autoimmune disease.

SS. The method of paragraph QQ or RR, wherein the sample is blood, plasma or tissue.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Experimental Methods

Mice and tumor models. Fcgrt−/− mice (Roopenian et al., 2003), deficient in FcRn, on a C57BL/6 background were originally purchased from The Jackson Laboratory. FcgrtFl/Fl mice were a kind gift of Dr. E. Sally Ward (University of Texas Southwestern Medical Center) (Montoyo et al., 2009). hFCGRT-hB2M-mFcgrt−/− mice have been described previously (Yoshida et al., 2004). All procedures were approved by the Harvard Medical Area Standing Committee on Animals. AOM, AOM/DSS, Apcmin/+ and lung metastasis tumor models were performed using previously described protocols (LeibundGut-Landmann et al., 2008; Meunier et al., 2009; Wirtz et al., 2007).

Induction of Colorectal Cancer

Figures 8A, 8B, 8C, 8D, 8E, 8F, 8G, 8H, 8I, 8J, 8K:
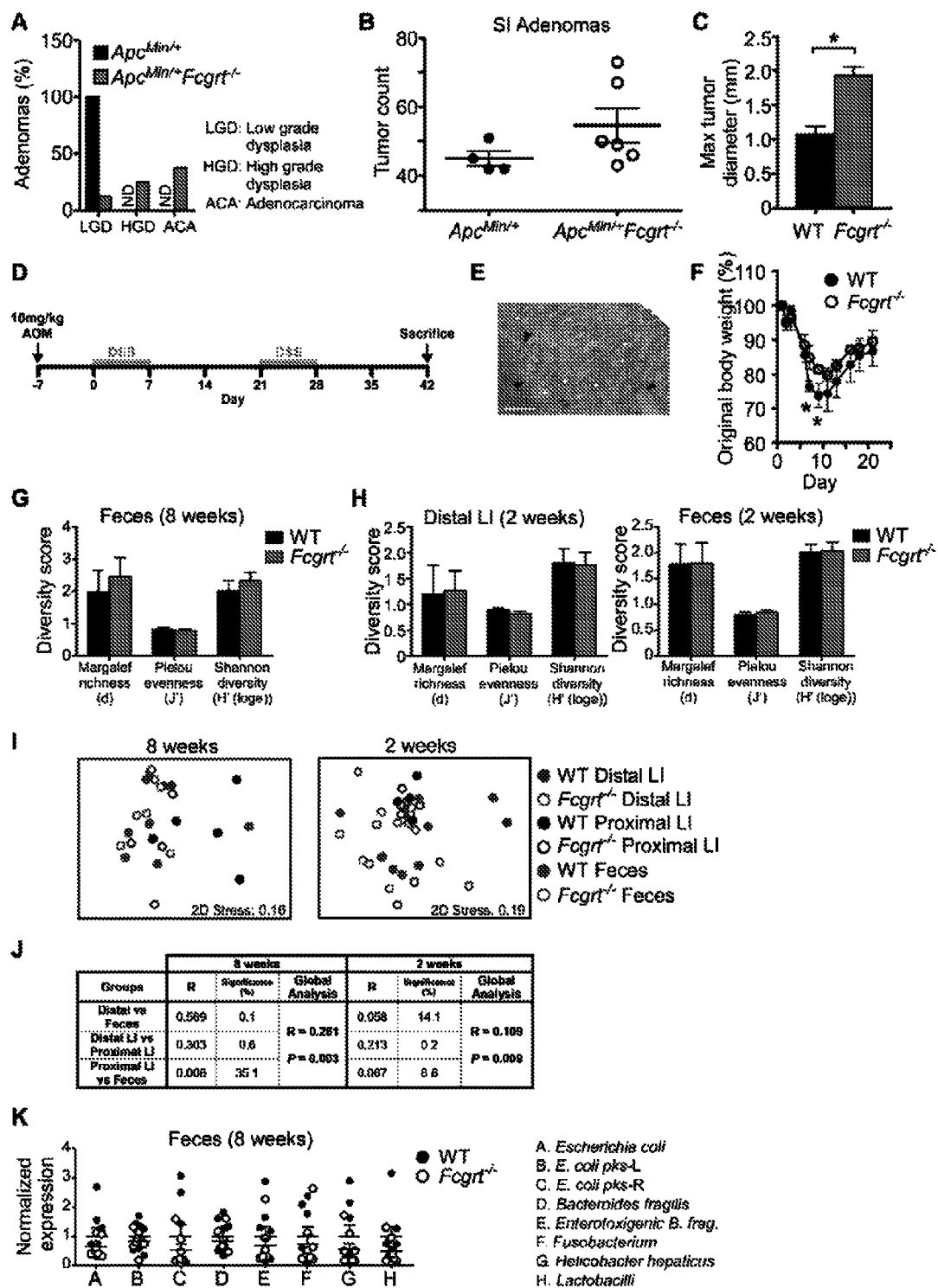
FIGS. 8A-8K depict, in accordance with various embodiments of the present invention that loss of FcRn predisposes to the development of more severe inflammation- and non-inflammation-associated colorectal cancer (CRC) via a mechanism that is independent of intestinal microbiota.

Inflammation-associated CRC was induced by a single i.p. dose of 10 mg/kg azoxymethane (AOM) (Sigma Aldrich) and the subsequent administration of two 7-day courses of 1.5% dextran sodium sulfate (DSS) (MP Biomedicals) in drinking water, as outlined in FIG. 8D and described previously (Wirtz et al., 2007). Tumor burden was assessed two weeks after withdrawal of the final course of DSS. Tumor load was calculated as the sum of all tumor diameters, as described previously (Grivennikov et al., 2012). Bone marrow chimeras were generated by lethal irradiation of recipients (2×6 Gy) followed by reconstitution with 1×10$^6$ bone marrow cells from the appropriate donor. Treatment of the chimeras with AOM/DSS was begun 8 weeks after reconstitution. Non-inflammation-associated CRC was induced by eight weekly i.p. injections of 10 mg/kg AOM. Tumor burden was assessed 12 weeks after administration of the final dose of AOM. Tumor burden in ApcMin/+ and ApcMin/+Fcgrt−/− mice was assessed at 5-6 months of age in untreated mice. In all experiments, tumor evaluation 14 was carried out blindly by counting macroscopically visible tumors (>1 mm in diameter) and measuring the largest diameter of each lesion with digital calipers.

Adoptive Transfer Experiments

Figures 10A, 10B, 10C, 10D, 10E, 10F, 10G, 10H, 10I, 10J, 10K, 10L:
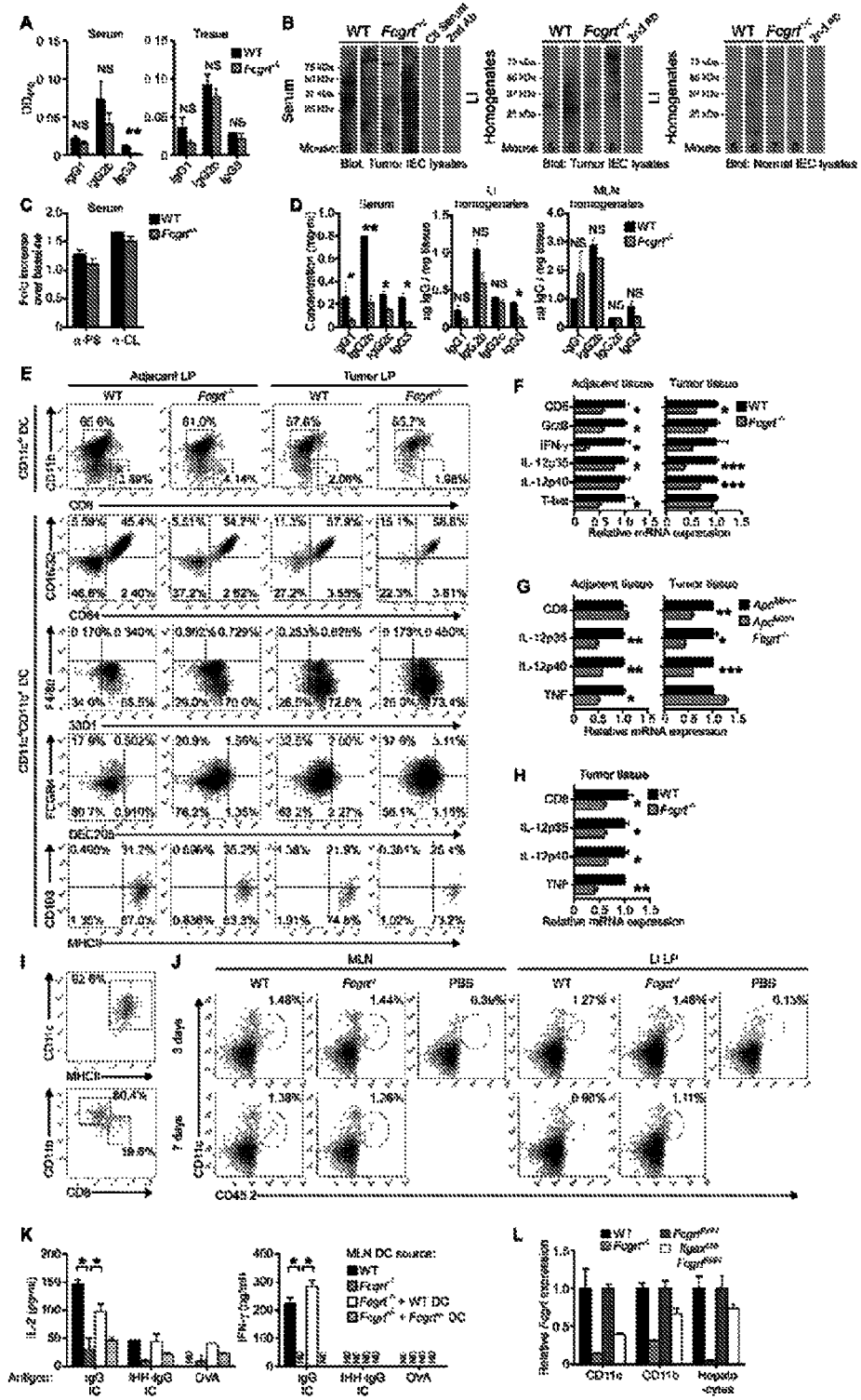
FIGS. 10A-10L depict, in accordance with various embodiments of the present invention that FcRn-dependent dendritic cell (DC)-mediated tumor protection is associated with the presence of tumor-antigen reactive IgG in intestinal tissues and the generation of a local Th1/Tc1 polarizing cytokine environment.

CD8+ T cells or DC from the MLN and LI lamina propria were isolated from donor mice at day 21 of the AOM/DSS treatment course (see FIG. 8D). Isolation of cells was carried out by sequential collagenase digestions, as previously described (Baker et al., 2011). CD8+ T cells were subsequently purified using negative magnetic selection (Miltenyi Biotec). DC were purified using positive magnetic selection with CD11c-microbeads (Miltenyi Biotec) and yielded predominantly CD8−CD11b+ DC (FIG. 10I). 1×10$^6$ CD8+ T cells or DC were adoptively transferred to recipient mice via i.p. injection, on days 0 and 21 for CD8+ T cells and days −7 and 14 for DC. Appropriate localization of the transferred cells to the MLN and LI lamina propria of the recipient mice was verified in separate experiments using mice congenic for Ly5.1 expression (FIG. 10J). For depletion of CD8+ T cells, mice were initially treated i.p. on consecutive days with three doses of 0.5 mg of an anti-CD8 antibody (clone 53-6.72, BWHBRI Antibody Core Facility) (or isotype control) beginning 3 days prior to the initial DC transfer (Kruisbeek, 1991). Thereafter, CD8+ T cell depletion was maintained by administration of 0.5 mg anti-CD8 antibody (or isotype) every three days until termination of the experiment. For IL-12 neutralization, mice were initially treated on consecutive days with three i.p. doses of 0.5 mg of an anti-IL-12p40 antibody (clone C17.8) (kindly provided by Dr. Giorgio Trinchieri, National Cancer Institute) (or isotype control) beginning 3 days prior to the initial DC transfer. Neutralization was maintained by administration of 0.5 mg anti-IL-12p40 antibody (or isotype) twice per week until termination of the experiment.

Lung Metastasis Experiments

Lung metastases were induced by the i.v. injection of $0.5 \times 10^6$ OVA-transfected B16 melanoma cells (OVA-B16 cells, a generous gift of Dr. Kenneth Rock, University of Massachusetts Medical School) in log phase growth (Falo et al., 1995; 15 LeibundGut-Landmann et al., 2008). Evaluation of lung nodules was carried out following lung inflation and fixation in 10% formalin. For DC immunization experiments, DC were isolated by collagenase digestion from the lung and draining lymph nodes of metastasis-bearing donor mice and $1 \times 10^6$ DC were injected s.c. into the hind footpad of recipient mice. Two weeks later, recipients were given OVA-B16 cells, as above. For CD8+ T cell protection experiments, OVA-specific OT-I CD8+ T cells were stimulated with DC pulsed with IgG IC or IHH-IgG IC, as described above, in the presence of 20 U/ml IL-2 for 5 days before purification and i.v. injection of $1 \times 10^6$ T cells into recipient mice having received OVA-B16 cells 24 h earlier. For immunization with ex vivo loaded DC, LS-IgG was generated and WT DC were loaded for 3 h ex vivo with OVA-containing IgG IC or LS-IgG IC and then washed extensively before s.c. footpad injection. For quantification of CD8+ T cells specific for the tumor antigen OVA, lungs were digested with collagenase II as previously described (Olszak et al., 2012) in order to create a single cell suspension. Cells were stained with anti-CD3, anti-CD8 and the SIINFEKL-H2-Kb tetramer or a control LCMV-H2-Kb tetramer (Beckman-Coulter). Frequency of cells positive for the SIINFEKL-H2-Kb tetramer within the CD3+CD8+ gate was assessed by flow cytometry.

Microbiota Analysis

Analysis of the microbiota was conducted as using previously published methods (Uronis et al., 2011). Briefly, for T-RFLP analysis, samples were collected from the feces, proximal LI or distal LI of adult (8-week old) and pre-weaning (2-week old) littermates and snap frozen in liquid nitrogen. Samples were processed for T-RFLP analysis as previously described (Uronis et al., 2011). Analysis was conducted using Sequentix Gelquest to assign size (length of fragment) and peak height (abundance) to each TRF. Using PRIMER v6, TRF abundance was standardized by total and transformed by square root. The standardized transformed abundances were compiled into a Bray Curtis similarity matrix and Analysis of Similarity (ANOSIM) was used to test for statistically significant differences in overall community composition between genotypes. Diversity was measured using the Shannon diversity (H), Margalef richness (d), and Pielou evenness (J) indices and differences were assessed by Student's t test. For qPCR, samples were collected from the feces, proximal LI or distal LI of 7-week old littermates and snap frozen in liquid nitrogen. Samples were processed as described above. qPCR was performed using previously published primer sets (Arthur et al., 2012; Miyamoto et al., 2002; Periasamy and Kolenbrander, 2009; Rabizadeh et al., 2007; Shames et al., 1995).

Human DC and Tissue Experiments

Human leukopacks were obtained from the Kraft Family Blood Donor Center of the Dana-Farber Cancer Institute and Brigham and Women's Hospital. hMoDC were derived as previously described (Zeissig et al., 2010) for 5 days in 1000 U/ml hGM-CSF and 500 U/ml hIL-4. During the final 24 h of culture, 100 U/ml IFN-γ was added. IgG and IHH-IgG stimulations were carried out as described above. One set of human CRC tissue micro-arrays containing 50 samples of matched tumor and adjacent normal tissue from the same donors were obtained from BioMax USA. A second TMA containing multiple punches from each of 220 patients and for which survival data was available has previously been described (Karamitopoulou et al., 2011). Tissue was stained using the EnVision G2 Doublestain System, Rabbit/Mouse (DAB+/Permanent Red) Kit from Dako following heat-induced epitope retrieval in 10 mM citrate, 1 mM EDTA, 0.05% Tween (pH 6.0). Primary antibodies were anti-hFCGRT (HPA012122, Sigma Aldrich), anti-hCD11c (Novocastra) and anti-hCD8 (Dako) all of which were used at 1/50. Experiments were performed under Brigham and Women's Hospital Review Board approval.

Biochemical Methods

Flow cytometry, RNA analysis, IgG quantification, ChIP, Western blotting, ELISpot and in vitro co-culture experiments were conducted as described herein and as previously described (Baker et al., 2011).

Flow Cytometry

Cells were isolated from the spleen, MLN or colon using collagenase digestion, as previously described (Baker et al., 2011). All antibodies used for flow cytometric staining were purchased from BioLegend except the following: Ki-67 (BD Pharmingen), granzyme B (eBioscience), FCGR4 (Sino Biologicals). Intracellular staining for Granzyme B was carried out using the Cytofix/Cytoperm kit (BD Pharmingen) following a 4h restimulation by PMA (30 ng/ml) and ionomycin (2 μg/ml) (Sigma) and GolgiStop (BD Pharmingen).

RNA Isolation and qPCR

RNA was isolated directly from flow cytometrically sorted cell populations (CD8+ T cells or DC) using an RNeasy MicroKit (Qiagen) or from snap-frozen tissue using an RNeasy MiniKit (Qiagen). RNA was reverse-transcribed using SuperScriptIII (Life Technologies) and quantified by qPCR using SYBR Green technology (Roche).

In Vitro and Ex Vivo Cultures

CD8+ or CD4+ T cell activation was assessed following 24 h of restimulation with plate-bound anti-CD3 and anti-CD28 using a cytometric bead array (BD Pharmingen) Immune complexes were formed using ovalbumin conjugated to the hapten NIP (4-hydroxy-3-iodo-5-nitrophenylacetic acid) and NIP-specific chimeric IgG (IgG), IHH-IgG or LS-IgG. IHH-IgG is a mutational variant of the chimeric IgG protein which contains a NIP-specific mouse Fab fragment and a human IgG1 Fc fragment and which has been rendered incapable of FcRn binding due to the introduction of mutations in three critical amino acids in the Fc region which are required for FcRn ligation as previously described (Baker et al., 2011). LS-IgG was generated by introduction of the M428L/N434S mutations which are known to enhance FcRn binding (Zalevsky et al., 2010) into a previously described chimeric antibody specific for the hapten 4-hydroxy-3-iodo-5-nitrophenylacetic acid (NIP) and containing a human IgG1 Fc (Ober et al., 2001) using the QuikChange site-directed mutagenesis kit (Strategene). In vitro cross presentation assays were carried out by pulsing $1 \times 10^5$ isolated DC with preformed immune complexes (0.5 μg/ml NIP-conjugated OVA+100 μg/ml anti-NIP IgG or anti-NIP IHH-IgG) for 2-3 h followed by extensive washing and the addition of $2 \times 10^5$ purified OT-I CD8+ T cells (Baker et al., 2011). Cytokine secretion was measured after 24h or 48 h by ELISA (BD Pharmingen). For IL-12 neutralization experiments, the indicated concentration of IL-12 neutralizing goat IgG (RnD Systems) or goat isotype control IgG (RnD Systems) was added to DC following IgG IC pulsing. DC were incubated in the presence of the neutralizing antibody for 1 h before addition of the OT-I CD8+ T cells.

IgG Analysis

IgG isotypes in the serum of untreated or treated mice was quantified using isotype specific ELISAs (Southern Biotech). For quantification of tissue IgG, snap frozen tissue was briefly thawed and then homogenized in PBS containing protease inhibitors (Roche). Insoluble material was removed by centrifugation and protein concentration in the clarified supernatant was assessed by BCA assay (Thermo Scientific). Equivalent quantities of protein were used in IgG isotype ELISAs and IgG concentration was normalized to mg of total protein. Tumor specific IgG was evaluated using lysates made from purified tumor epithelial cells, isolated by dispase and collagenase digestion (Baker et al., 2011; Olszak et al., 2012). Tumor lysates were depleted of IgG by overnight incubation with Protein G Sepharose beads (GE Healthcare Life Sciences) at 4° C. For Western blotting, 10 μg lysate from tumor epithelium or normal intestinal epithelium was resolved by SDS-PAGE under reducing conditions and transferred to nitrocellulose membranes. Membrane strips were then probed with 1/10 dilutions of serum or intestinal homogenates from individual mice and developed with anti-mouse IgG-HRP. Blots were developed with ECL Western Blotting Reagent (GE Healthcare). For ELISA, plates were coated with 1/10 dilution of tumor lysate in coating buffer before application of serial dilutions of serum or tissue homogenates and development with anti-mouse IgG-HRP. OVA-specific IgG secreting B cells from OVA-B16 metastasis-bearing mice were quantified by ELISpot (mAbTech) according to the manufacturer's instructions following isolation of B cells with CD19-microbeads (Miltenyi Biotech).

Nuclear Translocation and ChIP

Nuclear translocation of transcription factors was assessed following stimulation of isolated DC with IgG IC (formed as above with FcRn-binding IgG or non-FcRn binding IHH-IgG and NIP-OVA) for the indicated times. Nuclei and cytoplasmic fractions were isolated using the NE-PER Nuclear and Cytoplasmic Extraction Kit (Thermo Scientific). Anti-NF-κB p65, anti-IRF-1 and anti-HDAC antibodies were all purchased from Cell Signaling Technologies. ChIP was performed following IC stimulation with the SimpleChIP Plus Enzymatic Chromatin IP Kit (Magnetic Beads) from Cell Signaling Technologies.

Statistical Analyses

All data are expressed as mean±s.e.m. Unless otherwise specified, data was analyzed using two-tailed unpaired Student's t tests. Significance of results across independent experiments was assessed by pairwise Student's t test. As indicated where relevant, non-normally distributed data was assessed using Mann-Whitney test and survival for mouse experiments was evaluated using Log rank test or Chi-Squared test. The human survival analysis was performed with the Kaplan-Meier method and the two curves were compared with the log rank test. Subsequently, FcRn+CD11c+ status was entered into uni- and multivariate Cox regression analysis. Hazard ratios (HR) and 95% confidence intervals (CI) were used to determine the prognostic effect of FcRn+CD11c+ cell numbers on survival time. All analyses were carried out using GraphPad Prism software (GraphPad Software, Inc.).

Example 2

FcRn Protects Against the Development of Colorectal Cancer

The majority of sporadic colorectal cancers (CRC) arise following a defined series of mutational events often involving inactivation of the adenomatous polyposis coli (APC) gene (Walther et al., 2009). We thus began by investigating whether FcRn could contribute to the development of CRC in ApcMin/+ mice which possess an abnormal copy of Apc and spontaneously develop large numbers of small intestinal adenomas (Saleh and Trinchieri, 2011). Typically, ApcMin/+ mice do not develop colonic lesions in the absence of further insults, such as the additional loss of a tumor suppressor gene (Aoki et al., 2003; Saleh and Trinchieri, 2011). However, ApcMin/+ mice crossed with mice deficient in FcRn (Fcgrt-/-) spontaneously developed significantly more LI tumors than their ApcMin/+ littermates (FIG. 1A). Importantly, high grade dysplasia and local invasion through the LP were detected only in lesions from ApcMin/+Fcgrt-/- but not ApcMin/+ animals (FIGS. 1A and 8A). No differences were detected in the frequency of tumors in the small intestine (SI) (FIG. 8B), where tumor development in ApcMin/+ mice does not depend on a second genetic event (Aoki et al., 2003; Saleh and Trinchieri, 2011). We next investigated the role of FcRn in the development of CRC induced by the chronic administration of a chemical carcinogen, azoxymethane (AOM), which, upon repeated administration, drives the development of colorectal malignancies (Meunier et al., 2009). We observed that Fcgrt-/- mice subjected to a standard regimen of AOM administration developed significantly more abundant and larger tumors (FIGS. 1B and 8C) than did WT littermates. These data demonstrate the importance of FcRn in determining susceptibility to the development of sporadic CRC.

Knowing that inflammatory bowel disease is associated with a heightened risk of CRC and that inflammation plays an important role in driving even sporadic neoplasias (Coghill et al., 2012; Herrinton et al., 2012), we examined whether FcRn-mediated tumor protection extended to inflammation-associated CRC. We found that Fcgrt−/− mice treated with AOM and dextran sodium sulfate (AOM/DSS) (FIG. 8D) (Wirtz et al., 2007) developed significantly larger and more abundant colorectal adenocarcinomas than WT littermates (FIGS. 1C, 1D, 8E). Additionally, at higher concentrations of DSS, Fcgrt−/− mice experienced significantly poorer survival rates compared to their WT littermates (FIG. 1E), indicating that FcRn-mediated anti-tumor immunity is potent enough to influence disease outcome. The smaller initial weight loss in the Fcgrt−/− mice compared to WT controls (FIG. 8F) was consistent with previous findings that Fcgrt−/− mice are protected from IgG-induced colitis (Kobayashi et al., 2009), suggesting that tumor development in the context of FcRn-deficiency is not simply due to increased inflammation.

Certain intestinal microbes may play a role in promoting the development of CRC (Arthur and Jobin, 2011; Arthur et al., 2012). We thus profiled the intestinal microbiota in our WT and Fcgrt−/− littermate mice in order to determine whether FcRn was exerting tumor protection through the regulation of gut microbial composition. Terminal restriction fragment length polymorphism (T-RFLP) analysis of the overall microbial community composition and diversity from WT and Fcgrt−/− littermates revealed no significant differences in either post-weaning, eight week old mice or pre-weaning, two week old mice (FIGS. 1F and 8G, 8H) in any of three separate intestine-associated tissue compartments (proximal LI, distal LI and feces). However, regardless of genotype, the microbiota were found to differ between these three tissue sites, thereby confirming that our analysis had sufficient power to detect differences in microbial composition (FIGS. 8I, 8J). In order to exclude differences in specific organisms previously associated with CRC development (Arthur and Jobin, 2011), we also assessed the abundance of these microbes in a separate cohort of seven week old mice using genus or species specific qPCR and found no significant differences in either the distal LI (FIG. 1G) or feces (FIG. 8K) of WT and Fcgrt−/− littermates. Together, these data demonstrate that FcRn does not protect against colorectal tumor development by regulating intestinal microbial diversity or decreasing the presence of tumor-promoting microbes.

Example 3

Figures 2A, 2B, 2C, 2D:
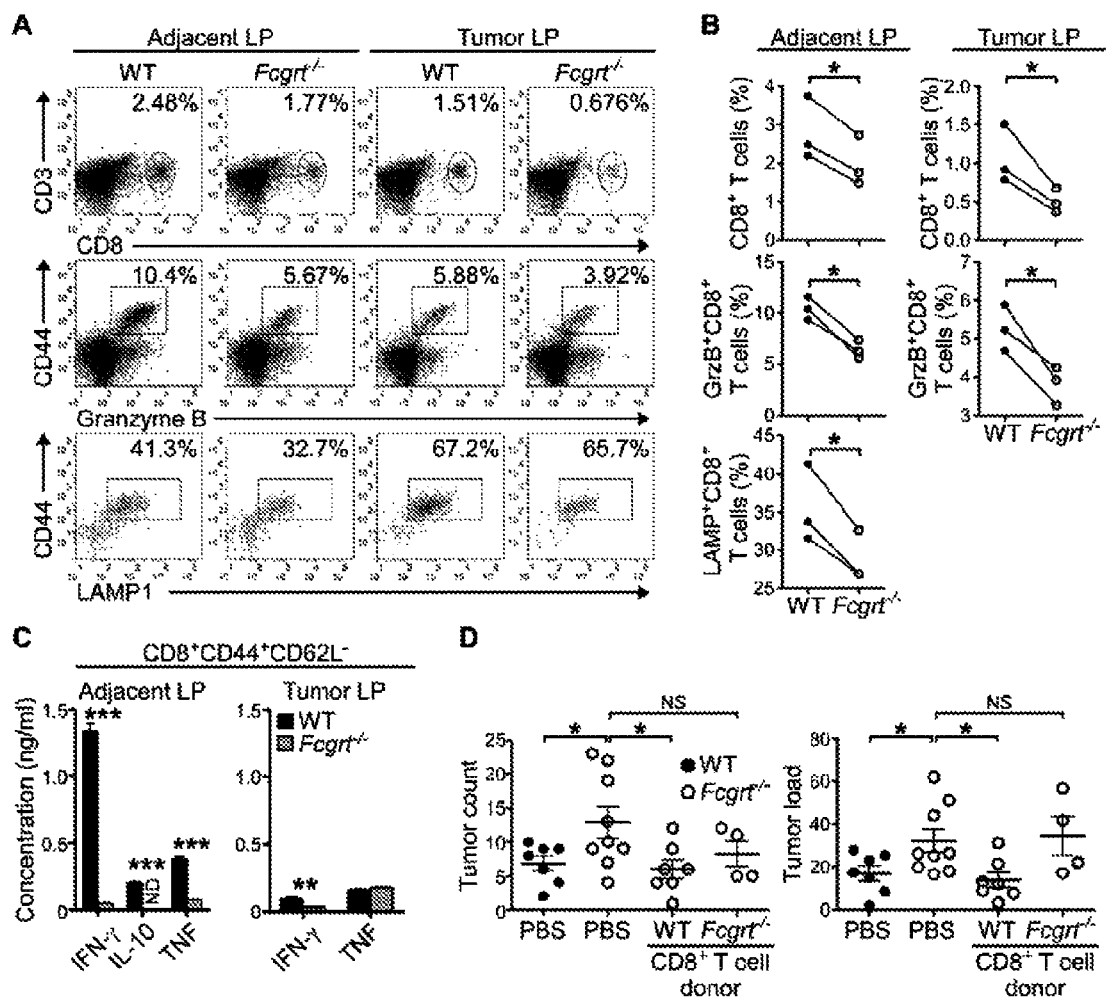
FIGS. 2A-2D depict, in accordance with various embodiments of the present invention that FcRn drives the activation and retention of tumor-reactive cytotoxic CD8+ T cells which confer tumor protection.
Figures 9A, 9B, 9C, 9D, 9E, 9F, 9G:
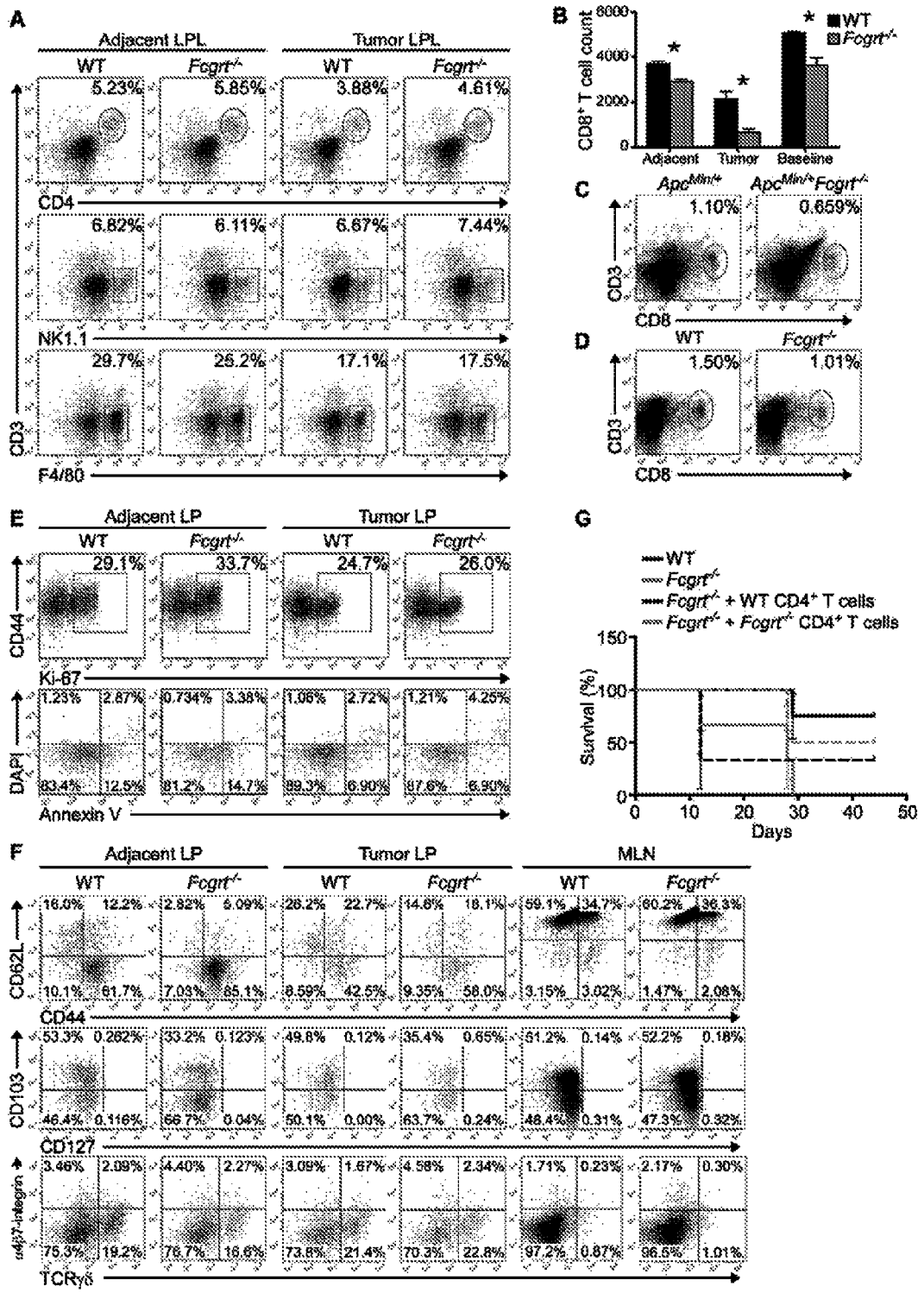
FIGS. 9A-9G depict, in accordance with various embodiments of the present invention that FcRn-mediated tumor immune surveillance is mediated by selective activation and retention of CD8$^+$ T cells in the intestinal LP.

FcRn Promotes the Retention and Activation of Tumor Protective CD8+ T Cells in the Large Intestine In seeking to better understand the nature of FcRn-driven anti-tumor immunity, we examined the immunological composition of LP lymphocytes (LPL) in both dissected tumors and macroscopically tumor-free adjacent tissue. While no differences were noted in the numbers of CD4+ T cells, natural killer (NK) cells or macrophages (FIG. 9A), significantly greater numbers of CD8+ T cells were consistently found both within tumor tissue and adjacent tissue of WT AOM/DSS-treated mice in comparison to their Fcgrt−/− littermates (FIGS. 2A, 2B, upper panels, and FIG. 9B). This same deficiency in CD8+ T cell infiltration into the tumor microenvironment of FcRn-deficient mice was also seen in ApcMin/+Fcgrt−/− animals in comparison to their ApcMin/+ littermates (FIG. 9C) as well as in Fcgrt−/− mice treated with AOM alone (FIG. 9D). Furthermore, a greater percentage of the CD8+ T cells from AOM/DSS treated WT animals expressed intracellular granzyme B or surface lysosomal associated membrane protein-1 (LAMP1) (FIGS. 2A, 2B, lower panels) than did those from their Fcgrt−/− littermates. We confirmed this using anti-CD3 and anti-CD28 restimulation of sorted effector CD8+CD44+CD62L− T cells from the LI of AOM/DSS-treated mice (FIG. 2C). CD8+ T cells from Fcgrt−/− tumor-bearing mice secreted only small amounts of interferon-γ (IFN-γ), tumor necrosis factor (TNF) and interleukin-10 (IL-10), the latter of which has recently been shown to be critical for efficient cytotoxic CD8+ T cell-mediated anti-viral and anti-tumor immunity (Mumm et al., 2011; Zhang and Bevan, 2011). While no differences were seen in the rates of CD8+ T cell proliferation or apoptosis, as assessed by Ki-67 and annexin V staining, respectively (FIG. 9E), both upregulation of CD103, an integrin associated with T cell retention (Le Floc'h et al., 2007), and increased expression of activation-associated CD44 on CD62L+CD8+ T cells were observed in CD8+ T cells infiltrating the LP of WT but not Fcgrt−/− littermates (FIG. 9F). This was specific for the tumor-associated tissues as these differences were not observed in the mesenteric lymph nodes (MLN) (FIG. 9F) and is notable because the presence of high numbers of CD8+CD44+CD62L+ cells bearing an effector memory (TEM) cell phenotype has been associated with improved prognosis in human CRC patients (Pages et al., 2005). These data are thus most consistent with a role for FcRn in driving anti-tumor immunity by promoting the retention and activation of cytotoxic T cells having homed to the LI.

We next sought to confirm that FcRn-mediated activation of CD8+ T cells was critical for its tumor protective function using adoptive transfer of CD8+ T cells isolated from the MLN and LP of AOM/DSS-treated WT or Fcgrt−/− mice into recipient Fcgrt−/− AOM/DSS-treated animals. By transferring CD8+ T cells isolated from both the MLN and total LI LP, we aimed to minimize the number of T cells likely to have been exposed to a tolerizing tumor microenvironment (Chen and Mellman, 2013). Fcgrt−/− recipient mice that received CD8+ T cells from WT donors developed significantly fewer tumors than non-T cell (PBS) treated control Fcgrt−/− mice (FIG. 2D). While the transfer of CD8+ T cells from Fcgrt−/− donors into Fcgrt−/− recipients did exert a non-significant decrease in tumor frequency compared to Fcgrt−/− controls, it also led to a significant increase in tumor size and thus of total tumor load, as measured by the total surface of the colon which was neoplastic (FIG. 2D) (Grivennikov et al., 2012). Similar experiments performed with adoptively transferred CD4+ T cells revealed that CD4+ T cells are not sufficient for FcRn-mediated tumor protection. Rather, our data are consistent with activation of cytotoxic CD8+ T cells being a primary mechanism by which FcRn-driven tumor immune surveillance operates.

Example 4

FcRn-Dependent Cross Priming by Dendritic Cells Induces Effective Anti-Tumor CD8+ T Cell Responses In light of our recent demonstration that FcRn in CD8−CD11b+ DC, in which the acidic endosomal and phagosomal pH favor FcRn-IgG binding, drives the cross-presentation of IgG IC-delivered antigens and the resulting activation of CD8+ T cells (Baker et al., 2011), which lack FcRn, we sought to determine whether FcRn-dependent cross-priming by DC was required for its anti-tumor effects. Given that this mechanism would necessitate the presence of tumor-reactive IgG to form IC and that tumor-reactive IgG has previously been documented in human CRC (Auer et al., 1988; Kijanka et al., 2010), we first confirmed the presence of these effector molecules in our model. Both ELISA (FIGS. 3A and 10A) and Western blotting (FIG. 10B) assays using IgG-depleted tumor epithelium lysates from AOM/DSS-treated mice verified that tumor-reactive IgG was present in the serum as well as in MLN and LI tissue homogenates of AOM/DSS-treated WT and Fcgrt−/− littermates but not non-tumor bearing controls. We also noted increases of similar magnitude in anti-phosphatidylserine and anti-cardiolipin IgG, which could promote the formation of IC containing apoptotic bodies or mitochondria released by dying tumor cells (Kepp et al., 2009), in the serum of both WT and Fcgrt−/− littermates (FIG. 10C). Moreover, both tumor-reactive IgG (FIGS. 3A and 10A) and total IgG (FIG. 10D) were also present at similar levels in the MLN and intestinal tissues of AOM/DSS-treated WT and Fcgrt−/− mice. Thus, although FcRn is critically important in protecting circulating IgG from catabolism and our Fcgrt−/− mice were predictably systemically hypogammaglobulinemic (FIG. 10D) (Roopenian et al., 2003), this was not the case in tissues for either total IgG (FIG. 10D) or tumor-specific IgG (FIG. 3A) where local IgG production by resident plasma cells is likely sufficient to normalize tissue IgG levels. Thus, the extreme susceptibility of Fcgrt−/− mice to tumor development cannot simply be attributed to a local deficiency in the IgG ligand for FcRn.

Having confirmed the presence of IgG capable of binding tumor antigens in both WT and Fcgrt−/− mice, we verified that there were no differences in the distribution of DC subsets or DC FcγR expression in the LI LP of WT and Fcgrt−/− littermates (FIG. 10E). This was particularly important given that FcRn-dependent cross-presentation requires FcγR for the initial IgG IC internalization (Baker et al., 2011). Evaluation of the functional characteristics of sorted CD8−CD11b+ and CD8+CD11b−− DC from the MLN, adjacent, and tumor tissues of AOM/DSS-treated mice revealed that Fcgrt−/− mice were significantly deficient in the production of cytokines (IFN-γ, IL-12) and transcription factors (T-bet) known to drive effective cytotoxic T cell-mediated immunity (FIG. 3B) (Garrett et al., 2009; Gerosa et al., 1996; Trinchieri, 2003; Zhang and Bevan, 2011). These differences were greatest in the CD8−CD11b+ DC subset which are highly efficient at FcRn-dependent cross-presentation (Baker et al., 2011). Furthermore, analysis of whole tissue transcripts taken from the tumor and adjacent tissue of tumor-bearing mice (FIGS. 10E-10H) clearly demonstrated decreased transcripts at the tissue level of these pro-cytotoxicity cytokines in FcRn-deficient animals. These data thus indicate that FcRn within DC is required for the establishment of a tissue level cytokine environment within the LI that is conducive to effective CD8+ T cell activation.

Figures 3A, 3B, 3C, 3D, 3E, 3F, 3G:
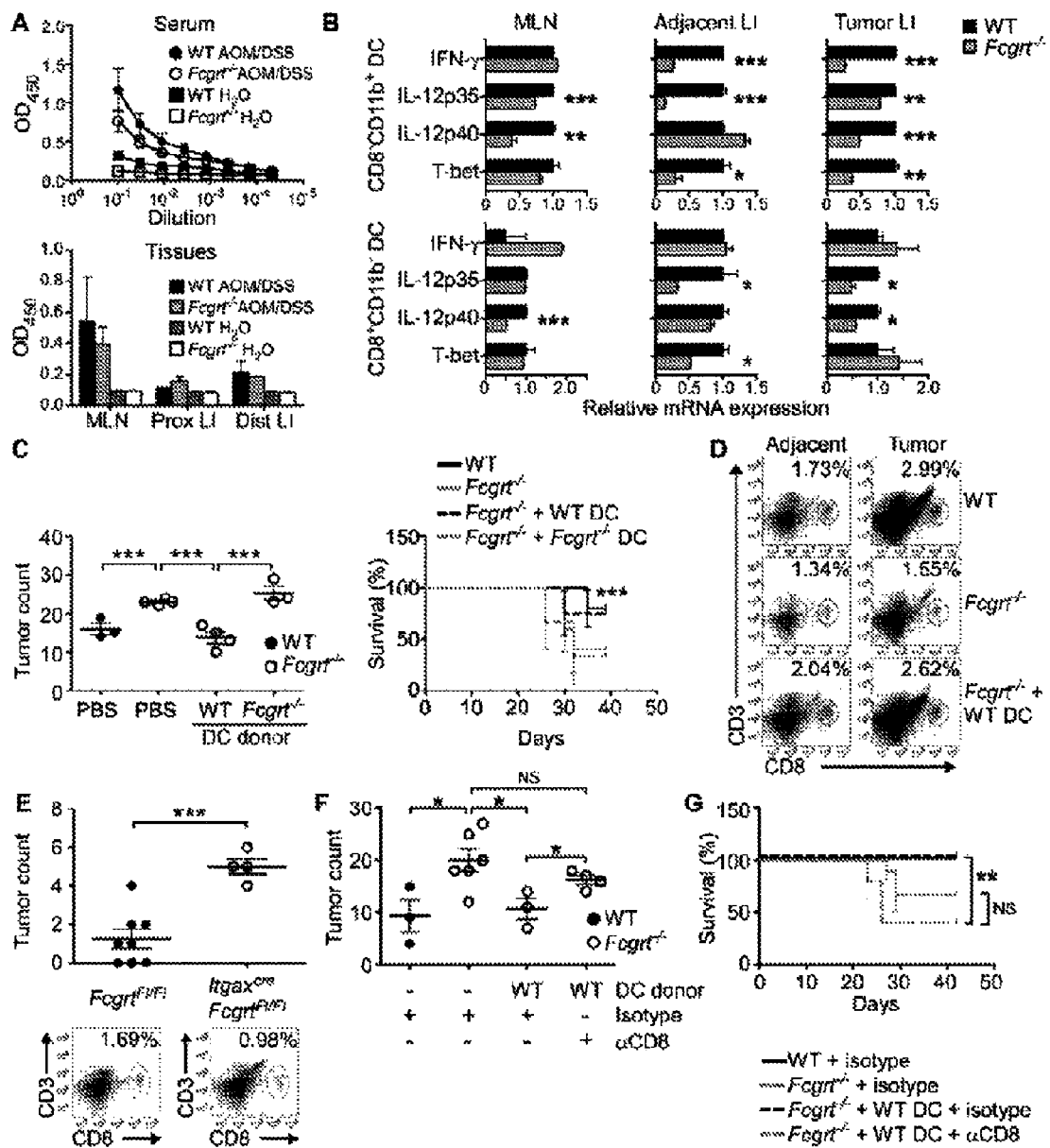
FIGS. 3A-3G depict, in accordance with various embodiments of the present invention that CD8-CD11b+ DC utilize FcRn to efficiently prime protective anti-tumor CD8+ T cell responses.

In order to demonstrate that FcRn-sufficient DC were directly involved in driving anti-tumor immunity, we first conducted a series of adoptive transfer experiments. Fcgrt−/− mice receiving CD8−CD11b+ DC (FIG. 10I) from AOM/DSS treated WT donors developed significantly fewer tumors than control PBS-treated Fcgrt−/− mice or Fcgrt−/− mice given Fcgrt−/− DC (FIG. 3C, left) despite equivalent homing and persistence of donor DC from both genotypes (FIG. 10J). Furthermore, administration of WT DC, but not Fcgrt−/− DC, protected Fcgrt−/− recipients from AOM/DSS-induced mortality (FIG. 3C, right). The transfer of even a small number of FcRn-sufficient WT CD8−CD11b+ DC was able to normalize the infiltration of CD8+ T cells into adjacent and tumor LI tissue of Fcgrt−/− mice (FIG. 3D), thereby confirming that no primary defect in CD8+ T cells is operating in Fcgrt−/− mice. Ex vivo assays on DC isolated from the MLN of Fcgrt−/− recipients 7 days after the transfer of WT DC further confirmed that FcRn-dependent cross-priming capacity had been restored (FIG. 10K). We validated these findings using mice bearing a foxed Fcgrt gene (FcgrtFl/Fl) (Montoyo et al., 2009) which were bred with Itgaxcre animals in order to specifically delete FcRn in DC (FIG. 10L). Treatment of ItgaxcreFcgrtFl/Fl mice with AOM/DSS induced significantly more colorectal tumors than were found in their FcgrtFl/Fl littermates (FIG. 3E). ItgaxcreFcgrtFl/Fl mice were also deficient in LI LP CD8+ T cell infiltration compared (FIG. 3E, bottom), thereby further supporting our hypothesis that FcRn specifically within DC could orchestrate CD8+ T cell activation within the intestine. We validated this by performing simultaneous DC transfer and CD8+ T cell depletion experiments which revealed that removal of CD8+ T cells from Fcgrt−/− recipients of WT CD8-CD11b+ DC undergoing AOM/DSS treatment abrogated the improvement in tumor incidence and cancer survival conferred by the WT DC (FIGS. 3F,G). These data thus confirm that an important mechanism of FcRn-mediated tumor protection is DC-dependent activation of CD8+ T cells via cross-priming of IgG IC-delivered tumor antigens and conditioning of the cytokine environment.

Example 5

Figures 4A, 4B, 4C, 4D, 4E, 4F:
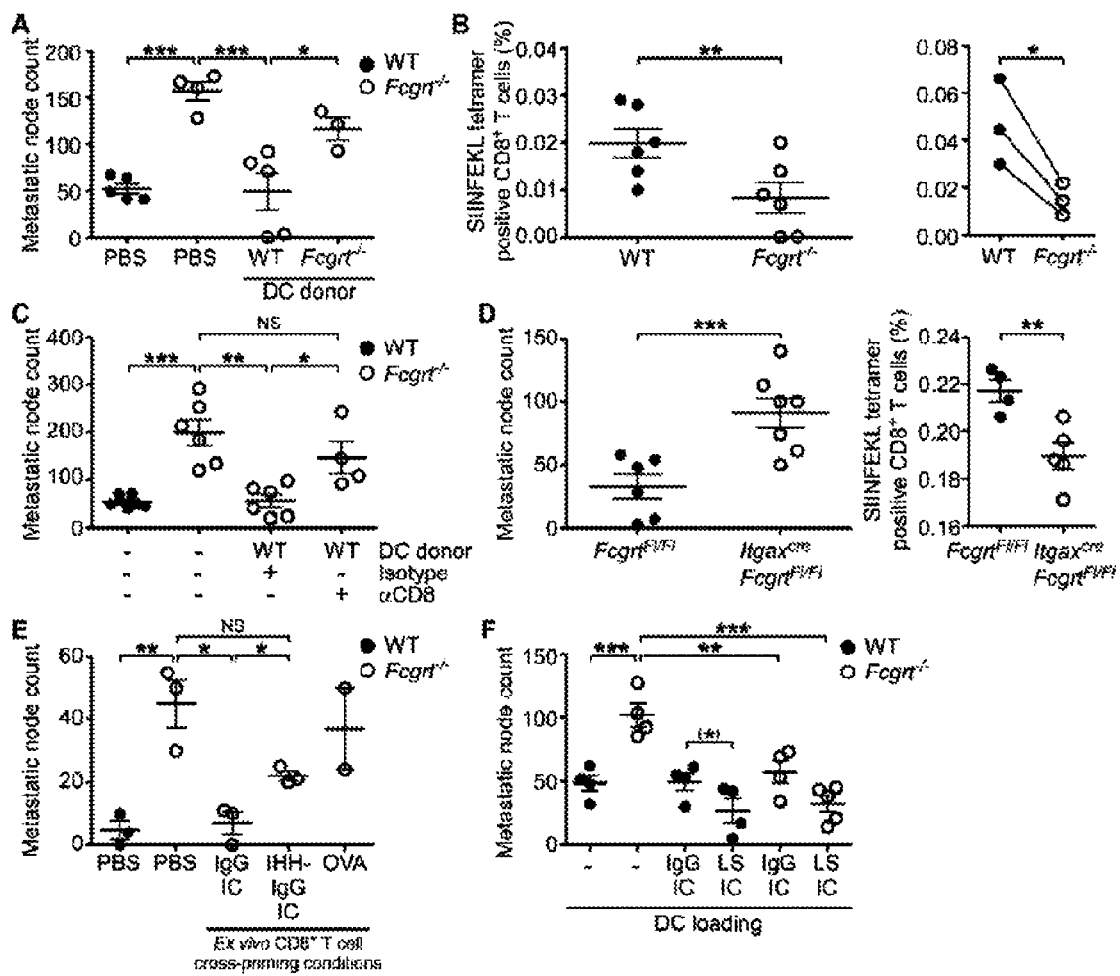
FIGS. 4A-4F depict, in accordance with various embodiments of the present invention that FcRn drives the induction of endogenous tumor-reactive CD8+ T cells and can be therapeutically targeted.
Figures 11A, 11B, 11C, 11D, 11E, 11F:
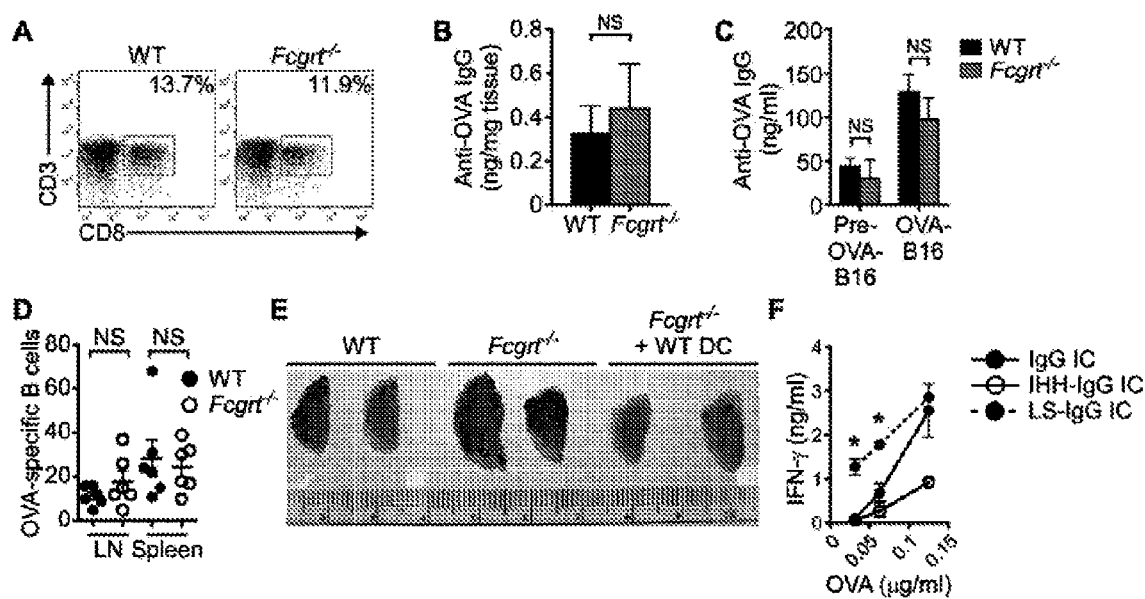
FIGS. 11A-11F depict, in accordance with various embodiments of the present invention that both CD8$^+$ T cells and tumor-specific IgG are required for FcRn-mediated protection from pulmonary metastases.

FcRn within DC Enables Activation of Endogenous CD8+ T Cells Towards Defined Cognate Tumor Antigens To confirm the individual components of FcRn-mediated tumor immune surveillance in an antigen specific system and demonstrate the effectiveness of targeting a single defined tumor antigen to an FcRn-enabled pathway, we used a pulmonary metastasis model using a melanoma cell line (B16) expressing the OVA antigen (OVA-B16) (Falo et al., 1995). Knowing that FcRn is highly expressed in the lung (Spiekermann et al., 2002), we first verified that the lungs of WT mice were enriched in CD8+ T cells in comparison to those of their Fcgrt−/− littermates (FIG. 11A). These data extend the range of FcRn-regulated mucosal CD8+ T cell responses to a second site which is frequently affected by cancer (Siegel et al., 2012) and is known to engage in both FcRn-dependent immune responses (Yoshida et al., 2004) and immunological crosstalk with the intestine (Keely et al., 2011). Subsequent to i.v. administration of OVA-B16, we observed a rise in anti-OVA IgG in lung homogenates and serum from both WT and Fcgrt−/− littermates (FIGS. 11B, 11C) and detected equivalent numbers of anti-OVA IgG-secreting B cells in the LN and spleens of WT and Fcgrt−/− mice (FIG. 11D), thereby confirming that there is no defect in the local production of tumor antigen-specific IgG in FcRn deficient animals. WT mice developed considerably fewer pulmonary nodules than Fcgrt−/− mice and subcutaneous vaccination at a distant site with WT DC, but not Fcgrt−/− DC conferred protection from pulmonary metastatic seeding to Fcgrt−/− recipients. (FIGS. 4A and 11E). Using SIINFEKL/H2kb tetramer staining, we established that a greater proportion of endogenous CD8+ T cells with OVA tumor antigen specificity arose in the lungs of WT mice receiving OVA-B16 tumor cells than in their Fcgrt−/− littermates (FIG. 4B). In order to confirm that DC-based, FcRn-mediated tumor protection was dependent upon activation of CD8+ T cells, we chronically administered a depleting anti-CD8 antibody to Fcgrt−/− recipients immunized with WT CD8−CD11b+ DC and given OVA-B16. Whereas the transfer of WT DC significantly decreased the incidence of metastatic pulmonary nodules in Fcgrt−/− recipients, this protection was abrogated by depletion of CD8+ T cells (FIG. 4C). We further confirmed that the main locus of FcRn-mediated tumor immune surveillance was the DC by showing that ItgaxcreFcgrtFl/Fl mice developed greater numbers of pulmonary nodules than did their FcgrtFl/Fl littermates and were less efficient in driving the expansion of tumor specific CD8+ T cells (FIG. 4D). These findings identify both endogenously arising tumor-reactive IgG and cognate endogenously derived CD8+ T cells as important components of the mechanism by which DC exert FcRn-dependent tumor immune surveillance.

We next sought to demonstrate that targeting FcRn-mediated cross-presentation with a single IgG-complexed tumor antigen could be a viable and attractive strategy for anti-tumor immunotherapy. In order to do so, we made use of a non-FcRn binding IHH-IgG containing three point mutations in the Fc domain which disable FcRn, but not Fcγ receptor, binding (Baker et al., 2011) and an enhanced FcRn binding LS-IgG containing the 'LS' mutation (M428L/ N434S), which increase FcRn binding while maintaining pH dependency (Claypool et al., 2004; Zalevsky et al., 2010). When OVA-reactive OT-I CD8+ cells were stimulated ex vivo with WT DC primed with OVA-containing IgG or IHH-IgG IC and adoptively transferred to Fcgrt−− recipient mice 24 h after i.v. administration of OVA-B16 cells, only CD8+ T cells primed by IgG IC-pulsed DC protected against the development of pulmonary metastases (FIG. 4E). Furthermore, immunizing mice with DC loaded with OVA-containing LS-IgG IC conferred significantly greater protection from metastasis development than did immunization with DC loaded with IgG IC (FIG. 4F). This is consistent with our finding that LS-IgG IC was more potent than native IgG IC at inducing cross-priming of low dose antigen in vitro (FIG. 11F). Collectively, these data demonstrate that targeting the immunostimulatory potential of FcRn using complexes formed from a single defined tumor antigen and IgG or FcRn-binding-enhanced IgG is a tractable and effective anti-tumor therapeutic approach.

Example 6

Figures 5A, 5B, 5C, 5D, 5E, 5F, 5G:
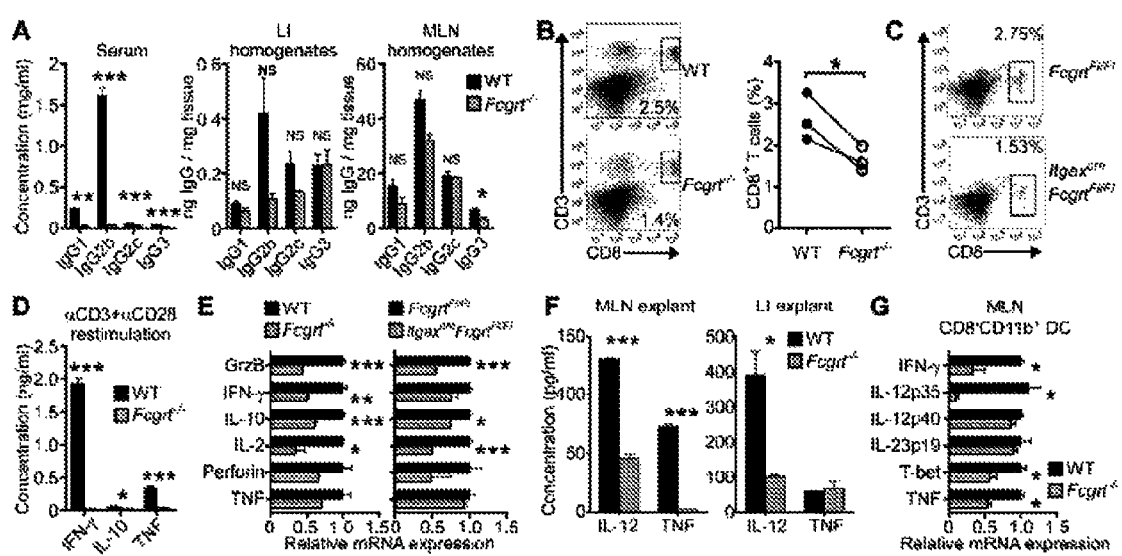
FIGS. 5A-5G depict depicts, in accordance with various embodiments of the present invention that FcRn within DC enables homeostatic CD8+ T cell activation and IL-12 production in the LI.

Dendritic Cell FcRn Enables Homeostatic CD8+ T Cell Activation and T1 Cytokine Secretion in the LI Our discovery of FcRn-mediated anti-tumor immunity arising in the LI in the absence of preexisting inflammation suggested that FcRn might be playing an active role in intestinal immune surveillance before the onset of cancer development and thus led us to investigate whether FcRn regulates CD8+ T cell activation in the LI under homeostatic conditions. Similar to our observation in AOM/DSS-treated mice, and despite the well-known differences in circulating IgG concentrations (Roopenian et al., 2003), similar quantities of IgG were present in the LI and MLN tissue of both WT and Fcgrt−/− littermates under steady-state conditions (FIG. 5A). These results confirmed that the susceptibility of Fcgrt−/− mice to tumor development could not be attributed to homeostatic local IgG deficiency. In spite of these comparable tissue IgG amounts, however, the LI LP of WT mice contained greater quantities of CD8+ T cells, but not other lymphocyte subsets, relative to that observed in Fcgrt−/− mice (FIG. 5B). A similar deficiency in CD8+ T cell infiltration into the LI LP was present in untreated ItgaxcreFcgrtFl/Fl mice compared to their littermate controls (FIG. 5C). Moreover, CD8+ T cells from the LI LP of WT mice secreted more IFN-γ, IL-10 and TNF upon restimulation in comparison to T cells obtained from Fcgrt−/− littermates (FIG. 5D) and expressed more activation and cytotoxicity associated cytokines when assessed immediately after isolation (FIG. 5E). Adoptive transfer of congenic CD8+ T cells into WT and Fcgrt−/− recipients indicated that not only did a greater number of transferred T cells accumulate in the LI LP of WT mice 10 days after transfer but that these also upregulated significantly more of the activation marker CD44 (FIG. 12A), consistent with our findings of deficient CD8+CD44+CD62L+ T cells in Fcgrt−/− tumor-bearing mice (FIG. 9F). In contrast, CD8+ T cells from WT or Fcgrt−/− donors transferred to congenic WT recipients homed equally well to the LI LP (FIG. 12B), thereby confirming that the effect of FcRn is within the local tissue microenvironment rather than being intrinsic to the T cells.

Figures 12A, 12B, 12C, 12D, 12E:
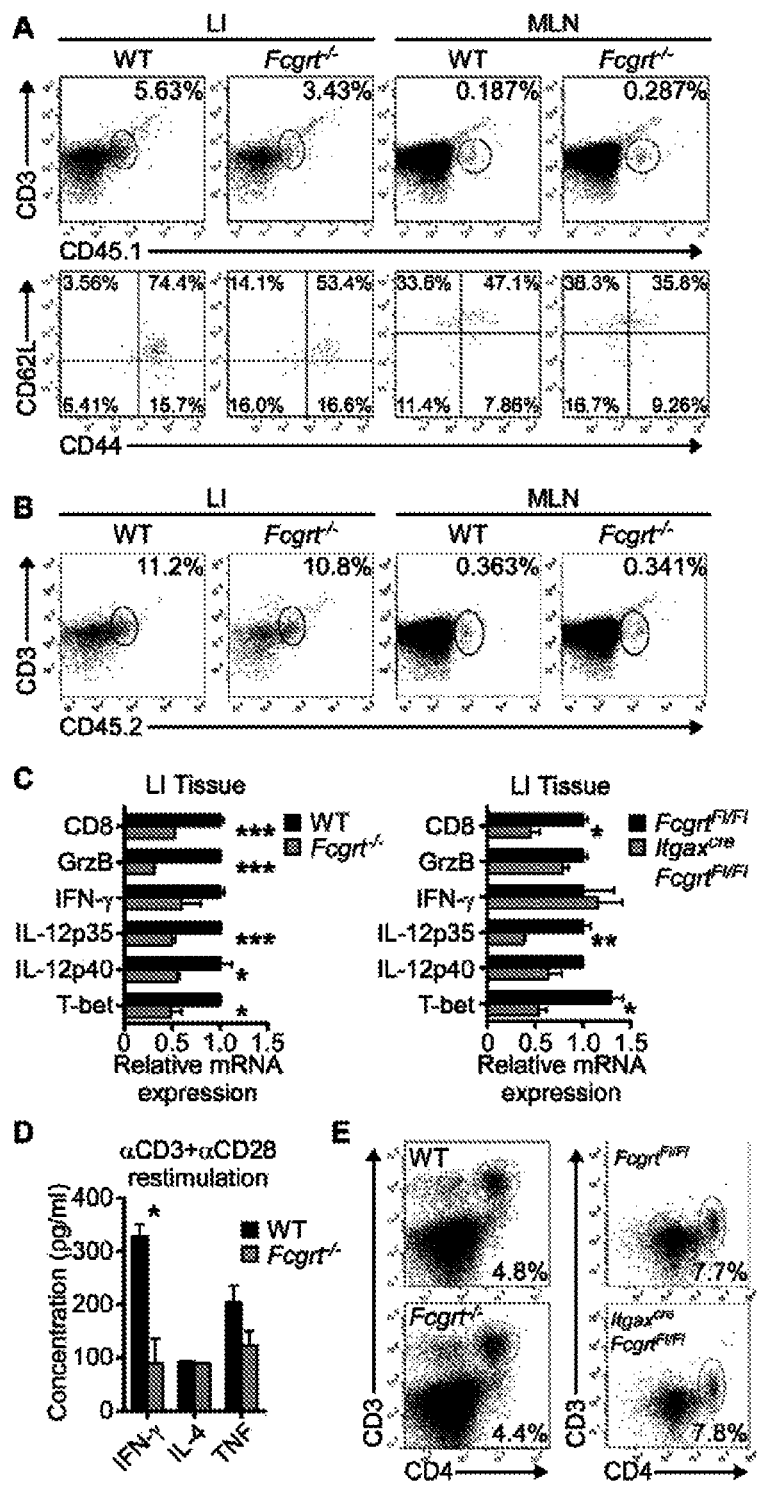
FIGS. 12A-12E depict, in accordance with various embodiments of the present invention that FcRn in DC drives homeostatic local activation of CD8$^+$ T cells and the Th1 polarization of CD4$^+$ T cells within the LI LP by facilitating the production of Tc1 and Th1 polarizing cytokines.

Given that efficient CD8+ T cell activation requires an appropriate cytokine environment, we next examined the local tissue cytokine milieu of Fcgrt−/− mice under homeostatic conditions (Gerosa et al., 1996; Zhang and Bevan, 2011). Tissue explant cultures (FIG. 5F) and analysis of tissues RNA transcripts (FIG. 12C) indicated that in the absence of FcRn, the MLN and LI were deficient in their ability to produce cytotoxicity-promoting IL-12 and TNF. By examining the cytokine profiles of sorted DC from the MLN of untreated WT and Fcgrt−/− littermates, we observed a similar dependence for FcRn on the expression of IFN-γ, IL-12p35, T-bet and TNF, but not IL-23p19, in CD8−CD11b+ DC (FIG. 5G). This suggests that FcRn within the CD8−CD11b+ subset of tissue-associated DC is responsible for establishing a cytokine milieu conducive to CD8+ T cell activation and thus promoting tumor immune surveillance in the LI. Similarly, CD4+ T cells from the LI of untreated Fcgrt−/− mice were deficient in secretion of Th1 cell-associated cytokines upon anti-CD3 and anti-CD28 re-stimulation despite being present in equal amounts in WT and Fcgrt−/− mice (FIGS. 12D, 12E). These data suggest that IgG IC ligation of FcRn in DC contributes to the establishment of homeostatic Th1 and T cytotoxic-1 (Tc1) cell polarization as well as CD8+ T cell function in the LI.

Example 7

Multimeric IgG IC Ligation of FcRn in DC Induces the Production of IL-12

Figures 6A, 6B, 6C, 6D, 6E, 6F:
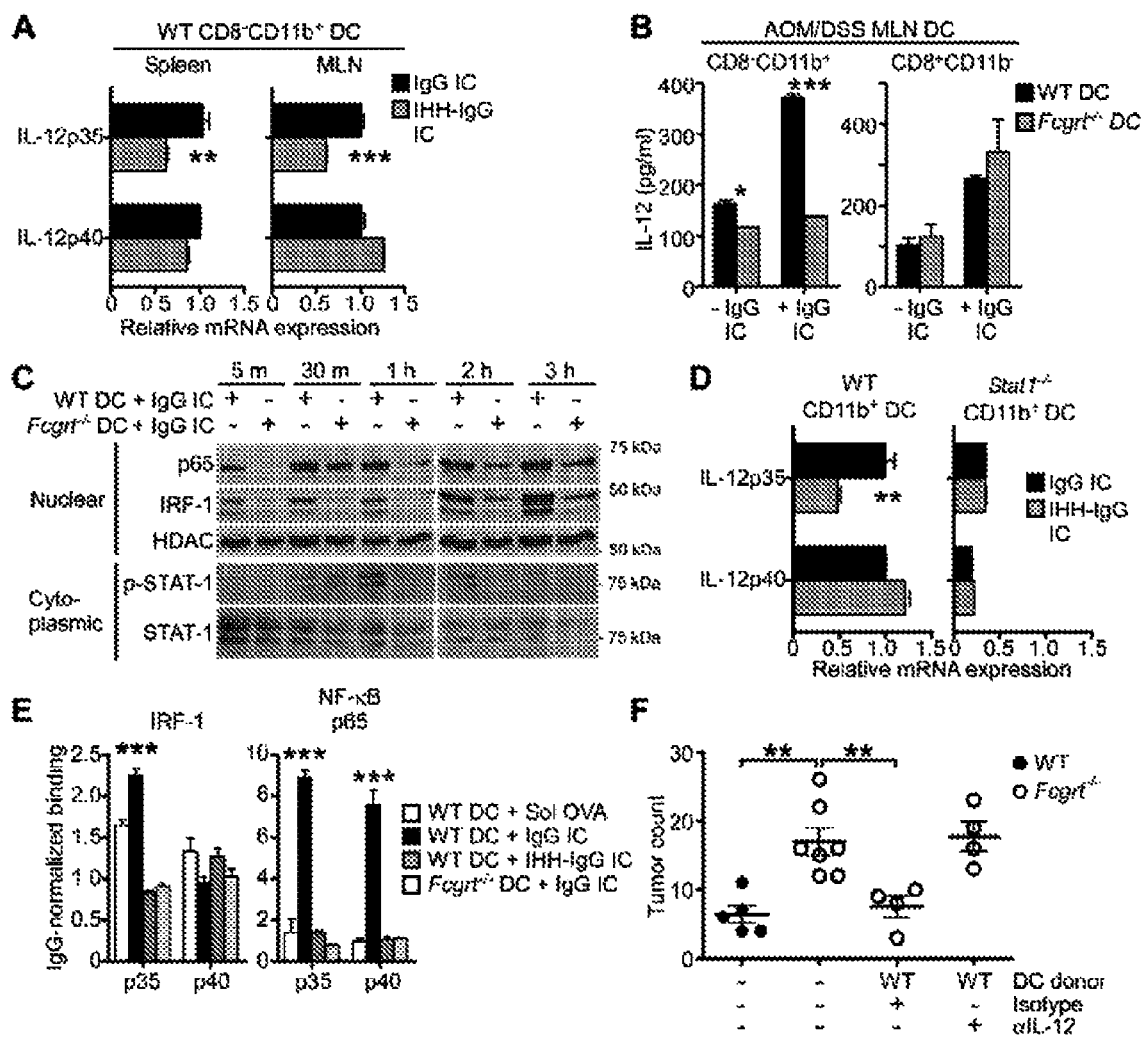
FIGS. 6A-6F depict, in accordance with various embodiments of the present invention that IgG IC ligation of FcRn in CD8-CD11b+ DC induced IL-12 production via activation of a signaling cascade.

Knowing that IL-12 is a potent enhancer of CD8+ T cell-mediated immunity (Gerosa et al., 1996; Trinchieri, 2003) and having consistently observed greater quantities of IL-12 in DC, particularly the CD8−CD11b+ subset, from the mucosal tissues of WT compared to Fcgrt−/− littermates, we next investigated the effects of ligation of FcRn by IgG IC or IgG IC incapable of binding FcRn (IHH-IgG IC) on IL-12 secretion. Incubation of WT CD8−CD11b+ DC from the MLN and spleen of untreated WT mice with FcRn binding IgG IC, but not FcRn-non-binding IHH-IgG IC, led to the direct induction of IL-12p35 transcripts (FIG. 6A). Similarly, IgG IC stimulation of WT but not Fcgrt−/− CD8−

Figures 13A, 13B, 13C:
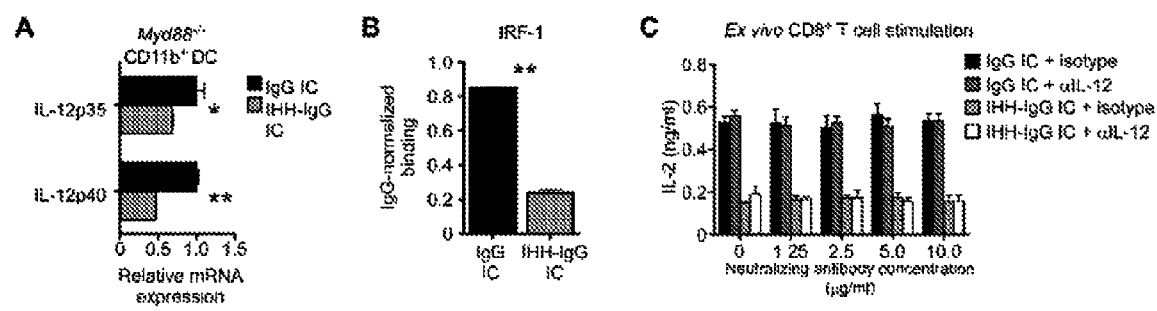
FIGS. 13A-13C depict, in accordance with various embodiments of the present invention that FcRn-dependent induction of IL-12 is not dependent on MYD88 and is not required for FcRn-mediated cross-priming (FIG. 13A) Induction of IL-12p35 upon ex vivo stimulation of Myd88$^{-/-}$ CD8$^-$CD11b$^+$ DC with FcRn-binding IC (IgG IC) or FcRn non-binding IC (IHH-IgG IC) for 6 h.

CD11b+ DC isolated from the MLN of AOM/DSS treated mice resulted in increased IL-12 secretion (FIG. 6B). We observed that stimulation of Fcgrt–/– DC with IgG IC led to considerably less phosphorylation of the Th1 cell-associated transcription factor STAT-1 (Antonios et al., 2010) than was seen in WT DC (FIG. 6C). We confirmed that STAT-1 activation was an important component of FcRn-induced IL-12 production by treating CD8–CD11b+ DC isolated from Stat1–/– mice with FcRn-binding IgG IC and FcRn-non-binding IHH-IgG IC and observing that IgG IC failed to induce IL-12p35 in the absence of STAT-1 (FIG. 6D). We further showed that (Liu et al., 2003; Murphy et al., 1995) stimulation of WT CD8–CD11b+ DC with IgG IC led to significantly greater nuclear translocation and IL-12p35 promoter binding of both interferon regulatory factor-1 (IRF-1) and NF-κB p65 than was observed in Fcgrt–/– DC or upon stimulation with IHH-IgG IC (FIGS. 6C, 6E) and confirmed that this was MYD88 independent (FIGS. 13A, 13B). IgG IC ligation of FcRn in DC is thus able to directly induce the production of the potent Th1 and Tc1 cell-associated cytokine IL-12.

In order to demonstrate that FcRn-mediated induction of IL-12 by DC contributes to the ability of this receptor to promote anti-tumor immune surveillance, we next performed an IL-12 neutralization experiment in which Fcgrt–/– mice adoptively transferred with WT DC were subjected to AOM/DSS treatment in the presence of a neutralizing anti-IL-12 antibody or isotype control (Wysocka et al., 1995). Whereas WT DC were able to decrease the incidence of colorectal tumors in Fcgrt–/– recipients down to the numbers seen for WT control mice, this protection was completely abrogated when mice were treated with anti-IL-12 (FIG. 6F). However, in vitro co-culture assays demonstrated that FcRn-dependent CD8+ T cell priming was independent of IL-12 production (FIG. 13C) indicating that the cross-presenting and cytokine inducing functions of FcRn are independent of each other. Collectively, these data indicate that FcRn-driven DC-mediated tumor protection results from a dual ability to promote cross-presentation of IgG IC-delivered antigen to CD8+ T cells as well as to induce secretion of IL-12 which, notably, can augment the cytotoxic capacity of the primed T cells.

Example 8

FcRn Expressing DC Predict Survival in Human CRC and Secrete FcRn-Dependent IL-12

Figures 7A, 7B, 7C, 7D, 7E, 7F:
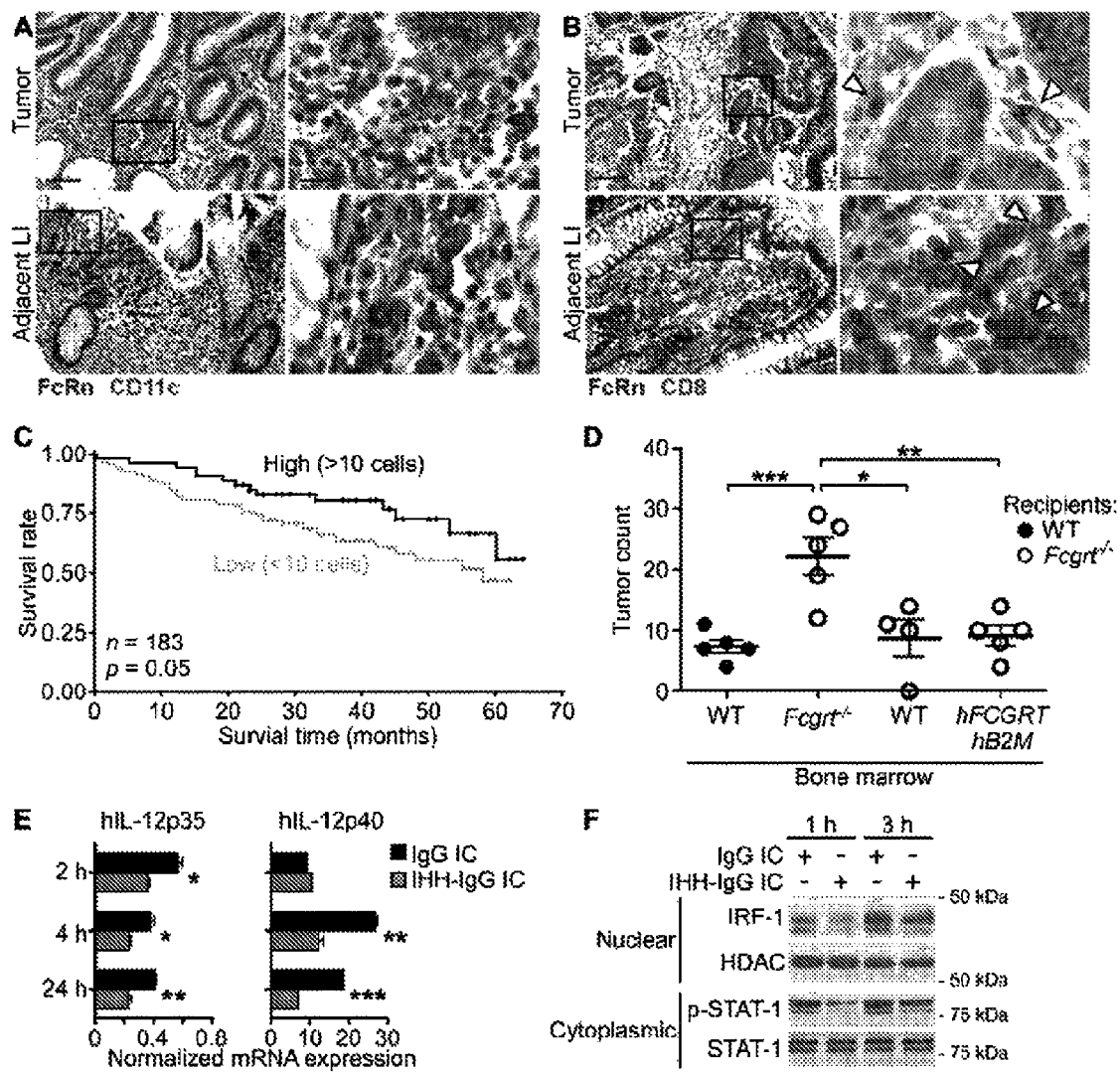
FIGS. 7A-7F depict, in accordance with various embodiments of the present invention that FcRn expressing DC predict survival in human CRC and secrete IL-12 upon FcRn stimulation.
Figures 14A, 14B, 14C, 14D, 14E, 14F, 14G, 14H:
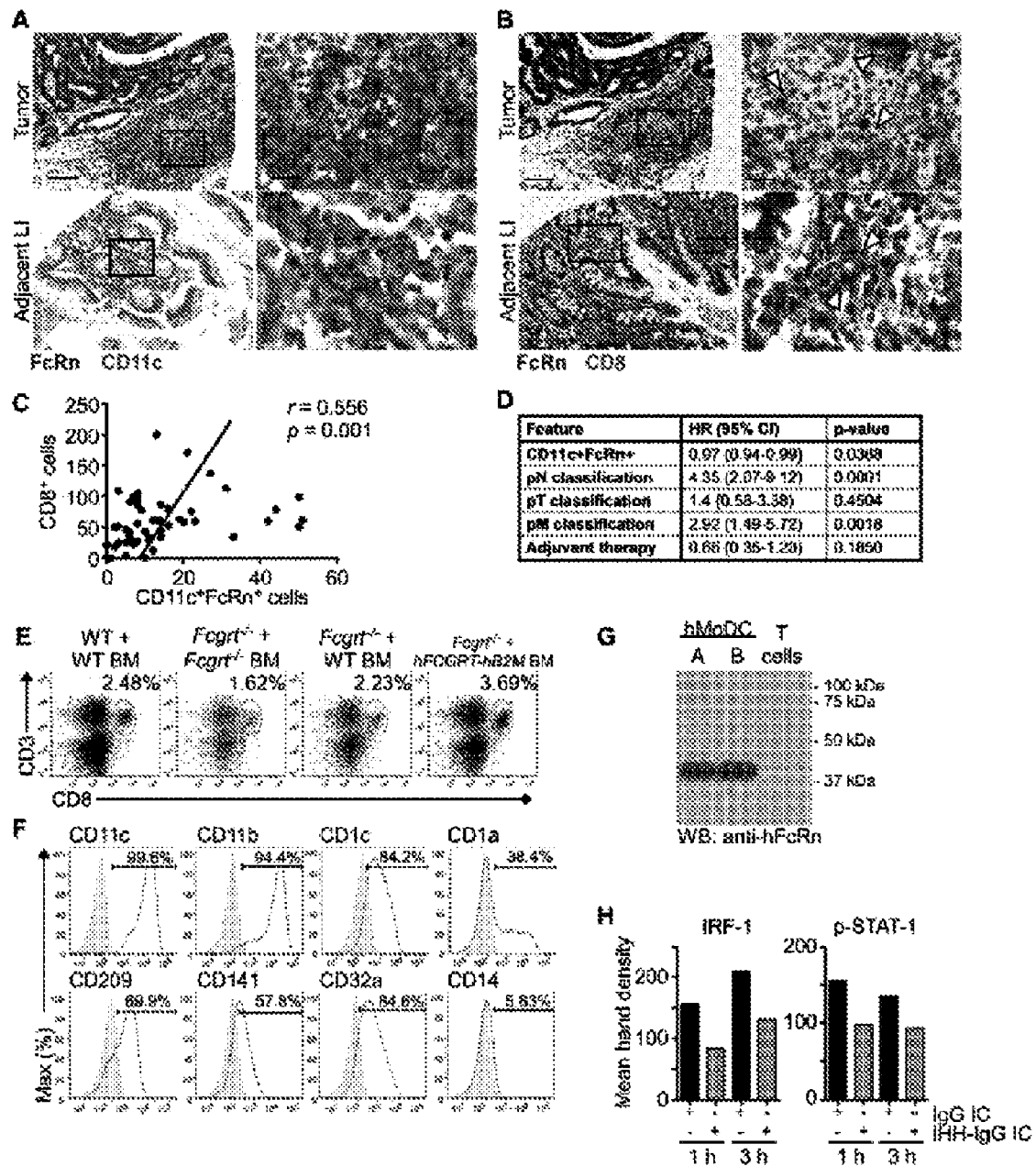
FIGS. 14A-14H depict, in accordance with various embodiments of the present invention that human DC strongly express FcRn and localize to the stroma of both normal and CRC-associated LI.

To definitively establish that our observations in mice were relevant to the development of human CRC, we evaluated the presence of FcRn-expressing DC in 50 cases of human CRC and matched adjacent normal tissue utilizing immunohistochemical staining for FcRn and CD11c. As shown in FIGS. 7A and 14A, FcRn+CD11c+ cells were clearly present in the stroma of both tumor LI (upper panels) and adjacent normal LI (lower panels) of CRC patients. Furthermore, a direct interaction of FcRn+ stromal cells with CD8+ T cells was observed in both tumor LI (upper panels) and CRC-adjacent normal LI (lower panels) (FIGS. 7B and 14B). Importantly, the frequency of FcRn+CD11c+ DC correlated positively with the presence of CD8+ T cells in the CRC-adjacent normal stroma (FIG. 14C). In order to determine if the presence of FcRn+CD114c+ cells in the tumor microenvironment had an impact on patient survival, we stained a well characterized tissue microarray of 183 human CRC cases for these cells and analyzed their impact on disease outcome. Kaplan-Meier survival curves indicated that patients with ≥10 FcRn+CD11c+ cells per punch had significantly longer survival times over a 70 month follow up than did those with <10 FcRn+CD11c+ cells (FIG. 7C). Furthermore, increasing numbers of FcRn+CD11c+ cells were found to have a positive effect on patient survival in univariate proportional hazard analysis (p=0.0333), an effect which was maintained in a multivariable analysis (p=0.0388) when adjusting for the indicated clinical parameters (FIG. 14D). Collectively, these studies demonstrate that FcRn-expressing DC localize to both the CRC and CRC-associated adjacent microenvironment, correlate with the infiltration of CD8+ T cells into the tumor tissue and predict improved prognosis for CRC patients.

In order to demonstrate a direct causative link between human FcRn and anti-tumor immune surveillance, we generated chimeric mice in which irradiated Fcgrt–/– recipients were reconstituted with bone marrow from donors that were either WT, Fcgrt–/– or expressed human FcRn and β2-microglobulin (β2M) on an Fcgrt–/– background (hFCGRT-hB2M-mFcgrt–/–) and thus possess only the human form of the receptor (Roopenian et al., 2003). When the chimeras were subjected to AOM/DSS treatment, Fcgrt–/– mice reconstituted with Fcgrt–/– bone marrow developed far greater numbers of colorectal tumors than did Fcgrt–/– mice reconstituted with either WT or hFCGRT-hB2M-mFcgrt–/– bone marrow (FIG. 7D). Furthermore, CD8+ T cell infiltration in the LI LP of tumor-bearing mice was restored to WT levels in Fcgrt–/– mice possessing human-FcRn expressing hematopoietic cells (FIG. 14E). Thus, human FcRn is equally as capable of orchestrating anti-tumor immune surveillance as is its murine ortholog.

We lastly sought to confirm that the intracellular mechanisms we had demonstrated in mouse DC were also operative in their human equivalents using human monocyte-derived DC (hMoDC), which phenotypically akin to the murine CD8–CD11b+ DC subset which engage in efficient FcRn-dependent cross-priming (FIGS. 14F, 14G) (Baker et al., 2011; Collin et al., 2011). As shown in FIG. 7E, stimulation of hMoDC by IgG IC leads to greater production of both IL-12p35 and IL-12p40 than stimulation with non-FcRn-binding IHH-IgG IC. Furthermore, IgG IC induced greater phosphorylation of STAT-1 and nuclear translocation of IRF-1 after both 1 h and 3 h than did IHH-IgG IC (FIGS. 7F and 14H). Together, they support the importance of human FcRn function in DC in enabling anti-tumor immunity through its ability to regulate IL-12 production and CD8+ T cell activation.

Example 9

Figures 15A, 15B:
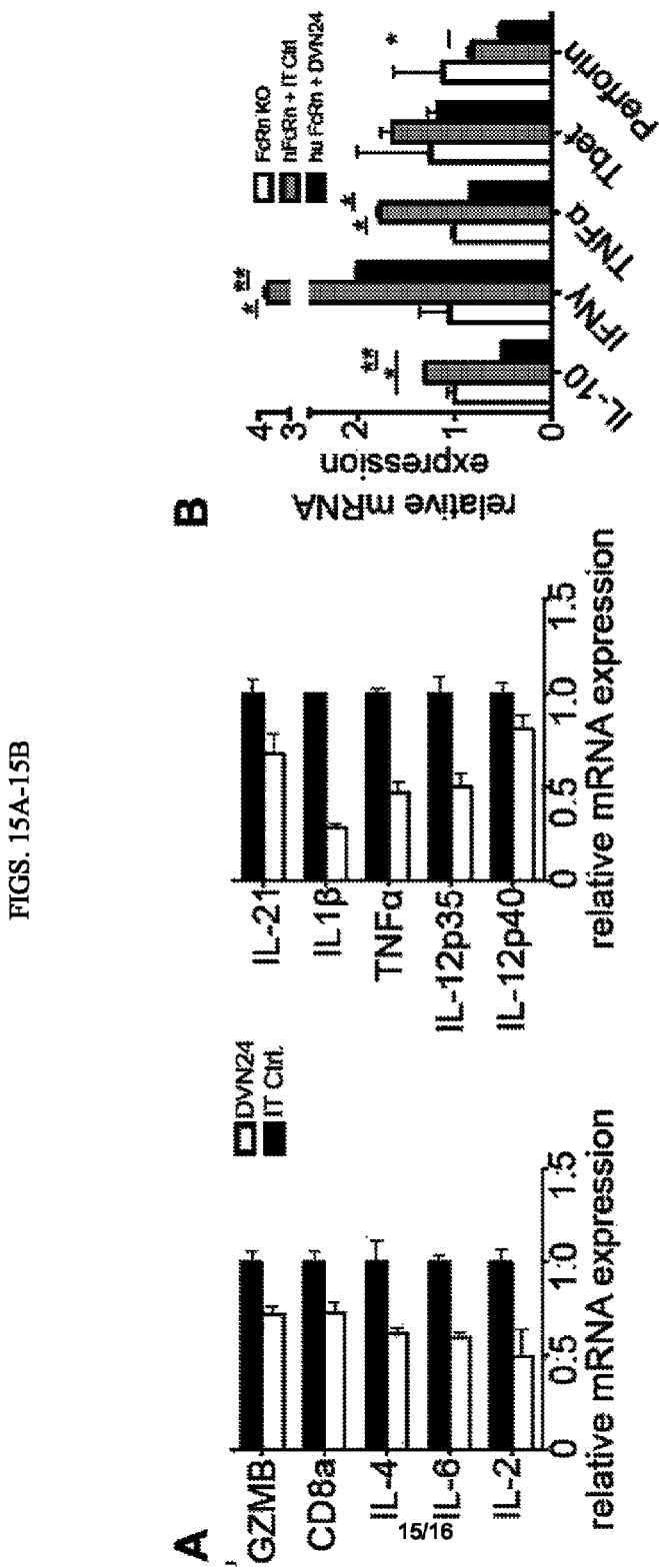
FIGS. 15A-15B depict, in accordance with various embodiments of the present invention that antibody mediated blockade of FcRn decreases Th1 cytokine transcript levels during IgG-mediated colitis.
Figure 16:
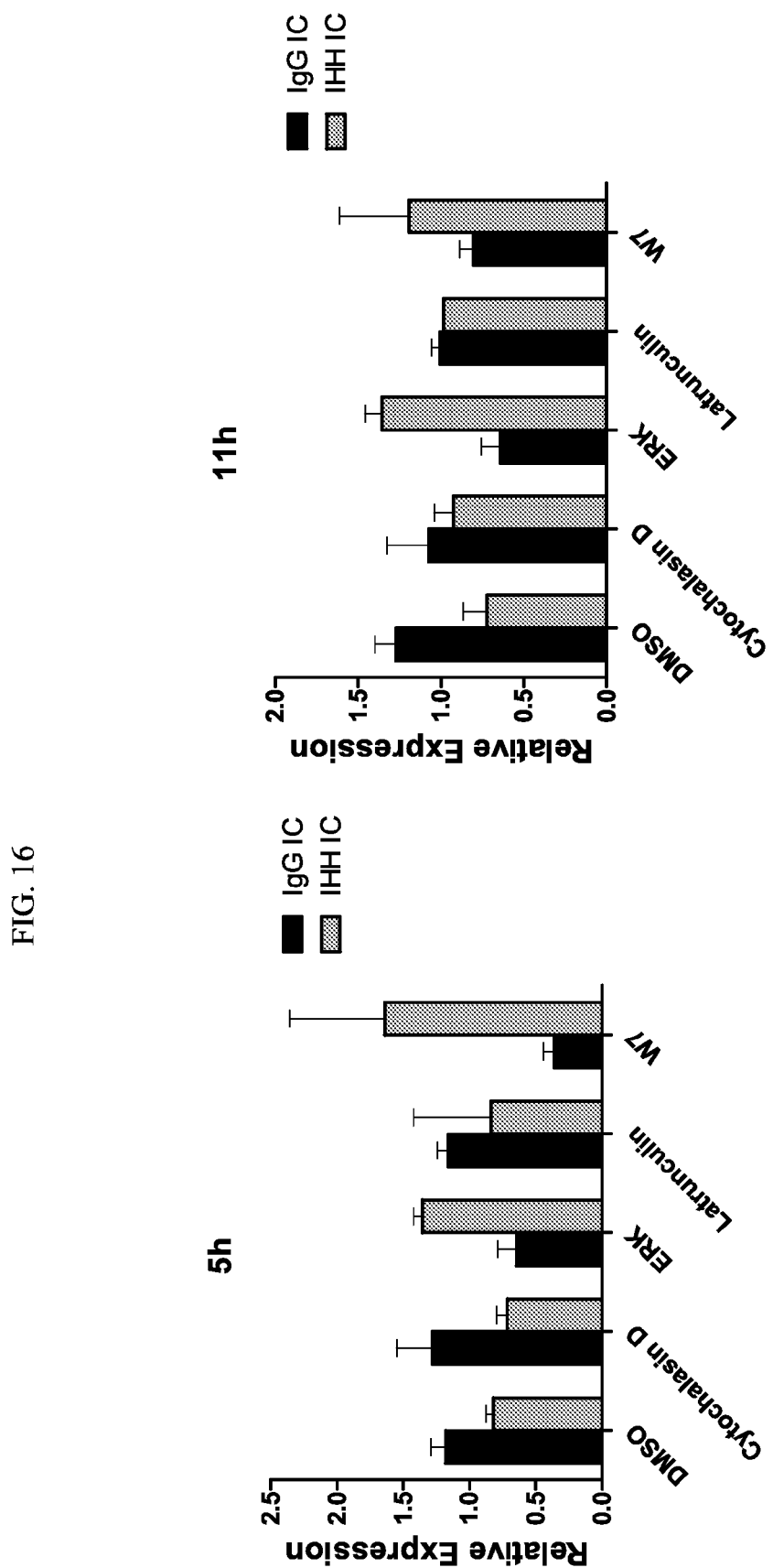
FIG. 16 depicts, in accordance with various embodiments of the present invention, FcRn-mediated upregulation of IL-12p35 is dependent upon ERK and calmodulin but not cytoskeletal rearrangements. Primary mouse dendritic cells were stimulated with IgG containing immune complexes against chicken ovalbumin that were wild type and able to bind FcRn or mutant and unable to bind FcRn (IHH-IC) due to three mutations in the Fc domain of IgG. RNA was isolated after 5 or 11 hours from such cells treated with inhibitors for cytoskeleton (cytochalasin D and Latrunculin), calmodulin (W7) or ERK. The RNA was reverse transcribed and IL-12p35 was quantified by qPCR.

As shown in FIG. 15, blockade with the FcRn specific monoclonal antibody DVN24 decreases the levels of Th1 cytokines.

The findings presented here identify a key physiological role for FcRn-mediated cross-priming in driving homeostatic activation of CD8+ T cells and in CD8+ T cell-mediated anti-tumor immune surveillance in the LI and lung. We have clearly established in multiple tumor models that genetic deletion of FcRn increases susceptibility to carcinogenesis at these mucosal sites. Transfer of CD8+ T cells primed under FcRn-sufficient conditions or of WT FcRn-bearing DC was capable of rescuing FcRn-deficient animals from both a high tumor burden and tumor-induced mortality. This depended upon IgG IC-mediated ligation of FcRn within mucosal DC which enabled the priming of tumor antigen-specific endogenous CD8+ T cells via its dual induction of antigen cross-presentation and the production of immune-enhancing cytokines such as IL-12. We have also demonstrated the human relevance of our findings by demonstrating that FcRn-expressing human DC respond to IgG IC stimulation with the production of cytotoxicity-promoting IL-12, that FcRn+DC localize to the CRC microenvironment where their ability to induce anti-tumor immunity contributes to improved patient survival and that human FcRn in hematopoietic cells can substitute for its mouse ortholog in protecting against the development of colorectal carcinoma. Our findings are furthermore consistent with a model in which IgG IC binding to FcRn within mucosal DC directs not only the intracellular trafficking of IgG IC but also the previously unrecognized organization of a signaling cascade which enhances the secretion of cytotoxicity-promoting cytokines. These features of FcRn biology uniquely enable potent anti-tumor immune surveillance requiring only small amounts of antigen and capable of overcoming the immunoregulatory environment characteristic of intestinal and, potentially, other mucosal tissues (MacDonald et al., 2011). Moreover, our demonstration that FcRn-deficiency does not result in decreased levels of tissue-associated IgG but rather diminished levels of CD8+ T cells and decreased CD8+ T cell function under homeostatic conditions further suggests that a major function of FcRn in tissues is in the regulation of cell mediated immunity rather than solely the protection of IgG from catabolism which is observed systemically.

An important prerequisite for FcRn-mediated tumor protection is the presence of IgG capable of recognizing a tumor antigen and initiating a cascade of FcRn-dependent anti-tumor responses which feed in to the recently described "Cancer-Immunity Cycle" (Brichory et al., 2001; Chen and Mellman, 2013; Desmetz et al., 2011). The presence of appreciable quantities of endogenous IgG autoantibodies reactive or cross-reactive towards altered or abnormally expressed tumor antigens is well documented and these are likely to serve as the initiators for FcRn-mediated tumor protection. Specifically, the accelerated release of tumor-associated antigens either alone or as part of cellular debris or apoptotic bodies caused by increased rates of tumor cell death (Kepp et al., 2009), will promote the formation of immune complexes with endogenous tumor-reactive or phospholipid-specific autoantibodies. Subsequently, the concomitant induction of IL-12 production resulting from FcRn ligation by IgG IC can be expected to amplify local FcRn-dependent anti-tumor immune responses even further since IL-12 itself is a potent inducer of humoral immunity (Metzger, 2010). A key physiological role for FcRn within DC therefore appears to be the integration of humoral and cellular adaptive immune responses capable of targeting mucosal malignancies and, undoubtedly, a host of intracellular microbial infections.

Several intriguing aspects of FcRn biology emerge from our work. The first of these is that FcRn-dependent immune regulation is operative under homeostatic conditions and is critical for establishing baseline colonic CD8+ T cell activation and function. We predict that such homeostatic responses are largely directed at microbial antigens given that IgG with antibacterial specificities are abundantly present in the intestine (Macpherson et al., 1996) and that the pathways described here may also play a critical role in immune surveillance against acute and chronic microbial infections (Yoshida et al., 2006) Secondly, our work highlights the differential role played by FcRn in different body compartments. Whereas FcRn is critical for maintaining IgG persistence within the circulatory system (Roopenian et al., 2003), our observations indicate that within tissues, FcRn is predominantly involved in the regulation of local immune responses. In addition to the inadequate immune activation seen in the intestines of Fcgrt−/− mice, this idea is supported by our findings that Fcgrt−/− mice were only minimally deficient in IgG quantities within tissues where equal amounts of IgG producing cells were able to compensate for the lack of FcRn-mediated IgG protection. Finally, we have demonstrated the feasibility and effectiveness of targeting FcRn-mediated anti-cancer immunosurveillance pathways using a single defined tumor antigen in complex with native IgG or IgG engineered for enhanced FcRn binding. In addition to enabling antigen specific CD8+ T cell mediated immunity after tumor onset, such therapies also have the potential to promote tumor immune surveillance in healthy high risk individuals by enhancing the baseline cytotoxic potential of the intestine. While a large body of knowledge exists pertaining to the dynamics of FcRn-IgG interaction (Vaughn et al., 1997) and the ability to engineer IgG with increased affinity for FcRn is currently available (Mi et al., 2008; Zalevsky et al., 2010), targeting of FcRn has yet to be exploited by current DC-based vaccination strategies (Tacken et al., 2007) despite the growing interest in DC antibody vaccines (Palucka and Banchereau, 2013).

The pleiotropic nature of FcRn and its wide-reaching influence on normal physiology remain poorly understood. Whereas the main function of FcRn systemically is the protection of monomeric IgG from catabolism (Roopenian et al., 2003), a major role in tissues, particularly mucosal tissues replete with IgG, appears to be one of immunological activation upon ligation by multimeric IgG IC. To this effect, FcRn participates in the organization not only of an antigen presentation cascade but also of a signaling cascade that is associated with innate effector immune function. As shown here, a major consequence of this role for FcRn is the efficient induction of anti-tumor immunity. These studies show that FcRn functions in anti-tumor immunity through the induction (via IL-12) and instruction (via cross-presentation) of CD8+ T cells. Developing a greater understanding of the nuances of FcRn-modulated immune activation, particularly at the tissue level where FcRn in dendritic cells promotes the immunogenic catabolism of IgG-complexed antigens, holds considerable promise for the development of new therapies against mucosal diseases.

REFERENCES

1. Antonios, D., Rousseau, P., Larange, A., Kerdine-Romer, S., and Pallardy, M. (2010). Mechanisms of IL-12 Synthesis by Human Dendritic Cells Treated with the Chemical Sensitizer NiSO4. J. Immunol 185, 89-98.
2. Aoki, K., Tamai, Y., Horiike, S., Oshima, M., and Taketo, M. M. (2003). Colonic polyposis caused by mTOR-mediated chromosomal instability in Apc+/delta716 Cdx2+/− compound mutant mice. Nat. Genet. 35, 323-330.
3. Arthur, J. C., and Jobin, C. (2011). The struggle within: Microbial influences on colorectal cancer. Inflamm. Bowel Dis. 17, 396-409.
4. Arthur, J. C., Perez-Chanona, E., Muhlbauer, M., Tomkovich, S., Uronis, J. M., Fan, T. J., Campbell, B. J., Abujamel, T., Dogan, B., Rogers, A. B., et al. (2012). Intestinal inflammation targets cancer-inducing activity of the microbiota. Science 338, 120-123.

5. Auer, I. O., Grosch, L., Hardorfer, C., and Roder, A. (1988). Ulcerative colitis specific cytotoxic IgG-autoantibodies against colonic epithelial cancer cells. Gut 29, 1639-1647.
6. Baker, K., Qiao, S.-W., Kuo, T. T., Aveson, V. G., Platzer, B., Andersen, J.-T., Sandlie, I., Chen, Z., de Haar, C., Lencer, W. I., et al. (2011). Neonatal Fc receptor for IgG (FcRn) regulates cross-presentation of IgG immune complexes by CD8−CD11b+ dendritic cells. Proc. Natl. Acad. Sci. U.S.A. 108, 9927-9932.
7. Brichory, F., Beer, D., LeNaour, F., Giordano, T., and Hanash, S. (2001). Proteomics-based Identification of Protein Gene Product 9.5 as a Tumor Antigen That Induces a Humoral Immune Response in Lung Cancer. Cancer Res. 61, 7908-7912.
8. Chen, Daniel S., and Mellman, I. (2013). Oncology Meets Immunology: The Cancer-Immunity Cycle. Immunity 39, 1-10.
9. Claypool, S. M., Dickinson, B. L., Wagner, J. S., Johansen, F. E., Venu, N., Borawski, J. A., Lencer, W. I., and Blumberg, R. S. (2004). Bidirectional transepithelial IgG transport by a strongly polarized basolateral membrane Fcgamma-receptor. Mol. Biol. Cell 15, 1746-1759.
10. Coghill, A. E., Newcomb, P. A., Poole, E. M., Hutter, C. M., Makar, K. W., Duggan, D., Potter, J. D., and Ulrich, C. M. (2012). Genetic Variation in Inflammatory Pathways Is Related to Colorectal Cancer Survival. Clin. Cancer Res. 17, 7139-7147.
11. Collin, M., Bigley, V., Haniffa, M., and Hambleton, S. (2011). Human dendritic cell deficiency: the missing ID? Nat. Rev. Immunol 11, 575-583.
12. Desmetz, C., Mange, A., Maudelonde, T., and Solassol, J. (2011). Autoantibody signatures: progress and perspectives for early cancer detection. J. Cell Mol. Med. 15, 2013-2024.
13. Falo, L. D., Kovacsovics-Bankowski, M., Thompson, K., and Rock, K. L. (1995). Targeting antigen into the phagocytic pathway in vivo induces protective tumour immunity Nat. Med. 1, 649-653.
14. Garrett, W. S., Punit, S., Gallini, C. A., Michaud, M., Zhang, D., Sigrist, K. S., Lord, G. M., Glickman, J. N., and Glimcher, L. H. (2009). Colitis-Associated Colorectal Cancer Driven by T-bet Deficiency in Dendritic Cells. Cancer Cell 16, 208-219.
15. Gerosa, F., Paganin, C., Peritt, D., Paiola, F., Scupoli, M., Aste-Amezaga, M., Frank, I., and Trinchieri, G. (1996). Interleukin-12 primes human CD4 and CD8 T cell clones for high production of both interferon-gamma and interleukin-10. J. Exp. Med. 183, 2559-2569.
16. Grivennikov, S. I., Wang, K., Mucida, D., Stewart, C. A., Schnabl, B., Jauch, D., Taniguchi, K., Yu, G. Y., Osterreicher, C. H., Hung, K. E., et al. (2012). Adenoma-linked barrier defects and microbial products drive IL-23/IL-17-mediated tumour growth. Nature 491, 254-258.
17. Herrinton, L. J., Liu, L., Levin, T. R., Allison, J. E., Lewis, J. D., and Velayos, F. (2012). Incidence and mortality of colorectal adenocarcinoma in persons with inflammatory bowel disease from 1998 to 2010. Gastroenterology 143, 382-389.
18. Karamitopoulou, E., Zlobec, I., Panayiotides, I., Patsouris, E. S., Peros, G., Rallis, G., Lapas, C., Karakitsos, P., Terracciano, L. M., and Lugli, A. (2011). Systematic analysis of proteins from different signaling pathways in the tumor center and the invasive front of colorectal cancer. Hum. Pathol. 42, 1888-1896.
19. Keely, S., Talley, N. J., and Hansbro, P. M. (2011) Pulmonary-intestinal cross-talk in mucosal inflammatory disease. Mucosal Immunol 5, 7-18.
20. Kepp, O., Tesniere, A., Zitvogel, L., and Kroemer, G. (2009). The immunogenicity of tumor cell death. Curr. Opin. Oncol. 21, 71-76.
21. Kijanka, G., Hector, S., Kay, E. W., Murray, F., Cummins, R., Murphy, D., MacCraith, B. D., Prehn, J. H. M., and Kenny, D. (2010). Human IgG antibody profiles differentiate between symptomatic patients with and without colorectal cancer. Gut 59, 69-78.
22. Kobayashi, K., Qiao, S. W., Yoshida, M., Baker, K., Lencer, W. I., and Blumberg, R. S. (2009). An FcRn-dependent role for anti-flagellin immunoglobulin G in pathogenesis of colitis in mice. Gastroenterology 137, 1746-1756 e1741.
23. Kozlowski, P. A., Cu-Uvin, S., Neutra, M. R., and Flanigan, T. P. (1997). Comparison of the oral, rectal, and vaginal immunization routes for induction of antibodies in rectal and genital tract secretions of women. Infect. Immun. 65, 1387-1394.
24. Le Floc'h, A., Jalil, A., Vergnon, I., Chansac, B. L. M., Lazar, V., Bismuth, G., Chouaib, S., and Mami-Chouaib, F. (2007). αEβ7 integrin interaction with E-cadherin promotes antitumor CTL activity by triggering lytic granule polarization and exocytosis. J. Exp. Med. 204, 559-570.
25. LeibundGut-Landmann, S., Osorio, F., Brown, G. D., and Reis e Sousa, C. (2008). Stimulation of dendritic cells via the dectin-1/Syk pathway allows priming of cytotoxic T-cell responses. Blood 112, 4971-4980.
26. Liu, J., Cao, S., Herman, L. M., and Ma, X. (2003). Differential Regulation of Interleukin (IL)-12p35 and p40 Gene Expression and Interferon (IFN)-gamma primed IL-12 Production by IFN Regulatory Factor 1. J. Exp. Med. 198, 1265-1276.
27. Ma, Y., Aymeric, L., Locher, C., Kroemer, G., and Zitvogel, L. (2011). The dendritic cell-tumor cross-talk in cancer. Curr. Opin. Immunol 23, 146-152.
28. MacDonald, T. T., Monteleone, I., Fantini, M. C., and Monteleone, G. (2011). Regulation of Homeostasis and Inflammation in the Intestine. Gastroenterology 140, 1768-1775.
29. Macpherson, A., Khoo, U. Y., Forgacs, I., Philpott-Howard, J., and Bjarnason, I. (1996). Mucosal antibodies in inflammatory bowel disease are directed against intestinal bacteria. Gut 38, 365-375.
30. MacSween, J. M., and Eastwood, S. L. (1980) Immunoglobulins associated with human tumours in vivo: igg concentrations in eluates of colonic carcinomas. Br. J. Cancer 42, 503-509.
31. Metzger, D. W. (2010). Interleukin-12 as an adjuvant for induction of protective antibody responses. Cytokine 52, 102-107.
32. Meunier, C., Cai, J., Fortin, A., Kwan, T., Marquis, J. F., Turbide, C., Van Der Kraak, L., Jothy, S., Beauchemin, N., and Gros, P. (2009). Characterization of a major colon cancer susceptibility locus (Ccs3) on mouse chromosome 3. Oncogene 29, 647-661.
33. Mi, W., Wanjie, S., Lo, S. T., Gan, Z., Pickl-Herk, B., Ober, R. J., and Ward, E. S. (2008). Targeting the neonatal fc receptor for antigen delivery using engineered fc fragments. J. Immunol 181, 7550-7561.
34. Montoyo, H. P., Vaccaro, C., Hafner, M., Ober, R. J., Mueller, W., and Ward, E. S. (2009). Conditional deletion of the MHC class I-related receptor FcRn reveals the sites of IgG homeostasis in mice. Proc. Natl. Acad. Sci. U.S.A. 106, 2788-2793.

35. Mumm, John B., Emmerich, J., Zhang, X., Chan, I., Wu, L., Mauze, S., Blaisdell, S., Basham, B., Dai, J., Grein, J., et al. (2011). IL-10 Elicits IFN-gamma-Dependent Tumor Immune Surveillance. Cancer Cell 20, 781-796.

36. Murphy, T. L., Cleveland, M. G., Kulesza, P., Magram, J., and Murphy, K. M. (1995). Regulation of interleukin 12 p40 expression through an NF-kappa B half-site. Mol. Cell Biol. 15, 5258-5267.

37. Pages, F., Berger, A., Camus, M., Sanchez-Cabo, F., Costes, A., Molidor, R., Mlecnik, B., Kirilovsky, A., Nilsson, M., Damotte, D., et al. (2005). Effector Memory T Cells, Early Metastasis, and Survival in Colorectal Cancer. N. Engl. J. Med. 353, 2654-2666.

38. Palucka, K., and Banchereau, J. (2013). Dendritic-Cell-Based Therapeutic Cancer Vaccines. Immunity 39, 38-48.

39. Qiao, S. W., Kobayashi, K., Johansen, F. E., Sollid, L. M., Andersen, J. T., Milford, E., Roopenian, D. C., Lencer, W. I., and Blumberg, R. S. (2008). Dependence of antibody-mediated presentation of antigen on FcRn. Proc. Natl. Acad. Sci. U.S.A. 105, 9337-9342.

40. Revaz, V., and Nardelli-Haefliger, D. (2005). The importance of mucosal immunity in defense against epithelial cancers. Curr. Opin. Immunol 17, 175-179.

41. Roopenian, D. C., Christianson, G. J., Sproule, T. J., Brown, A. C., Akilesh, S., Jung, N., Petkova, S., Avanessian, L., Choi, E. Y., Shaffer, D. J., et al. (2003). The MHC class I-like IgG receptor controls perinatal IgG transport, IgG homeostasis, and fate of IgG-Fc-coupled drugs. J. Immunol 170, 3528-3533.

42. Saleh, M., and Trinchieri, G. (2011). Innate immune mechanisms of colitis and colitis-associated colorectal cancer. Nat. Rev. Immunol 11, 9-20.

43. Siegel, R., Naishadham, D., and Jemal, A. (2012). Cancer statistics, 2012. CA. Cancer J. Clin. 62, 10-29.

44. Spiekermann, G. M., Finn, P. W., Ward, E. S., Dumont, J., Dickinson, B. L., Blumberg, R. S., and Lencer, W. I. (2002). Receptor-mediated immunoglobulin G transport across mucosal barriers in adult life: functional expression of FcRn in the mammalian lung. J. Exp. Med. 196, 303-310.

45. Tacken, P. J., de Vries, I. J. M., Torensma, R., and Figdor, C. G. (2007). Dendritic-cell immunotherapy: from ex vivo loading to in vivo targeting. Nat. Rev. Immunol 7, 790-802.

46. Trinchieri, G. (2003). Interleukin-12 and the regulation of innate resistance and adaptive immunity Nat. Rev. Immunol 3, 133.

47. Uronis, J. M., Arthur, J. C., Keku, T., Fodor, A., Carroll, I. M., Cruz, M. L., Appleyard, C. B., and Jobin, C. (2011). Gut microbial diversity is reduced by the probiotic VSL#3 and correlates with decreased TNBS-induced colitis. Inflamm. Bowel Dis. 17, 289-297.

48. Vaughn, D. E., Milburn, C. M., Penny, D. M., Martin, W. L., Johnson, J. L., and Bjorkman, P. J. (1997). Identification of critical IgG binding epitopes on the neonatal Fc receptor. J. Mol. Biol. 274, 597-607.

49. Walther, A., Johnstone, E., Swanton, C., Midgley, R., Tomlinson, I., and Kerr, D. (2009). Genetic prognostic and predictive markers in colorectal cancer. Nat. Rev. Cancer 9, 489-499.

50. Wirtz, S., Neufert, C., Weigmann, B., and Neurath, M. F. (2007). Chemically induced mouse models of intestinal inflammation. Nat. Protoc. 2, 541-546.

51. Wysocka, M., Kubin, M., Vieira, L. Q., Ozmen, L., Garotta, G., Scott, P., and Trinchieri, G. (1995). Interleukin-12 is required for interferon-γ production and lethality in lipopolysaccharide-induced shock in mice. Eur. J. Immunol 25, 672-676.

52. Yoshida, M., Claypool, S. M., Wagner, J. S., Mizoguchi, E., Mizoguchi, A., Roopenian, D. C., Lencer, W. I., and Blumberg, R. S. (2004). Human neonatal Fc receptor mediates transport of IgG into luminal secretions for delivery of antigens to mucosal dendritic cells Immunity 20, 769-783.

53. Yoshida, M., Kobayashi, K., Kuo, T. T., Bry, L., Glickman, J. N., Claypool, S. M., Kaser, A., Nagaishi, T., Higgins, D. E., Mizoguchi, E., et al. (2006). Neonatal Fc receptor for IgG regulates mucosal immune responses to luminal bacteria. J. Clin. Invest. 116, 2142-2151.

54. Zalevsky, J., Chamberlain, A. K., Horton, H. M., Karki, S., Leung, I. W. L., Sproule, T. J., Lazar, G. A., Roopenian, D. C., and Desjarlais, J. R. (2010) Enhanced antibody half-life improves in vivo activity. Nat. Biotechnol. 28, 157-159.

55. Zeissig, S., Dougan, S. K., Barral, D. C., Junker, Y., Chen, Z., Kaser, A., Ho, M., Mandel, H., McIntyre, A., Kennedy, S. M., et al. (2010). Primary deficiency of microsomal triglyceride transfer protein in human abetalipoproteinemia is associated with loss of CD1 function. J. Clin. Invest. 120, 2889-2899.

56. Zhang, N., and Bevan, Michael J. (2011). CD8+ T Cells: Foot Soldiers of the Immune System. Immunity 35, 161-168.

57. Zhu, X., Meng, G., Dickinson, B. L., Li, X., Mizoguchi, E., Miao, L., Wang, Y., Robert, C., Wu, B., Smith, P. D., et al. (2001). MHC class I-related neonatal Fc receptor for IgG is functionally expressed in monocytes, intestinal macrophages, and dendritic cells. J. Immunol. 166, 3266-3276.

58. Arthur, J. C., Perez-Chanona, E., Muhlbauer, M., Tomkovich, S., Uronis, J. M., Fan, T. J., Campbell, B. J., Abujamel, T., Dogan, B., Rogers, A. B., et al. (2012). Intestinal inflammation targets cancer-inducing activity of the microbiota. Science 338, 120-123.

59. Baker, K., Qiao, S.-W., Kuo, T. T., Aveson, V. G., Platzer, B., Andersen, J.-T., Sandlie, I., Chen, Z., de Haar, C., Lencer, W. I., et al. (2011). Neonatal Fc receptor for IgG (FcRn) regulates crosspresentation of IgG immune complexes by CD8–CD11b+ dendritic cells. Proc. Natl. Acad. Sci. U.S.A. 108, 9927-9932.

60. Falo, L. D., Kovacsovics-Bankowski, M., Thompson, K., and Rock, K. L. (1995). Targeting antigen into the phagocytic pathway in vivo induces protective tumour immunity Nat. Med. 1, 649-653.

61. Grivennikov, S. I., Wang, K., Mucida, D., Stewart, C. A., Schnabl, B., Jauch, D., Taniguchi, K., Yu, G. Y., Osterreicher, C. H., Hung, K. E., et al. (2012). Adenoma-linked barrier defects and microbial products drive IL-23/IL-17-mediated tumour growth. Nature 491, 254-258.

62. Kruisbeek, A. M. (1991). In Vivo Depletion of CD4- and CD8-Specific T Cells. Curr. Prot. Immunol 1, 4.1.1-4.1.5.

63. LeibundGut-Landmann, S., Osorio, F., Brown, G. D., and Reis e Sousa, C. (2008). Stimulation of dendritic cells via the dectin1/Syk pathway allows priming of cytotoxic T-cell responses. Blood 112, 4971-4980.

64. Miyamoto, Y., Watanabe, K., Tanaka, R., and Itoh, K. (2002). Distribution Analysis of Six Predominant Bacteroides Species in Normal Human Feces Using 16S rDNA-Targeted Species-Specific Primers. Microbial Ecology in Health and Disease 14, 133-136.

65. Montoyo, H. P., Vaccaro, C., Hafner, M., Ober, R. J., Mueller, W., and Ward, E. S. (2009). Conditional deletion of the MHC class I-related receptor FcRn reveals the sites of IgG homeostasis in mice. Proc. Natl. Acad. Sci. U.S.A. 106, 2788-2793.
66. Ober, R. J., Radu, C. G., Ghetie, V., and Ward, E. S. (2001). Differences in promiscuity for antibody-FcRn interactions across species: implications for therapeutic antibodies. Int. Immunol 13, 1551-1559.
67. Olszak, T., An, D., Zeissig, S., Vera, M. P., Richter, J., Franke, A., Glickman, J. N., Siebert, R., Baron, R. M., Kasper, D. L., and Blumberg, R. S. (2012). Microbial exposure during early life has persistent effects on natural killer T cell function. Science 336, 489-493.
68. Periasamy, S., and Kolenbrander, P. E. (2009). Aggregatibacter actinomycetemcomitans Builds Mutualistic Biofilm Communities with *Fusobacterium nucleatum* and *Veillonella* Species in Saliva. Infect. Immun. 77, 3542-3551.
69. Rabizadeh, S., Rhee, K.-J., Wu, S., Huso, D., Gan, C. M., Golub, J. E., Wu, X., Zhang, M., and Sears, C. L. (2007). Enterotoxigenic Bacteroides fragilis: A potential instigator of colitis. Inflamm. Bowel Dis. 13, 1475-1483.
70. Roopenian, D. C., Christianson, G. J., Sproule, T. J., Brown, A. C., Akilesh, S., Jung, N., Petkova, S., Avanessian, L., Choi, E. Y., Shaffer, D. J., et al. (2003). The MHC class I-like IgG receptor controls perinatal IgG transport, IgG homeostasis, and fate of IgG-Fc-coupled drugs. J. Immunol 170, 3528-3533.
71. Shames, B., Fox, J. G., Dewhirst, F., Yan, L., Shen, Z., and Taylor, N. S. (1995). Identification of widespread Helicobacter hepaticus infection in feces in commercial mouse colonies by culture and PCR assay. J. Clin. Microbiol. 33, 2968-2972.
72. Uronis, J. M., Arthur, J. C., Keku, T., Fodor, A., Carroll, I. M., Cruz, M. L., Appleyard, C. B., and Jobin, C. (2011). Gut microbial diversity is reduced by the probiotic VSL#3 and correlates with decreased TNBS-induced colitis. Inflamm. Bowel Dis. 17, 289-297.
73. Wirtz, S., Neufert, C., Weigmann, B., and Neurath, M. F. (2007). Chemically induced mouse models of intestinal inflammation. Nat. Protoc. 2, 541-546.
74. Yoshida, M., Claypool, S. M., Wagner, J. S., Mizoguchi, E., Mizoguchi, A., Roopenian, D. C., Lencer, W. I., and Blumberg, R. S. (2004). Human neonatal Fc receptor mediates transport of IgG into luminal secretions for delivery of antigens to mucosal dendritic cells Immunity 20, 769-783.
75. Zalevsky, J., Chamberlain, A. K., Horton, H. M., Karki, S., Leung, I. W. L., Sproule, T. J., Lazar, G. A., Roopenian, D. C., and Desjarlais, J. R. (2010) Enhanced antibody half-life improves in vivo activity. Nat. Biotechnol. 28, 157-159.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the a person of ordinary skill in the art will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

We claim:

1. A method for determining the efficacy of treatment in a subject in need thereof comprising:
   (a) administering to the subject a treatment comprising a composition comprising an anti-FcRn antibody that inhibits signaling mediated by interaction between FcRn and IgG;
   (b) providing a sample from the subject, wherein the sample is blood, plasma or tissue;
   (c) assaying the level of IL-12, in the sample; and
   (d) determining that the treatment is efficacious if the level of IL-12, in the sample from the subject is lower relative to the level in a reference sample or determining that the treatment is not efficacious if the level of IL-12, in the sample from the subject is higher relative to the level in a reference sample,
   wherein the subject has an autoimmune disease.

2. The method of claim 1, wherein the antibody is selected from the group consisting of a monoclonal antibody or a fragment thereof, a polyclonal antibody or a fragment thereof, chimeric antibody, humanized antibody and single chain antibody.

* * * * *

UNITED STATES PATENT AND TRADEMARK OFFICE
CERTIFICATE OF CORRECTION

| | |
|---|---|
| PATENT NO. | : 10,035,858 B2 |
| APPLICATION NO. | : 15/039524 |
| DATED | : July 31, 2018 |
| INVENTOR(S) | : Blumberg et al. |

It is certified that error appears in the above-identified patent and that said Letters Patent is hereby corrected as shown below:

In the Specification

At Column 1, Lines 17-20:
"The invention was made with government support under Grant No. DK53056 awarded by the National Institutes of Health. The government has certain rights to the invention." should be replaced with --This invention was made with government support under DK053056 awarded by the National Institutes of Health. The government has certain rights in the invention.--

Signed and Sealed this
Second Day of May, 2023

Katherine Kelly Vidal
*Director of the United States Patent and Trademark Office*